US009551722B2

(12) United States Patent
Yang et al.

(10) Patent No.: US 9,551,722 B2
(45) **Date of Patent: *Jan. 24, 2017**

(54) AMYLOID BINDING AGENTS

(71) Applicant: The Regents of the University of California, Oakland, CA (US)

(72) Inventors: Jerry Yang, La Jolla, CA (US); Emmanuel A. Theodorakis, San Diego, CA (US)

(73) Assignee: THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/572,465

(22) Filed: Dec. 16, 2014

(65) Prior Publication Data

US 2015/0177262 A1 Jun. 25, 2015

Related U.S. Application Data

(63) Continuation of application No. 13/515,239, filed as application No. PCT/US2010/059952 on Dec. 10, 2010, now Pat. No. 8,940,918.

(60) Provisional application No. 61/285,470, filed on Dec. 10, 2009.

(51) Int. Cl.

| | |
|---|---|
| ***C07C 255/42*** | (2006.01) |
| ***G01N 33/68*** | (2006.01) |
| ***C07C 255/43*** | (2006.01) |
| ***C07D 295/13*** | (2006.01) |
| ***C07D 295/155*** | (2006.01) |
| ***C07D 317/24*** | (2006.01) |

(52) U.S. Cl.
CPC ......... *G01N 33/6896* (2013.01); *C07C 255/42* (2013.01); *C07C 255/43* (2013.01); *C07D 295/13* (2013.01); *C07D 295/155* (2013.01); *C07D 317/24* (2013.01); *G01N 2333/4703* (2013.01)

(58) Field of Classification Search
CPC .................................................... C07C 255/42
USPC ........................................................ 558/403
See application file for complete search history.

(56) References Cited

U.S. PATENT DOCUMENTS

| | | | |
|---|---|---|---|
| 2,583,614 | A | 1/1952 | Taylor et al. |
| 2,798,090 | A | 7/1957 | Krell et al. |
| 4,258,182 | A | 3/1981 | Beecken |
| 4,861,760 | A | 8/1989 | Mazuel et al. |
| 4,911,920 | A | 3/1990 | Jani et al. |
| 5,212,162 | A | 5/1993 | Missel et al. |
| 5,403,841 | A | 4/1995 | Lang et al. |
| 5,874,180 | A | 2/1999 | Wehrmann et al. |
| 2007/0066665 | A1 | 3/2007 | Yang et al. |
| 2009/0281348 | A1 | 11/2009 | Henkelmann et al. |

FOREIGN PATENT DOCUMENTS

| | | | |
|---|---|---|---|
| FR | 1321641 A | 3/1963 | |
| JP | 58015912 A | 1/1983 | |
| WO | WO-96/05309 A2 | 2/1996 | |
| WO | WO-2004/078144 A2 | 9/2004 | |
| WO | WO-2005/073697 A1 | 8/2005 | |
| WO | WO-2008/015103 A2 | 2/2008 | |
| WO | WO 2009052837 A2 * | 4/2009 | ......... G01N 33/6851 |

OTHER PUBLICATIONS

Biinziger et al., "A New Practical Route for the Manufacture of (4aR, 10aR)-9-Methoxy-1-methyl-6-trimethylsilanyl-1, 2, 3, 4, 4a, 5,10,10a-octahydrobenzo[g]quinoline", *Organic Process Research & Development*, 7(6):904-912 (2003).

Diaz-Garcia et al., "Photorefractive Properties of Poly(N-vinyl carbazole)-Based Composites for High Speed Applications," Chemistry of Materials, 11(7):1784-1791 (1999).

Haidekker et al., A Ratiometric Fluorescent Viscosity Sensor, *Journal of the American Chemical Society*, 128:398-399 (2006).

Haidekker et al., "Hydrophilic molecular rotor derivatives-synthesis and characterization," Bioorganic Chemistry, 32(4):274-289 (2004).

Lupo et al., "Amphiphilic Nonlinear Optical Bis-chromophores and Their Mixtures with Amphotropic Copolymers: Preparation of Monolayers and Langmuir-Blodgett Multilayers," *Journal of the American Chemical Society*, 116:10498-10506 (1994).

Rondou et al., "Synthesis of frequency doubling polymeric materials, 1 Second-order nonlinear optical properties of poled chromophore-functionalized polymethacrylates", *Macromolecular Chemistry and Physics*,193(12):3045-3055 (1992).

Senchenya et al., "Silicon-containing esters of alpha-cyanoacrylic acid:synthesis and properties", *Russian Chemical Bulletin*, 1993, 42(5):909-911 (1993) Kluwer Academic Publishers-Plenum Publishers ISSN:1573-9171.

Sutharsan et al., "Rational Design of Amyloid Binding Agents Based on the Molecular Rotor Motif", *ChemMedChem* (2010, Article first published online: Dec. 18, 2009), 5(1):56-60, ISSN: 1860-7179.

Xu et al., "Microwave-assisted three-component Knoevenagel-nucleophilic aromatic substitution reactions", *Tetrahedron Letters*, 49:4687-4689 (2008).

* cited by examiner

*Primary Examiner* — David K O'Dell

(74) *Attorney, Agent, or Firm* — Mintz Levin Cohn Ferris Glovsky and Popeo, P.C.

(57) ABSTRACT

There are provided compounds and methods for the detection of amyloids and treatment of diseases related to amyloids including Alzheimer's disease and other related amyloid-based neurodegenerative diseases.

15 Claims, 16 Drawing Sheets

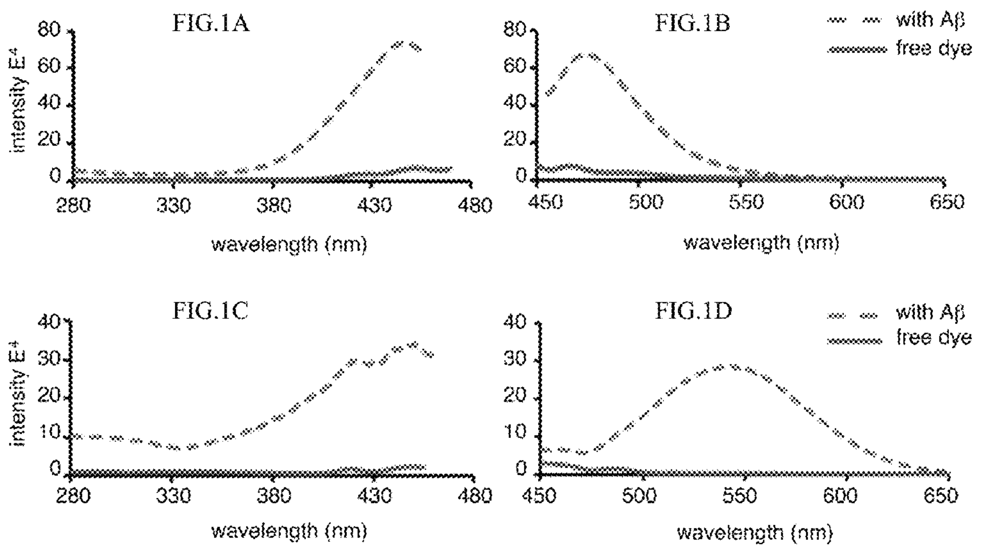
Fig. 2.
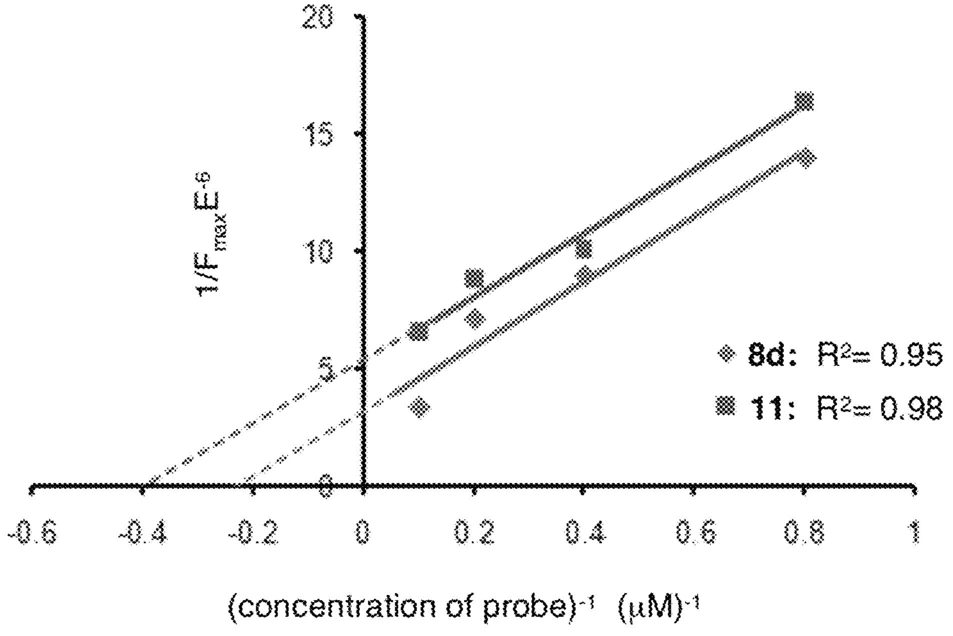

Fig. 3.
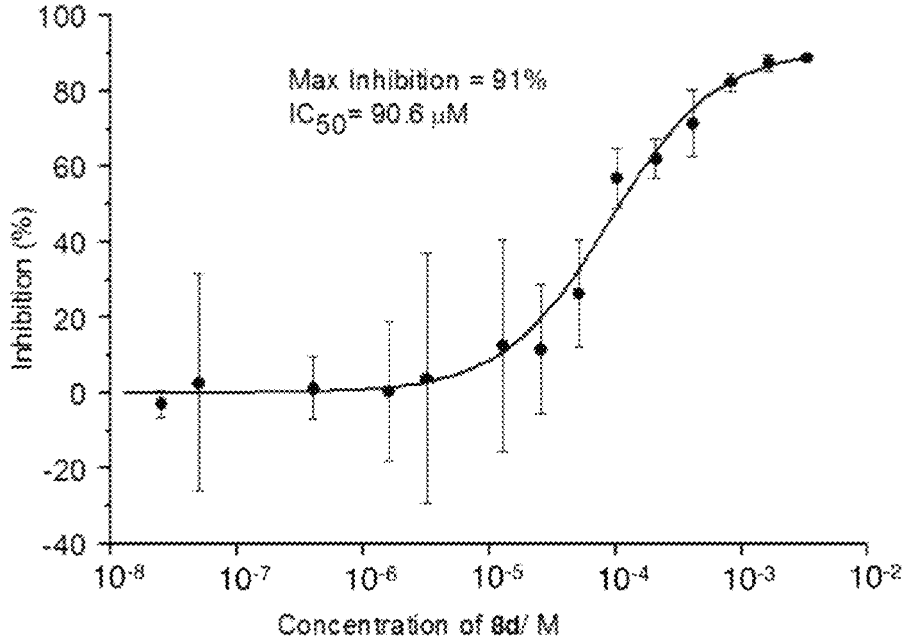
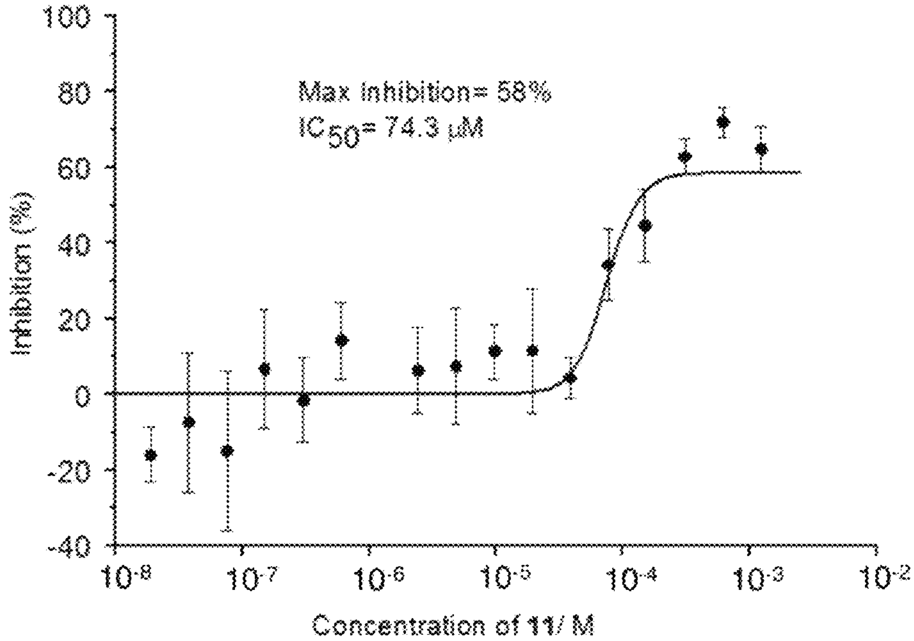

AMYLOID BINDING AGENTS

CROSS-REFERENCES TO RELATED APPLICATIONS

This application claims priority to U.S. Application No. 61/285,470, filed Dec. 10, 2009, the entire content of which is incorporated herein by reference.

STATEMENT AS TO RIGHTS TO INVENTIONS MADE UNDER FEDERALLY SPONSORED RESEARCH AND DEVELOPMENT

This invention was made with government support under Grant No. 1E21RR025358 awarded by National Institutes of Health (NIH). The government has certain rights in the invention.

BACKGROUND

Alzheimer's disease (AD) is characterized by a progressive loss of cognitive function and constitutes the most common and fatal neurodegenerative disorder. Genetic and clinical evidence supports the hypothesis that accumulation of amyloid deposits in the brain plays an important role in the pathology of the disease. This event is associated with perturbations of biological functions in the surrounding tissue leading to neuronal cell death, thus contributing to the disease process. The deposits are composed primarily of amyloid (Aβ) peptides, typically a 39-43 amino acid sequence that self aggregates into a fibrillar β-pleated sheet motif. While the exact three-dimensional structure of the aggregated Aβ peptides is not known, a model structure that sustains the property of aggregation has been proposed. This creates opportunities for in vivo imaging of amyloid deposits that not only can help evaluate the time course and evolution of the disease but can also allow the timely monitoring of therapeutic treatments.

Historically, Congo Red (CR) and Thioflavin T (ThT) have provided the starting point for the visualization of amyloid plaques and are still commonly employed in post mortem histological analyses. However, due to their charge these compounds are thought to be unsuitable for in vivo applications. To address this issue, several laboratories developed compounds with non charged, lipophilic (log P=0.1-3.5) and low molecular weight chemical structures (M.W. less than 650) that facilitate crossing of the blood brain barrier. Further functionalization of these compounds with radio-nuclides led to a new generation of in vivo diagnostic reagents that target plaques and related structures for imaging with positron emission tomography (PET) and single-photon emission computed tomography (SPECT), as known in the art.

Despite these advances, there is a pressing need for the design and development of new amyloid-targeting molecules with improved physical, chemical and biological characteristics. Provided herein are methods and compounds addressing these and other needs in the art.

BRIEF SUMMARY

Herein are provided inter alia compounds and methods for the detection of amyloids and treatment of diseases related to amyloids including Alzheimer's disease and other related amyloid-based neurodegenerative diseases.

In a first aspect, compounds that bind amyloid peptides and/or amyloids (e.g., amyloid peptide aggregates) are provided. In some embodiments, the compounds described herein have the structure of Formula (I):

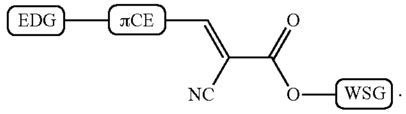

(I)

In Formula I, "EDG" is an electron donating group. The term "πCE" is a pi-conjugation element. "WSG" is a water soluble group.

In another aspect, there is provided a pharmaceutical composition. The pharmaceutical composition includes a compound described herein and a pharmaceutically acceptable excipient.

In another aspect, there is provided a method of detecting an amyloid peptide and/or an amyloid. The method includes contacting a compound as described herein with an amyloid peptide thereby forming a detectable amyloid complex, and detecting the detectable amyloid complex.

In another aspect, there is provided a method of treating a disease characterized by an accumulation of amyloids (e.g., amyloid deposits) in a subject. The method includes administering to a subject in need of treatment an effective amount of a compound or pharmaceutical composition as described herein.

BRIEF DESCRIPTION OF THE DRAWINGS

FIGS. 1A-D depict fluorescence excitation and emission spectra of Cmpds 8d and 11 in aqueous PBS solution (solid lines) and in the presence of Aβ peptide (dashed lined). FIG. 1A: fluorescence excitation spectrum of Cmpd 8d. FIG. 1B: emission spectrum of Cmpd 8d. FIG. 1C: fluorescence excitation spectrum of Cmpd 11. FIG. 1D: emission spectrum of Cmpd 11.

FIG. 2 depicts the apparent binding constant ($K_d$) of Cmpds 8d and 11 to preaggregated Aβ peptide. Legend: Cmpd 8d (diamond); Cmpd 11 (box).

FIG. 3 depicts the inhibition of IgG-Aβ fibril interactions with Cmpd 8d (FIG. 3 top) and Cmpd 11 (FIG. 3 bottom).

FIG. 7A: Cmpd 8a; FIG. 7B: Cmpd 8b; FIG. 7C: Cmpd 8c; FIG. 7D: Cmpd 14.

DETAILED DESCRIPTION

I. Definitions

Figure 4:
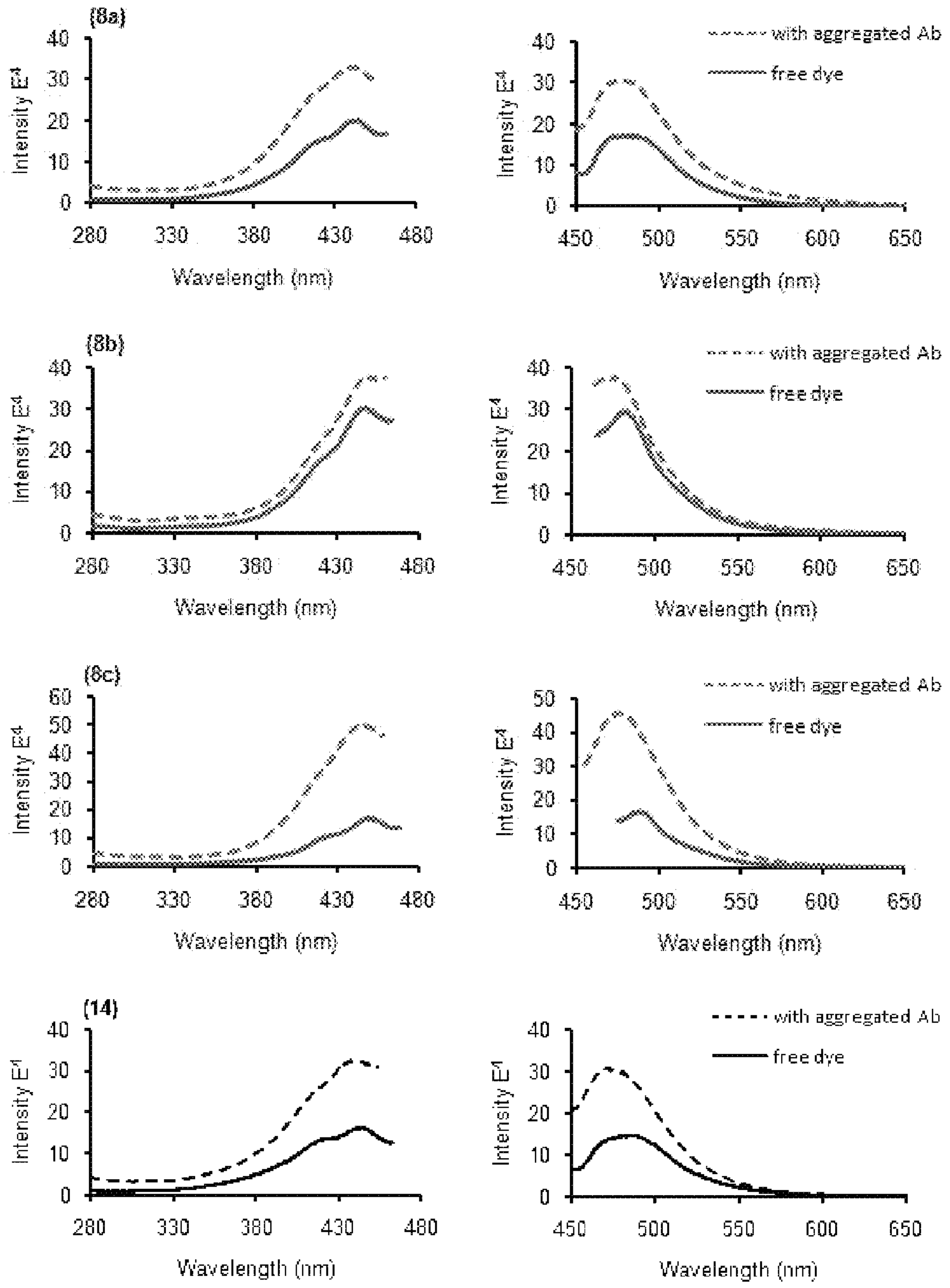
FIG. 4 depicts fluorescence excitation spectra (left panels) and emission spectra (right panels) for Cmpds 8a, 8b, 8c, 14 and 19 with aggregated Aβ(1-42) fibril, as described herein.
Figure 4:
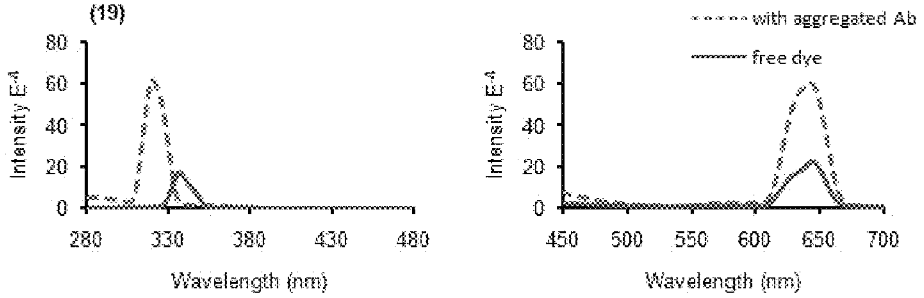
Figure 5:
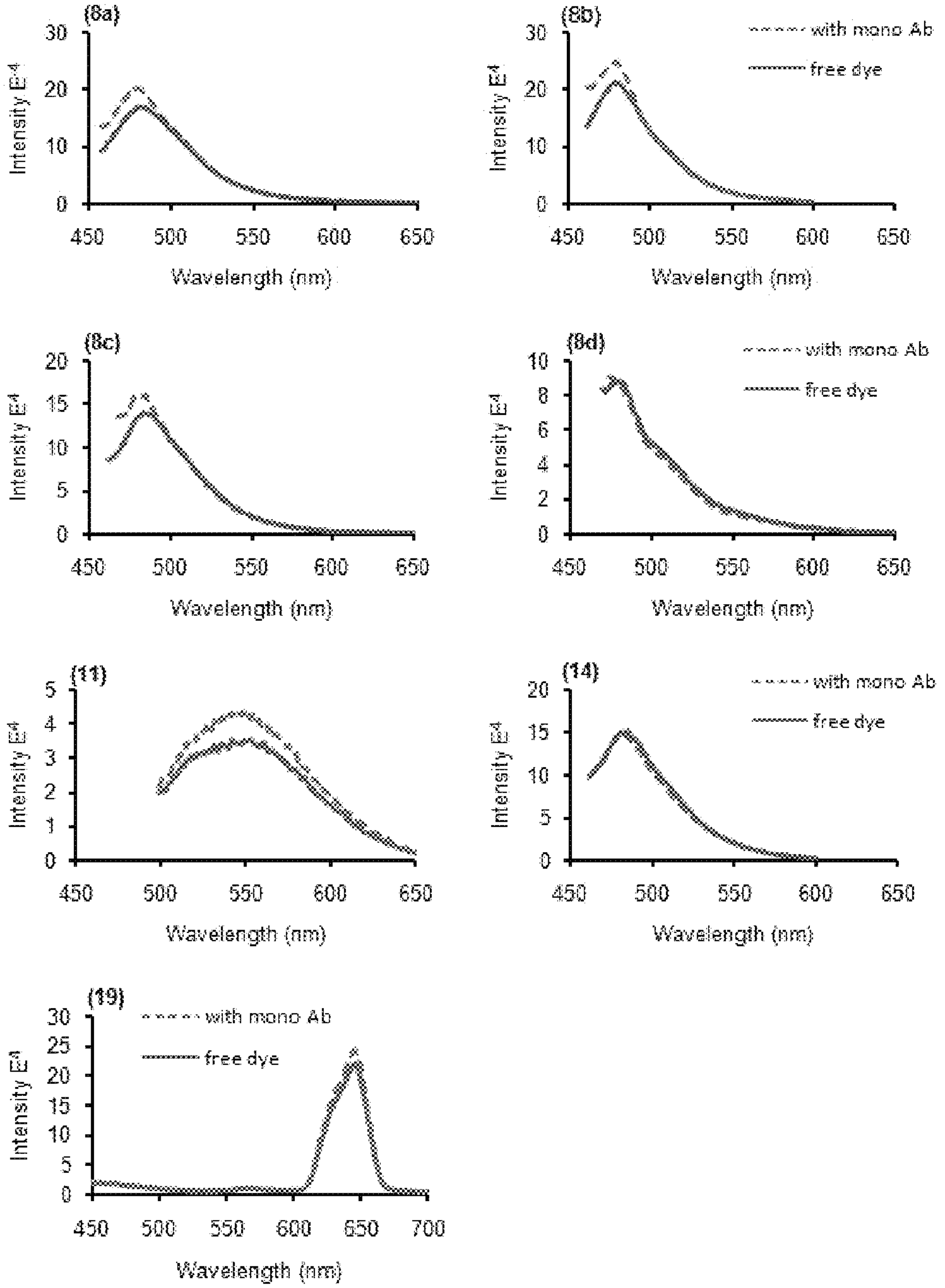
FIG. 5 depicts fluorescence emission spectra of Cmpds 8a, 8b, 8c, 8d, 11, 14 and 19 with and without monomeric Aβ monomer, as described herein.

The abbreviations used herein have their conventional meaning within the chemical and biological arts. The chemical structures and formulae set forth herein are constructed according to the standard rules of chemical valency known in the chemical arts.

Where substituent groups are specified by their conventional chemical formulae, written from left to right, they equally encompass the chemically identical substituents that would result from writing the structure from right to left, e.g., $—CH_2O—$ is equivalent to $—OCH_2—$.

The term "electron donating group (EDG)" refers to a chemical moiety that modifies the electrostatic forces acting on a nearby chemical moiety by donating negative charge to that chemical moiety. In some embodiments, the electron donating group donates negative charge to the π-conjugation element of the compounds disclosed herein.

The term "π-conjugation element," "πCE" or "pi-conjugation element" refers to a divalent chemical moiety that forms a π-conjugated system that has alternating single and multiple bonds (e.g., double bonds) such that the electrons in the p-orbitals of the atoms in the system are delocalized. In some embodiments, the single and multiple bonds in the π-conjugated element can be in a planar or substantially planar orientation.

The term "water soluble group" refers to a chemical moiety that increases the water solubility of the compounds to which it is attached. Increasing the water solubility can be measured using existing techniques in the art, such as by determining a partition constant of the compounds with and without an attached water soluble group. In some embodiments, the partition constant can be measured by mixing a compound with water and a hydrophobic solvent, such as octanol. The more hydrophobic a compound, the higher its partition constant. The more hydrophilic a compound, the lower its partition constant. In some embodiments, the water soluble groups described herein can improve the water solubility of precursor molecules by decreasing their partition coefficient. In some embodiments, the water soluble groups can decrease the partition constant of precursor molecules (which have a higher partition constant before attachment of the water soluble group) at least by about 10%, 20%, 30%, 40%, 50%, 60%, 70%, 80%, or 90%. In some embodiments, the water soluble groups described herein can decrease the partition constant of precursor molecules by 1-fold, 2-fold, 3-fold, 4-fold, or greater.

The term "amyloid" is used herein according to its customary meaning in the art. Amyloids contain a plurality of associated amyloid peptides, such as aggregates of amyloid peptides. Thus, in some embodiments, amyloids include an amyloid peptide aggregated with one or more amyloid peptides. In some embodiments, amyloids include "amyloid plaques," amyloid deposits," "amyloid aggregates" or "aggregates of amyloid peptides." The compounds described herein can associate with (e.g., bind) an amyloid peptide and/or an amyloid. In certain embodiments, the compounds described herein can associate with an amyloid by hydrophobic interactions.

The term "alkyl," by itself or as part of another substituent, means, unless otherwise stated, a straight (i.e. unbranched) or branched chain, or combination thereof, which may be fully saturated, mono- or polyunsaturated and can include di- and multivalent radicals, having the number of carbon atoms designated (i.e. $C_1$-$C_{10}$ means one to ten carbons). Examples of saturated hydrocarbon radicals include, but are not limited to, groups such as methyl, ethyl, n-propyl, isopropyl, n-butyl, t-butyl, isobutyl, sec-butyl, (cyclohexyl)methyl, homologs and isomers of, for example, n-pentyl, n-hexyl, n-heptyl, n-octyl, and the like. An unsaturated alkyl group is one having one or more double bonds or triple bonds. Examples of unsaturated alkyl groups include, but are not limited to, vinyl, 2-propenyl, crotyl, 2-isopentenyl, 2-(butadienyl), 2,4-pentadienyl, 3-(1,4-pentadienyl), ethynyl, 1- and 3-propynyl, 3-butynyl, and the higher homologs and isomers. An alkoxy is an alkyl attached to the remainder of the molecule via an oxygen linker (—O—).

The term "alkylene" by itself or as part of another substituent means a divalent radical derived from an alkyl, as exemplified, but not limited, by $—CH_2CH_2CH_2CH_2—$, and further includes those groups described below as "heteroalkylene." Typically, an alkyl (or alkylene) group will have from 1 to 24 carbon atoms, with those groups having 10 or fewer carbon atoms being preferred. A "lower alkyl" or "lower alkylene" is a shorter chain alkyl or alkylene group, generally having eight or fewer carbon atoms.

The term "heteroalkyl," by itself or in combination with another term, means, unless otherwise stated, a stable straight or branched chain, or cyclic hydrocarbon radical, or combinations thereof, consisting of at least one carbon atoms and at least one heteroatom selected from the group consisting of O, N, P, Si and S. The nitrogen and sulfur atoms may optionally be oxidized, and the nitrogen heteroatom may optionally be quaternized. The heteroatom(s) O, N, P and S and Si may be placed at any interior position of the heteroalkyl group or at the position at which the alkyl group is attached to the remainder of the molecule. Examples include, but are not limited to, $—CH_2—CH_2—O—CH_3$, $—CH_2—CH_2—NH—CH_3$, $—CH_2—CH_2—N(CH_3)—CH_3$, $—CH_2—S—CH_2—CH_3$, $—CH_2—CH_2$, $—S(O)—CH_3$, $—CH_2—CH_2—S(O)_2—CH_3$, $—CH{=}CH—O—CH_3$, $—Si(CH_3)_3$, $—CH_2—CH{=}N—OCH_3$, $CH{=}CH—N(CH_3)—CH_3$, $O—CH_3$, $—O—CH_{-2}$-$CH_3$, and —CN. Up to two heteroatoms may be consecutive, such as, for example, $—CH_2—NH—OCH_3$. Similarly, the term "heteroalkylene" by itself or as part of another substituent means a divalent radical derived from heteroalkyl, as exemplified, but not limited by, $—CH_2—CH_2—S—CH_2—CH_2—$ and $—CH_2—S—CH_2—CH_2—NH—CH_2—$. For heteroalkylene groups, heteroatoms can also occupy either or both of the chain termini (e.g., alkyleneoxy, alkylenedioxy, alkyleneamino, alkylenediamino, and the like). Still further, for alkylene and heteroalkylene linking groups, no orientation of the linking group is implied by the direction in which the formula of the linking group is written. For example, the formula $—C(O)_2R'—$ represents both $—C(O)_2R'—$ and $—R'C(O)_2—$. As described above, heteroalkyl groups, as used herein, include those groups that are attached to the remainder of the molecule through a heteroatom, such as —C(O)R', —C(O)NR', —NR'R", —OR', —SR', and/or $—SO_2R'$. Where "heteroalkyl" is recited, followed by recitations of specific heteroalkyl groups, such as —NR'R" or the like, it will be understood that the terms heteroalkyl and —NR'R" are not redundant or mutually exclusive. Rather, the specific heteroalkyl groups are recited to add clarity. Thus, the term "heteroalkyl" should not be interpreted herein as excluding specific heteroalkyl groups, such as —NR'R" or the like.

The terms "cycloalkyl" and "heterocycloalkyl," by themselves or in combination with other terms, represent, unless otherwise stated, cyclic versions of "alkyl" and "heteroalkyl", respectively. Additionally, for heterocycloalkyl, a heteroatom can occupy the position at which the heterocycle is attached to the remainder of the molecule. Examples of cycloalkyl include, but are not limited to, cyclopropyl, cyclobutyl, cyclopentyl, cyclohexyl, 1-cyclohexenyl, 3-cyclohexenyl, cycloheptyl, and the like. Examples of heterocycloalkyl include, but are not limited to, 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, and the like. A "cycloalkylene" and a "heterocycloalkylene," alone or as part of another substituent means a divalent radical derived from a cycloalkyl and heterocycloalkyl, respectively.

The terms "halo" or "halogen," by themselves or as part of another substituent, mean, unless otherwise stated, a fluorine, chlorine, bromine, or iodine atom. Additionally, terms such as "haloalkyl," are meant to include monohaloalkyl and polyhaloalkyl. For example, the term "halo($C_1$-$C_4$)alkyl" is meant to include, but not be limited to, fluoromethyl, difluoromethyl, trifluoromethyl, 2,2,2-trifluoroethyl, 4-chlorobutyl, 3-bromopropyl, and the like.

The term "acyl" means C(O)R where R is a substituted or unsubstituted alkyl, substituted or unsubstituted cycloalkyl, substituted or unsubstituted heteroalkyl, substituted or unsubstituted heterocycloalkyl, substituted or unsubstituted aryl or substituted or unsubstituted heteroaryl.

The term "aryl" means, unless otherwise stated, a polyunsaturated, aromatic, hydrocarbon substituent which can be a single ring or multiple rings (preferably from 1 to 3 rings) which are fused together (i.e. a fused ring aryl) or linked covalently. A fused ring aryl refers to multiple rings fused together and at least one of the fused rings is an aryl ring. The term "heteroaryl" refers to aryl groups (or rings) that contain from one to four heteroatoms selected from N, O, and S. The nitrogen and sulfur atoms are optionally oxidized, and the nitrogen atom(s) are optionally quaternized. Thus, the term "heteroaryl" includes fused ring heteroaryl groups (i.e. multiple rings fused together wherein at least one of the fused rings is a heteroaromatic ring). A 5,6-fused ring heteroarylene refers to two rings fused together, wherein one ring has 5 members and the other ring has 6 members, and wherein at least one ring is a heteroaryl ring. Likewise, a 6,6-fused ring heteroarylene refers to two rings fused together, wherein one ring has 6 members and the other ring has 6 members, and wherein at least one ring is a heteroaryl ring. And a 6,5-fused ring heteroarylene refers to two rings fused together, wherein one ring has 6 members and the other ring has 5 members, and wherein at least one ring is a heteroaryl ring. A heteroaryl group can be attached to the remainder of the molecule through a carbon or heteroatom. Non-limiting examples of aryl and heteroaryl groups include phenyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, and 6-quinolyl. Substituents for each of the above noted aryl and heteroaryl ring systems are selected from the group of acceptable substituents described below. An "arylene" and a "heteroarylene," alone or as part of another substituent means a divalent radical derived from an aryl and heteroaryl, respectively.

For brevity, the term "aryl" when used in combination with other terms (e.g., aryloxy, arylthioxy, arylalkyl) includes both aryl and heteroaryl rings as defined above. Thus, the term "arylalkyl" is meant to include those radicals in which an aryl group is attached to an alkyl group (e.g., benzyl, phenethyl, pyridylmethyl and the like) including those alkyl groups in which a carbon atom (e.g., a methylene group) has been replaced by, for example, an oxygen atom (e.g., phenoxymethyl, 2-pyridyloxymethyl, 3-(1-naphthyloxyl)propyl, and the like).

The term "oxo" as used herein means oxygen that is double bonded to a carbon atom.

The term "alkylsulfonyl" as used herein means a moiety having the formula —$S(O_2)$—R', where R' is an alkyl group as defined above. R' may have a specified number of carbons (e.g. "$C_1$-$C_4$ alkylsulfonyl").

Each of the above terms (e.g., "alkyl," "heteroalkyl," "aryl" and "heteroaryl") are meant to include both substituted and unsubstituted forms of the indicated radical. Preferred substituents for each type of radical are provided below.

Substituents for the alkyl and heteroalkyl radicals (including those groups often referred to as alkylene, alkenyl, heteroalkylene, heteroalkenyl, alkynyl, cycloalkyl, heterocycloalkyl, cycloalkenyl, and heterocycloalkenyl) can be one or more of a variety of groups selected from, but not limited to: —OR', ═O, ═NR', ═N—OR', —NR'R", —SR', -halogen, —SiR'R"R'", —OC(O)R', —C(O)R', —$CO_2$R', —CONR'R", —OC(O)NR'R", —NR"C(O)R', —NR'—C(O)NR"R'", —NR"C(O)$_2$R', —NR—C(NR'R"R'")═NR"", —NR—C(NR'R")═NR'", —S(O)R', —S(O)$_2$R', —S(O)$_2$NR'R", —NRSO$_2$R', —CN and —$NO_2$ in a number ranging from zero to (2m'+1), where m' is the total number of carbon atoms in such radical. R', R", R'" and R"" each preferably independently refer to hydrogen, substituted or unsubstituted heteroalkyl, substituted or unsubstituted cycloalkyl, substituted or unsubstituted heterocycloalkyl, substituted or unsubstituted aryl (e.g., aryl substituted with 1-3 halogens), substituted or unsubstituted alkyl, alkoxy or thioalkoxy groups, or arylalkyl groups. When a compound disclosed herein includes more than one R group, for example, each of the R groups is independently selected as are each R', R", R' and R'" groups when more than one of these groups is present. When R' and R" are attached to the same nitrogen atom, they can be combined with the nitrogen atom to form a 4-, 5-, 6-, or 7-membered ring. For example, —NR'R" is meant to include, but not be limited to, 1-pyrrolidinyl and 4-morpholinyl. From the above discussion of substituents, one of skill in the art will understand that the term "alkyl" is meant to include groups including carbon atoms bound to groups other than hydrogen groups, such as haloalkyl (e.g., —$CF_3$ and —$CH_2CF_3$) and acyl (e.g., —C(O)$CH_3$, —C(O)$CF_3$, —C(O)$CH_2OCH_3$, and the like).

Similar to the substituents described for the alkyl radical, substituents for the aryl and heteroaryl groups are varied and are selected from, for example: halogen, —OR', —NR'R", —SR', -halogen, —SiR'R"R'", —OC(O)R', —C(O)R', —$CO_2$R', —CONR'R", —OC(O)NR'R", —NR"C(O)R', —NR'—C(O)NR"R'", —NR"C(O)$_2$R', —NR—C(NR'R"R'")═NR"", —NR—C(NR'R")═NR'", —S(O)R', —$S(O)_2R'$, —$S(O)_2NR'R''$, —$NRSO_2R'$, —CN and —$NO_2$, —R', —$N_3$, —$CH(Ph)_2$, fluoro($C_1$-$C_4$)alkoxy, and fluoro ($C_1$-$C_4$)alkyl, in a number ranging from zero to the total number of open valences on the aromatic ring system; and where R', R'', R''' and R'''' are preferably independently selected from hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl and substituted or unsubstituted heteroaryl. When a compound disclosed herein includes more than one R group, for example, each of the R groups is independently selected as are each R', R'', R' and R'''' groups when more than one of these groups is present.

Two of the substituents on adjacent atoms of the aryl or heteroaryl ring may optionally form a ring of the formula -T-C(O)—$(CRR')_q$—U—, wherein T and U are independently —NR—, —O—, —CRR'— or a single bond, and q is an integer of from 0 to 3. Alternatively, two of the substituents on adjacent atoms of the aryl or heteroaryl ring may optionally be replaced with a substituent of the formula -A-$(CH_2)_r$—B—, wherein A and B are independently —CRR'—, —O—, —NR—, —S—, —S(O)—, —$S(O)_2$—, —$S(O)_2NR'$— or a single bond, and r is an integer of from 1 to 4. One of the single bonds of the new ring so formed may optionally be replaced with a double bond. Alternatively, two of the substituents on adjacent atoms of the aryl or heteroaryl ring may optionally be replaced with a substituent of the formula —$(CRR')_s$—X'—$(C''R''')_d$—, where s and d are independently integers of from 0 to 3, and X' is —O—, —NR'—, —S—, —S(O)—, —$S(O)_2$—, or $S(O)_2$ NR'—. The substituents R, R', R'' and R''' are preferably independently selected from hydrogen, substituted or unsubstituted alkyl, substituted or unsubstituted cycloalkyl, substituted or unsubstituted heterocycloalkyl, substituted or unsubstituted aryl, and substituted or unsubstituted heteroaryl.

As used herein, the term "heteroatom" or "ring heteroatom" is meant to include oxygen (O), nitrogen (N), sulfur (S), phosphorus (P), and silicon (Si).

A "substituent group," as used herein, means a group selected from the following moieties:

(A) —OH, —$NH_2$, —SH, —CN, —$CF_3$, —$NO_2$, oxo, halogen, unsubstituted alkyl, unsubstituted heteroalkyl, unsubstituted cycloalkyl, unsubstituted heterocycloalkyl, unsubstituted aryl, unsubstituted heteroaryl, and (B) alkyl, heteroalkyl, cycloalkyl, heterocycloalkyl, aryl, and heteroaryl, substituted with at least one substituent selected from:

(i) oxo, —OH, —$NH_2$, —SH, —CN, —$CF_3$, —$NO_2$, halogen, unsubstituted alkyl, unsubstituted heteroalkyl, unsubstituted cycloalkyl, unsubstituted heterocycloalkyl, unsubstituted aryl, unsubstituted heteroaryl, and (ii) alkyl, heteroalkyl, cycloalkyl, heterocycloalkyl, aryl, and heteroaryl, substituted with at least one substituent selected from:

(a) oxo, —OH, —$NH_2$, —SH, —CN, —$CF_3$, —$NO_2$, halogen, unsubstituted alkyl, unsubstituted heteroalkyl, unsubstituted cycloalkyl, unsubstituted heterocycloalkyl, unsubstituted aryl, unsubstituted heteroaryl, and (b) alkyl, heteroalkyl, cycloalkyl, heterocycloalkyl, aryl, or heteroaryl, substituted with at least one substituent selected from oxo, —OH, —$NH_2$, —SH, —CN, —$CF_3$, —$NO_2$, halogen, unsubstituted alkyl, unsubstituted heteroalkyl, unsubstituted cycloalkyl, unsubstituted heterocycloalkyl, unsubstituted aryl, and unsubstituted heteroaryl.

A "size-limited substituent" or "size-limited substituent group," as used herein means a group selected from all of the substituents described above for a "substituent group," wherein each substituted or unsubstituted alkyl is a substituted or unsubstituted $C_1$-$C_{20}$ alkyl, each substituted or unsubstituted heteroalkyl is a substituted or unsubstituted 2 to 20 membered heteroalkyl, each substituted or unsubstituted cycloalkyl is a substituted or unsubstituted $C_4$-$C_8$ cycloalkyl, and each substituted or unsubstituted heterocycloalkyl is a substituted or unsubstituted 4 to 8 membered heterocycloalkyl.

A "lower substituent" or "lower substituent group," as used herein means a group selected from all of the substituents described above for a "substituent group," wherein each substituted or unsubstituted alkyl is a substituted or unsubstituted $C_1$-$C_8$ alkyl, each substituted or unsubstituted heteroalkyl is a substituted or unsubstituted 2 to 8 membered heteroalkyl, each substituted or unsubstituted cycloalkyl is a substituted or unsubstituted $C_5$-$C_7$ cycloalkyl, and each substituted or unsubstituted heterocycloalkyl is a substituted or unsubstituted 5 to 7 membered heterocycloalkyl.

The term "pharmaceutically acceptable salts" is meant to include salts of the active compounds which are prepared with relatively nontoxic acids or bases, depending on the particular substituents found on the compounds described herein. When compounds disclosed herein contain relatively acidic functionalities, base addition salts can be obtained by contacting the neutral form of such compounds with a sufficient amount of the desired base, either neat or in a suitable inert solvent. Examples of pharmaceutically acceptable base addition salts include sodium, potassium, calcium, ammonium, organic amino, or magnesium salt, or a similar salt. When compounds disclosed herein contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, maleic, malonic, benzoic, succinic, suberic, fumaric, lactic, mandelic, phthalic, benzenesulfonic, p-tolylsulfonic, citric, tartaric, oxalic, methanesulfonic, and the like. Also included are salts of amino acids such as arginate and the like, and salts of organic acids like glucuronic or galactunoric acids and the like (see, for example, Berge et al., "Pharmaceutical Salts", *Journal of Pharmaceutical Science,* 1977, 66, 1-19). Certain specific compounds disclosed herein contain both basic and acidic functionalities that allow the compounds to be converted into either base or acid addition salts.

Thus, the compounds disclosed herein may exist as salts, such as with pharmaceutically acceptable acids. Examples of such salts include hydrochlorides, hydrobromides, sulfates, methanesulfonates, nitrates, maleates, acetates, citrates, fumarates, tartrates (e.g., (+)-tartrates, (−)-tartrates or mixtures thereof including racemic mixtures), succinates, benzoates and salts with amino acids such as glutamic acid. These salts may be prepared by methods known to those skilled in the art.

The neutral forms of the compounds are preferably regenerated by contacting the salt with a base or acid and isolating the parent compound in the conventional manner. The parent form of the compound differs from the various salt forms in certain physical properties, such as solubility in polar solvents.

In addition to salt forms, the compounds disclosed herein can be in a prodrug form. Prodrugs of the compounds described herein are those compounds that readily undergo chemical changes under physiological conditions to provide the compounds disclosed herein. Additionally, prodrugs can be converted to the compounds disclosed herein by chemical or biochemical methods in an ex vivo environment. For example, prodrugs can be slowly converted to the compounds disclosed herein when placed in a transdermal patch reservoir with a suitable enzyme or chemical reagent.

Certain compounds disclosed herein can exist in unsolvated forms as well as solvated forms, including hydrated forms. In general, the solvated forms are equivalent to unsolvated forms and are encompassed within the scope disclosed herein. Certain compounds disclosed herein may exist in multiple crystalline or amorphous forms. In general, all physical forms are equivalent for the uses contemplated disclosed herein.

Certain compounds disclosed herein possess asymmetric carbon atoms (optical centers) or double bonds; the racemates, diastereomers, tautomers, geometric isomers and individual isomers. The compounds disclosed herein do not include those which are known in the art to be too unstable to synthesize and/or isolate.

The compounds disclosed herein may also contain unnatural proportions of atomic isotopes at one or more of the atoms that constitute such compounds. For example, the compounds may be radiolabeled with radioactive isotopes, such as for example tritium ($^3$H), iodine-125 ($^{125}$I) or carbon-14 ($^{14}$C). All isotopic variations of the compounds disclosed herein, whether radioactive or not, are encompassed within the scope of the disclosure.

Where a substituent of a compound provided herein is "R-substituted" (e.g. $R^1$-substituted), it is meant that the substituent is substituted with one or more of the named R groups (e.g. $R^1$) as appropriate. In some embodiments, the substituent is substituted with only one of the named R groups.

The terms "treating" or "treatment" refers to any indicia of success in the treatment or amelioration of an injury, pathology or condition, including any objective or subjective parameter such as abatement; remission; diminishing of symptoms or making the injury, pathology or condition more tolerable to the patient; slowing in the rate of degeneration or decline; making the final point of degeneration less debilitating; improving a patient's physical or mental well-being. The treatment or amelioration of symptoms can be based on objective or subjective parameters; including the results of a physical examination, neuropsychiatric exams, and/or a psychiatric evaluation. For example, the certain methods presented herein successfully treat cancer by decreasing the incidence of cancer, in inhibiting its growth and or causing remission of cancer.

An "effective amount" is an amount of a compound described herein sufficient to contribute to the treatment, prevention, or reduction of a symptom or symptoms of a disease, or to inhibit effects of an amyloid relative to the absence of the compound. Where recited in reference to a disease treatment, an "effective amount" may also be referred to as a "therapeutically effective amount." A "reduction" of a symptom or symptoms (and grammatical equivalents of this phrase) means decreasing of the severity or frequency of the symptom(s), or elimination of the symptom(s). A "prophylactically effective amount" of a drug is an amount of a drug that, when administered to a subject, will have the intended prophylactic effect, e.g., preventing or delaying the onset (or reoccurrence) a disease, or reducing the likelihood of the onset (or reoccurrence) of a disease or its symptoms. The full prophylactic effect does not necessarily occur by administration of one dose, and may occur only after administration of a series of doses. Thus, a prophylactically effective amount may be administered in one or more administrations. An "activity decreasing amount," as used herein, refers to an amount of antagonist required to decrease the activity of an enzyme relative to the absence of the antagonist. A "function disrupting amount," as used herein, refers to the amount of antagonist required to disrupt the function of an osteoclast or leukocyte relative to the absence of the antagonist.

II. Amyloid Binding Compounds

In one aspect, compounds that associate with an amyloid (or amyloids) and/or an amyloid peptide (or amyloid peptides) are provided. In some embodiments, the compound has the structure of Formula (I), (I)

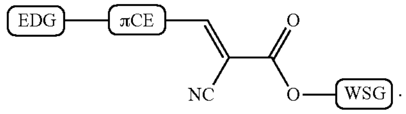

In Formula I, "EDG" is an electron donor group. "πCE" is a π-conjugation element. "WSG" is a water soluble group.

In some embodiments, EDG is substituted or unsubstituted alkyl, substituted or unsubstituted cycloalkyl, substituted or unsubstituted heteroalkyl, substituted or unsubstituted heterocycloalkyl, substituted or unsubstituted aryl, substituted or unsubstituted heteroaryl, —$OR^2$, —$NR^4C(O)R^3$, —$CONR^4R^5$, —$NR^4R^5$, —$SR^6$, or —$PR^7R^8$. In some embodiments, EDG is substituted alkyl, substituted cycloalkyl, substituted heteroalkyl, substituted heterocycloalkyl, substituted aryl, substituted heteroaryl, —$OR^2$, —$NR^4C(O)R^3$, —$CONR^4R^5$, —$NR^4R^5$, —$SR^6$, or —$PR^7R^8$. In some embodiments, EDG is $R^1$-substituted or unsubstituted alkyl, $R^1$-substituted or unsubstituted cycloalkyl, $R^1$-substituted or unsubstituted heteroalkyl, $R^1$-substituted or unsubstituted heterocycloalkyl, $R^1$-substituted or unsubstituted aryl, $R^1$-substituted or unsubstituted heteroaryl, —$OR^2$, —$NR^4C(O)R^3$, —$CONR^4R^5$, —$NR^4R^5$, —$SR^6$, or —$PR^7R^8$. In some embodiments, EDG is $R^1$-substituted alkyl, $R^1$-substituted cycloalkyl, $R^1$-substituted heteroalkyl, $R^1$-substituted heterocycloalkyl, $R^1$-substituted aryl, $R^1$-substituted heteroaryl, —$OR^2$, —$NR^4C(O)R^3$, —$CONR^4R^5$, —$NR^4R^5$, —$SR^6$, or —$PR^7R^8$.

In some embodiments, $R^1$ is halogen, —CN, —$OR^9$, —$CONR^{10}R^{11}$, —$NR^{10}R^{11}$, —$SR^9$, —$SOR^9$, —$SO_2R^9$, —$COR^9$, —$COOR^9$, —$NR^{10}COR^9$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. In some embodiments, $R^1$ is halogen, —CN, —$OR^9$, —$CONR^{10}R^{11}$, —$NR^{10}R^{11}$, —$SR^9$, —$SOR^9$, —$SO_2R^9$, —$COR^9$, —$COOR^9$, —$NR^{10}COR^9$, $R^{12a}$-substituted or unsubstituted alkyl, $R^{12a}$-substituted or unsubstituted heteroalkyl, $R^{12a}$-substituted or unsubstituted cycloalkyl, $R^{12a}$-substituted or unsubstituted heterocycloalkyl, $R^{12a}$-substituted or unsubstituted aryl, or $R^{12a}$-substituted or unsubstituted heteroaryl. In some embodiments, $R^1$ is halogen, —$OR^9$, —$NR^{10}R^{11}$, unsubstituted alkyl, unsubstituted heteroalkyl, unsubstituted cycloalkyl, unsubstituted heterocycloalkyl, unsubstituted aryl, or unsubstituted heteroaryl. In some embodiments, $R^1$ is —$OR^9$, —$NR^{10}R^{11}$, unsubstituted alkyl, unsubstituted heteroalkyl, unsubstituted cycloalkyl, unsubstituted heterocycloalkyl, unsubstituted aryl, or unsubstituted heteroaryl. In some embodiments, when $R^1$ is attached to alkyl, cycloalkyl, or aryl, $R^1$ includes at least one heteroatom. In some embodiments, $R^1$ includes at least one heteroatom. In some embodiments, $R^1$ is —$OR^9$ or —$NR^{10}R^{11}$. In some embodiments, $R^1$ is —$NR^{10}R^{11}$.

In certain embodiments, $R^2$, $R^3$, $R^4$, $R^5$, $R^6$, $R^7$ and $R^8$ are independently hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. In certain embodiments, $R^2$, $R^3$, $R^4$, $R^5$, $R^6$, $R^7$ and $R^8$ are independently hydrogen, $R^{12}$-substituted or unsubstituted alkyl, $R^{12}$-substituted or unsubstituted heteroalkyl, $R^{12}$-substituted or unsubstituted cycloalkyl, $R^{12}$-substituted or unsubstituted heterocycloalkyl, $R^{12}$-substituted or unsubstituted aryl or $R^{12}$-substituted or unsubstituted heteroaryl. In some embodiments, $R^4$ and $R^5$ are optionally joined together to form a substituted or unsubstituted heterocycloalkyl, or substituted or unsubstituted heteroaryl. In some embodiments, $R^4$ and $R^5$ are optionally joined together to form $R^{12}$-substituted or unsubstituted heterocycloalkyl, or $R^{12}$-substituted or unsubstituted heteroaryl.

In some embodiments, $R^9$, $R^{10}$ and $R^{11}$ are independently hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. In some embodiments, $R^9$, $R^{19}$ and $R^{11}$ are independently hydrogen, $R^{12}$-substituted or unsubstituted alkyl, $R^{12}$-substituted or unsubstituted heteroalkyl, $R^{12}$-substituted or unsubstituted cycloalkyl, $R^{12}$-substituted or unsubstituted heterocycloalkyl, $R^{12}$-substituted or unsubstituted aryl, or $R^{12}$-substituted or unsubstituted heteroaryl. In certain embodiments, $R^{10}$ and $R^{11}$ are optionally joined together to form an substituted or unsubstituted heterocycloalkyl, or substituted or unsubstituted heteroaryl. In certain embodiments, $R^{10}$ and $R^{11}$ are optionally joined together to form an $R^{12}$-substituted or unsubstituted heterocycloalkyl, or $R^{12}$-substituted or unsubstituted heteroaryl.

$R^{12}$ and $R^{12a}$ are independently halogen, —CN, —$SR^{13}$, —$SOR^{13}$, —$SO_2R^{13}$, —$OR^{13}$, —$NR^{14}R^{15}$, —$COR^{15}$, —$COOR^{15}$, $CONR^{14}R^{15}$, —$NR^{14}COR^{15}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. In some embodiments, $R^{12}$ and $R^{12a}$ are independently halogen, —CN, —$SR^{13}$, —$SOR^{13}$, —$SO_2R^{13}$, —$OR^{13}$, —$NR^{14}R^{15}$, —$COR^{15}$, —$COOR^{15}$, $CON^{14}R^{15}$, —$NR^{14}COR^{15}$, $R^{16}$-substituted or unsubstituted alkyl, $R^{16}$-substituted or unsubstituted heteroalkyl, $R^{16}$-substituted or unsubstituted cycloalkyl, $R^{16}$-substituted or unsubstituted heterocycloalkyl, $R^{16}$-substituted or unsubstituted aryl, or $R^{16}$-substituted or unsubstituted heteroaryl. In some embodiments, $R^{12}$ is —$OR^{13}$, —$NR^{14}R^{15}$, $R^{16}$-substituted or unsubstituted alkyl, $R^{16}$-substituted or unsubstituted heteroalkyl, $R^{16}$-substituted or unsubstituted cycloalkyl, $R^{16}$-substituted or unsubstituted heterocycloalkyl, $R^{16}$-substituted or unsubstituted aryl, or $R^{16}$-substituted or unsubstituted heteroaryl.

$R^{13}$, $R^{14}$ and $R^{15}$ are independently hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. In some embodiments, $R^{13}$, $R^{14}$ and $R^{15}$ are independently hydrogen $R^{16}$-substituted or unsubstituted alkyl, $R^{16}$-substituted or unsubstituted heteroalkyl, $R^{16}$-substituted or unsubstituted cycloalkyl, $R^{16}$-substituted or unsubstituted heterocycloalkyl, $R^{16}$-substituted or unsubstituted aryl, or $R^{16}$-substituted or unsubstituted heteroaryl. In some embodiments, $R^{13}$, $R^{14}$, and $R^{15}$ are independently hydrogen, unsubstituted alkyl, unsubstituted heteroalkyl, unsubstituted cycloalkyl, unsubstituted aryl or unsubstituted heteroaryl. In some embodiments, $R^{13}$, $R^{14}$ and $R^{15}$ are independently hydrogen or unsubstituted alkyl.

$R^{16}$ is halogen, —$NH_2$, —OH, —SH, —COOH, —COH, unsubstituted alkyl, unsubstituted heteroalkyl, unsubstituted cycloalkyl, unsubstituted heterocycloalkyl, unsubstituted aryl, or unsubstituted heteroaryl.

In some embodiments, $R^{12}$ is —$OR^{13}$ or —$NR^{14}R^{15}$. In some embodiments, $R^{12a}$ is —$OR^{13}$ or —$NR^{14}R^{15}$. In some embodiments, where $R^{12a}$ forms part of an $R^1$ substituent (e.g. where $R^1$ is an alkyl, cycloalkyl or aryl), $R^{12a}$ includes a heteroatom. In some embodiments, where $R^{12a}$ forms part of an $R^1$ substituent (e.g. where $R^1$ is an alkyl, cycloalkyl or aryl), $R^{12a}$ is —$OR^{13}$ or —$NR^{14}R^{15}$.

In some embodiments, $R^4$ and $R^5$ are independently hydrogen or $R^{12}$-substituted or unsubstituted alkyl. In some embodiments, $R^4$ and $R^5$ are independently hydrogen, $R^{12}$-substituted or unsubstituted $C_1$-$C_{20}$ (e.g., $C_1$-$C_{10}$) alkyl, or $R^{12}$-substituted or unsubstituted heteroalkyl. In some embodiments, $R^4$ and $R^5$ are optionally joined together to form an $R^{12}$-substituted or unsubstituted heterocycloalkyl. The $R^{12}$-substituted or unsubstituted heterocycloalkyl can be $R^{12}$-substituted or unsubstituted piperidinyl, $R^{12}$-substituted or unsubstituted morpholinyl, $R^{12}$-substituted or unsubstituted tetrahydrofuranyl, $R^{12}$-substituted or unsubstituted tetrahydrothienyl, or $R^{12}$-substituted or unsubstituted piperazinyl. In some embodiments, $R^{12}$ is $R^{16}$-substituted or unsubstituted $C_1$-$C_{20}$ (e.g., $C_1$-$C_{10}$) alkyl or $R^{16}$-substituted or unsubstituted heteroalkyl. $R^{16}$ can be unsubstituted $C_4$-$C_8$ heterocycloalkyl.

In some embodiments, $R^4$ and $R^5$ are joined together to form $R^{12}$-substituted or unsubstituted heteroaryl. The $R^{12}$-substituted or unsubstituted heteroaryl can be $R^{12}$-substituted or unsubstituted purinyl, $R^{12}$-substituted or unsubstituted pyrimidinyl, $R^{12}$-substituted or unsubstituted imidazolyl, $R^{12}$-substituted or unsubstituted pyrrolopyridinyl (e.g., 1H-pyrrolo[2,3-b]pyridinyl), $R^{12}$-substituted or unsubstituted pyrimidinyl, $R^{12}$-substituted or unsubstituted indazolyl (e.g., 1H-indazolyl), or $R^{12}$-substituted or unsubstituted pyrrolopyrimidinyl (e.g., 7H-pyrrolo[2,3-d]pyrimidinyl). In some embodiments, $R^4$ and $R^5$ are joined together to form $R^{12}$-substituted or unsubstituted pyrrolopyrimidinyl, $R^{12}$-substituted or unsubstituted indolyl, $R^{12}$-substituted or unsubstituted pyrazolyl, $R^{12}$-substituted or unsubstituted indazolyl, $R^{12}$-substituted or unsubstituted imidazolyl, $R^{12}$-substituted or unsubstituted thiazolyl, $R^{12}$-substituted or unsubstituted benzothiazolyl, $R^{12}$-substituted or unsubstituted oxazolyl, $R^{12}$-substituted or unsubstituted benzimidazolyl, $R^{12}$-substituted or unsubstituted benzoxazolyl, $R^{12}$-substituted or unsubstituted isoxazolyl, $R^{12}$-substituted or unsubstituted benzisoxazolyl, $R^{12}$-substituted or unsubstituted triazolyl, $R^{12}$-substituted or unsubstituted benzotriazolyl, $R^{12}$-substituted or unsubstituted quinolinyl, $R^{12}$-substituted or unsubstituted isoquinolinyl, $R^{12}$-substituted or unsubstituted quinazolinyl, $R^{12}$-substituted or unsubstituted pyrimidinyl, $R^{12}$-substituted or unsubstituted pyridinyl N-oxide, $R^{12}$-substituted or unsubstituted furanyl, $R^{12}$-substituted or unsubstituted thiophenyl, $R^{12}$-substituted or unsubstituted benzofuranyl, $R^{12}$-substituted or unsubstituted benzothiophenyl, $R^{12}$-substituted or unsubstituted imidazopyridazinyl (e.g., imidazo[1,2b]pyridazinyl). In some embodiments, $R^4$ and $R^5$ are joined together to form $R^{12}$-substituted or unsubstituted 6,5 fused ring heteroaryl, $R^{12}$-substituted or unsubstituted 5,6 fused ring heteroaryl, $R^{12}$-substituted or unsubstituted 5,5 fused ring heteroaryl, or $R^{12}$-substituted or unsubstituted 6,6 fused ring heteroaryl. In other embodiments, $R^4$ and $R^5$ are joined together to form a $R^{12}$-substituted or unsubstituted 5 or 6 membered heteroaryl having at least 2 (e.g. 2 to 4) ring nitrogens.

In some embodiments, the pi-conjugation element has the formula: $-L^1-(A^1)_q-L^2-(A^2)_r-L^3-$ or $-L^1-(A^1)_q-L^4-A^3-L^2-(A^2)_r-L^3-$. $L^1$, $L^2$, $L^3$ and $L^4$ are independently a bond or a linking group having the formula:

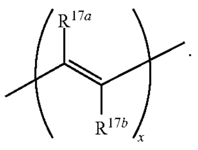

In the formula above, the symbol x is an integer from 1 to 50. In some embodiments, x is an integer from 1 to 10, from 1 to 20, from 1 to 30, or from 1 to 40. In some embodiments, x is an integer from 1 to 3. In some embodiments, x is an integer of 1. $R^{17a}$ and $R^{17b}$ are independently hydrogen, halogen, —CN, —$OR^{18}$, —$CONR^{19}R^{20}$, —$NR^{19}R^{20}$, —$SR^{18}$, —$SOR^{18}$, —$SO_2R^{18}$, —$COR^{18}$, —$COOR^{18}$, —$NR^{19}COR^{20}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. In some embodiments, $R^{17a}$ and $R^{17b}$ are independently hydrogen, halogen, —CN, —$OR^{18}$, —$CONR^{19}R^{20}$, —$NR^{19}R^{20}$, —$SR^{18}$, —$SOR^{18}$, —$SO_2R^{18}$, —$COR^{18}$, —$COOR^{18}$, —$NR^{19}COR^{20}$, $R^{21}$-substituted or unsubstituted alkyl, $R^{21}$-substituted or unsubstituted heteroalkyl, $R^{21}$-substituted or unsubstituted cycloalkyl, $R^{21}$-substituted or unsubstituted heterocycloalkyl, $R^{21}$-substituted or unsubstituted aryl, or $R^{21}$-substituted or unsubstituted heteroaryl.

$A^1$, $A^2$ and $A^3$ are independently substituted or unsubstituted arylene or substituted or unsubstituted heteroarylene. In some embodiments, $A^1$, $A^2$ and $A^3$ are independently $R^{17}$-substituted or unsubstituted arylene or $R^{17}$-substituted or unsubstituted heteroarylene. The symbols q and r are independently 0 or 1.

In some embodiments, the pi-conjugation element has the formula: $-L^1-(A^1)_q-L^2-(A^2)_r-L^3-$. In certain embodiments, $L^1$ and $L^3$ are bonds, $L^2$ is a linking group (as defined above or below), $A^1$ and $A^2$ are substituted or unsubstituted arylene, or substituted or unsubstituted heteroarylene, and q and r are 1. In certain embodiments, $L^1$ and $L^3$ are bonds, $L^2$ is a linking group (as defined above or below), $A^1$ and $A^2$ are $R^{17}$-substituted or unsubstituted arylene, or $R^{17}$-substituted or unsubstituted heteroarylene, and q and r are 1. In some embodiments, $L^1$, $L^2$ and $L^3$ are bonds, $A^1$ and $A^2$ are $R^{17}$-substituted or unsubstituted arylene or $R^{17}$-substituted or unsubstituted heteroarylene, and q is 1 and r is 0.

In some embodiments, the pi-conjugation element has the formula: $-L^1-(A^1)_q-L^4-A^3-L^2-(A^2)_r-L^3-$. In some embodiments, $L^1$ and $L^3$ are bonds, $L^2$ and $L^4$ are linking groups (as defined above or below), $A^1$, $A^2$ and $A^3$ are substituted or unsubstituted arylene, or substituted or unsubstituted heteroarylene, and q and r are 1. In some embodiments, $L^1$ and $L^3$ are bonds, $L^2$ and $L^4$ are linking groups (as defined above or below), $A^1$, $A^2$ and $A^3$ are $R^{17}$-substituted or unsubstituted arylene or $R^{17}$-substituted or unsubstituted heteroarylene, and q and r are 1. In some embodiments, the pi-conjugation element is substituted or unsubstituted arylene or substituted or unsubstituted heteroarylene. In some embodiments, the pi-conjugation element is $R^{17}$-substituted or unsubstituted arylene or $R^{17}$-substituted or unsubstituted heteroarylene. In certain embodiments, the pi-conjugation element is substituted or unsubstituted phenylene or substituted or unsubstituted naphthylene. In certain embodiments, the pi-conjugation element is $R^{17}$-substituted or unsubstituted phenylene or $R^{17}$-substituted or unsubstituted naphthylene.

In certain embodiments, compounds disclosed herein can exhibit increased fluorescence when bound to amyloids. In certain embodiments, the pi-conjugation element is in a planar or substantially planar orientation when bound to an amyloid. In some embodiments, negative charge donated from EDG can enhance the fluorescent properties of the compounds herein and improve detection of amyloids (e.g., a amyloid plaque).

In some embodiments, a linking group ($L^1$, $L^2$, $L^3$ and $L^4$) has the formula:

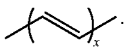

The symbol x is an integer from 1 to 50. In some embodiments, x is an integer from 1 to 10, from 1 to 20, from 1 to 30, or from 1 to 40. In some embodiments, x is an integer from 1 to 5, 1 to 3, 2 or 1. In some embodiments, x is an integer from 1 to 3. In some embodiments, x is an integer of 1. In some embodiments, $L^1$, $L^2$, $L^3$ and $L^4$ are independently a bond.

In some embodiments, $A^1$, $A^2$ and $A^3$ are independently substituted or unsubstituted arylene, or substituted or unsubstituted heteroarylene. In some embodiments, $A^1$, $A^2$ and $A^3$ are independently $R^{17}$-substituted or unsubstituted arylene, or $R^{17}$-substituted or unsubstituted heteroarylene. In certain embodiments, q and r are independently 0 or 1. In some embodiments, q is 1 and r is 0. In some embodiments, q is 0 and r is 1. In some embodiments, $A^1$, $A^2$ and $A^3$ are independently substituted or unsubstituted phenylene, or substituted or unsubstituted naphthylene. In some embodiments, $A^1$, $A^2$ and $A^3$ are independently $R^{17}$-substituted or unsubstituted phenylene, or $R^{17}$-substituted or unsubstituted naphthylene. In some embodiments, $A^1$, $A^2$ and $A^3$ are independently $R^{17}$-substituted or unsubstituted phenylene. In some embodiments, $A^1$, $A^2$ and $A^3$ are independently substituted or unsubstituted phenylene. In some embodiments, $A^1$, $A^2$ and $A^3$ are independently substituted or unsubstituted naphthylene. In some embodiments, $A^1$, $A^2$ and $A^3$ are independently $R^{17}$-substituted or unsubstituted naphthylene.

In some embodiments, $R^{17}$ is independently halogen, —CN, —$OR^{18}$, —$CONR^{19}R^{20}$, —$NR^{19}R^{20}$, —$SR^{18}$, —$SOR^{18}$, —$SO_2R^{18}$, —$COR^{18}$, —$COOR^{18}$, —$NR^{19}COR^{20}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. In some embodiments, $R^{17}$ is independently halogen, —CN, —$OR^{18}$, —$CONR^{19}R^{20}$, —$NR^{19}R^{20}$, —$SR^{18}$, —$SOR^{18}$, —$SO_2R^{18}$, —$COR^{18}$, —$COOR^{18}$, —$NR^{19}COR^{20}$, $R^{21}$-substituted or unsubstituted alkyl, R-$^{21}$substituted or unsubstituted heteroalkyl, $R^{21}$-substituted or unsubstituted cycloalkyl, $R^{21}$-substituted or unsubstituted heterocycloalkyl, $R^{21}$-substituted or unsubstituted aryl, or $R^{21}$-substituted or unsubstituted heteroaryl. In some embodiments, $R^{17}$ is —$OR^{18}$, —$NR^{19}R^{20}$, $R^{21}$-substituted or unsubstituted alkyl, $R^{21}$-substituted or unsubstituted heteroalkyl, $R^{21}$-substituted or unsubstituted cycloalkyl, $R^{21}$-substituted or unsubstituted heterocycloalkyl, $R^{21}$-substituted or unsubstituted aryl, or $R^{21}$-substituted or unsubstituted heteroaryl. In some embodiments, $R^{17}$ is $R^{21}$-substituted or unsubstituted $C_1$-$C_{20}$ (e.g., $C_1$-$C_{10}$) alkyl, or $R^{21}$-substituted or unsubstituted heteroalkyl.

$R^{18}$, $R^{19}$ and $R^{20}$ are independently hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. $R^{18}$, $R^{19}$ and $R^{20}$ are independently hydrogen, $R^{21}$-substituted or unsubstituted alkyl, $R^{21}$-substituted or unsubstituted heteroalkyl, $R^{21}$-substituted or unsubstituted cycloalkyl, $R^{21}$-substituted or unsubstituted heterocycloalkyl, $R^{21}$-substituted or unsubstituted aryl, or $R^{21}$-substituted or unsubstituted heteroaryl. In some embodiments, $R^{21}$ is halogen, —$OR^{22}$, —$NR^{23}R^{24}$, halogen, —CN, —$OR^{22}$, —$CONR^{23}R^{24}$, —$NR^{23}R^{24}$, —$SR^{22}$, —$SOR^{22}$, —$SO_2R^{22}$, —$COR^{22}$, —$COOR^{22}$, —$NR^{23}COR^{24}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. $R^{21}$ can be halogen, —$OR^{22}$, —$NR^{23}R^{24}$, halogen, —CN, —$OR^{22}$, —$CONR^{23}R^{24}$, —$NR^{23}R^{24}$, —$SR^{22}$, —$SOR^{22}$, —$SO_2R^{22}$, —$COR^{22}$, —$COOR^{22}$, —$NR^{23}COR^{24}$, $R^{21a}$-substituted or unsubstituted alkyl, $R^{21a}$-substituted or unsubstituted heteroalkyl, $R^{21a}$-substituted or unsubstituted cycloalkyl, $R^{21a}$-substituted or unsubstituted heterocycloalkyl, $R^{21a}$-substituted or unsubstituted aryl, or $R^{21a}$-substituted or unsubstituted heteroaryl. In some embodiments, $R^{21a}$ is halogen, —$NH_2$, —OH, —SH, —COOH, —COH, unsubstituted alkyl, unsubstituted, heteroalkyl, unsubstituted cycloalkyl, unsubstituted heterocycloalkyl, unsubstituted aryl or unsubstituted heteroaryl. $R^{22}$, $R^{23}$ and $R^{24}$ are independently hydrogen or unsubstituted alkyl, unsubstituted heteroalkyl, unsubstituted cycloalkyl, unsubstituted heterocycloalkyl, unsubstituted aryl or unsubstituted heteroaryl. In some embodiments, $R^{22}$, $R^{23}$ and $R^{24}$ are independently hydrogen or unsubstituted alkyl.

In some embodiments, the water soluble group is substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. In some embodiments, the water soluble group is substituted alkyl, substituted heteroalkyl, substituted cycloalkyl, substituted heterocycloalkyl, substituted aryl, or substituted heteroaryl. In some embodiments, the water soluble group is $R^{25}$-substituted or unsubstituted alkyl, $R^{25}$-substituted or unsubstituted heteroalkyl, $R^{25}$-substituted or unsubstituted cycloalkyl, $R^{25}$-substituted or unsubstituted heterocycloalkyl, $R^{25}$-substituted or unsubstituted aryl, $R^{25}$-substituted or unsubstituted heteroaryl. In some embodiments, the water soluble group is $R^{25}$-substituted alkyl, $R^{25}$-substituted heteroalkyl, $R^{25}$-substituted cycloalkyl, $R^{25}$-substituted heterocycloalkyl, $R^{25}$-substituted aryl, $R^{25}$-substituted heteroaryl.

$R^{25}$ is halogen, —CN, —$OR^{26}$, —$CONR^{27}R^{28}$, —$NR^{27}R^{28}$, —$SR^{26}$, —$SOR^{26}$, —$SO_2R^{26}$, —$COR^{26}$, —$COOR^{26}$, —$NR^{27}COR^{28}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. In some embodiments, $R^{25}$ is halogen, —CN, —$OR^{26}$, —$CONR^{27}R^{28}$, —$NR^{27}R^{28}$, —$SR^{26}$, —$SOR^{26}$, —$SO_2R^{26}$, —$COR^{26}$, —$COOR^{26}$, —$NR^{27}COR^{28}$, $R^{29}$-substituted or unsubstituted alkyl, $R^{29}$-substituted or unsubstituted heteroalkyl, $R^{29}$-substituted or unsubstituted cycloalkyl, $R^{29}$-substituted or unsubstituted heterocycloalkyl, $R^{29}$-substituted or unsubstituted aryl, or $R^{29}$-substituted or unsubstituted heteroaryl. In some embodiments, $R^{26}$, $R^{27}$ and $R^{28}$ are independently hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. In some embodiments, $R^{26}$, $R^{27}$ and $R^{28}$ are independently hydrogen, $R^{29}$-substituted or unsubstituted alkyl, $R^{29}$-substituted or unsubstituted heteroalkyl, $R^{29}$-substituted or unsubstituted cycloalkyl, $R^{29}$-substituted or unsubstituted heterocycloalkyl, $R^{29}$-substituted or unsubstituted aryl, or $R^{29}$-substituted or unsubstituted heteroaryl. In certain embodiments, $R^{27}$ and $R^{28}$ are optionally joined together to form a substituted or unsubstituted heterocycloalkyl, or a substituted or unsubstituted heteroaryl. In certain embodiments, $R^{27}$ and $R^{28}$ are optionally joined together to form a $R^{29}$-substituted or unsubstituted heterocycloalkyl, or a $R^{29}$-substituted or unsubstituted heteroaryl.

$R^{29}$ is halogen, —CN, —$OR^{30}$, —$CONR^{31}R^{32}$, —$NR^{31}R^{32}$, —$SR^{30}$, —$SOR^{30}$, —$SO_2R^{30}$, —$COR^{30}$, —$COOR^{30}$, —$NR^{31}COR^{32}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. In some embodiments, $R^{29}$ is unsubstituted alkyl, unsubstituted heteroalkyl, unsubstituted cycloalkyl, unsubstituted heterocycloalkyl, unsubstituted aryl, or unsubstituted heteroaryl. In some embodiments, $R^{30}$, $R^{31}$ and $R^{32}$ are independently hydrogen or substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. In some embodiments, $R^{30}$, $R^{31}$ and $R^{32}$ are independently hydrogen or unsubstituted alkyl, unsubstituted heteroalkyl, unsubstituted cycloalkyl, unsubstituted heterocycloalkyl, unsubstituted aryl or unsubstituted heteroaryl. In some embodiments, $R^{30}$, $R^{31}$ and $R^{32}$ are independently hydrogen or unsubstituted alkyl.

In some embodiments, the water soluble group can include a moiety that increases the water solubility of a molecule. In some embodiments, the water soluble group can include a moiety containing a heteroatom (e.g., oxygen). In some embodiments, the heteroatom can be oxygen or nitrogen.

In some embodiments, the water soluble group is an ethylene glycol moiety having the formula:

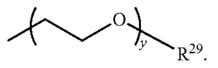

In some embodiments, y is an integer from 1 to 50. In some embodiments, y is an integer from 1 to 10, from 1 to 20, from 1 to 30, or from 1 to 40. In some embodiments, $R^{29}$ is —OMe.

In some embodiments, the water soluble group is $R^{29}$-substituted or unsubstituted $C_1$-$C_{20}$ (e.g., $C_1$-$C_{10}$) alkyl or $R^{29}$-substituted or unsubstituted heteroalkyl. In some embodiments, $R^{29}$ is —OH. In some embodiments, the water soluble group can be $—(CH_2)_b—(CH_2OH)—CH_2OH$, and b is an integer from 0 to 20, or from 0-10.

In some embodiments, the compound has the structure:

(IIa)

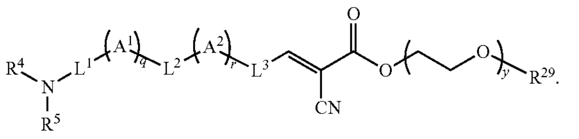

In Formula IIa, q and r are independently 0 or 1, and y is an integer from 1 to 10. $L^1$, $L^2$, $L^3$, $A^1$, $A^2$, $R^4$, $R^5$ and $R^{29}$ are as defined above.

In some embodiments, the compound has the structure:

(IIb)

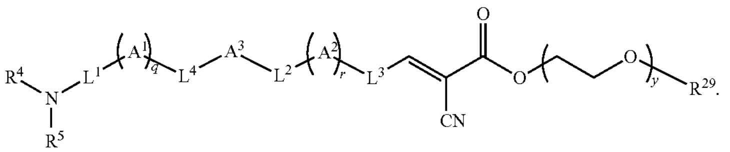

In Formula IIb, q and r are independently 0 or 1, and y is an integer from 1 to 10. $L^1$, $L^2$, $L^3$, $L^4$, $A^1$, $A^2$, $A^3$, $R^4$, $R^5$ and $R^{29}$ are as defined above.

In some embodiments, the compound has the structure:

(IIIa)

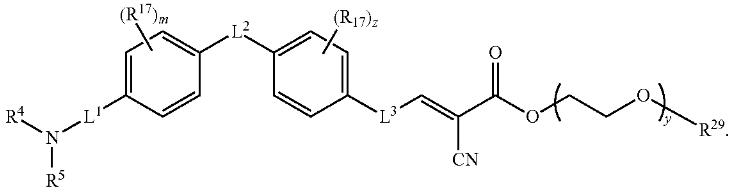

In Formula IIIa, m is an integer from 0 to 4, z is an integer from 0 to 4, and y is an integer from 1 to 10. $L^1$, $L^2$, $L^3$, $R^4$, $R^5$, $R^{17}$ and $R^{29}$ are as defined above.

In some embodiments, the compound has the structure:

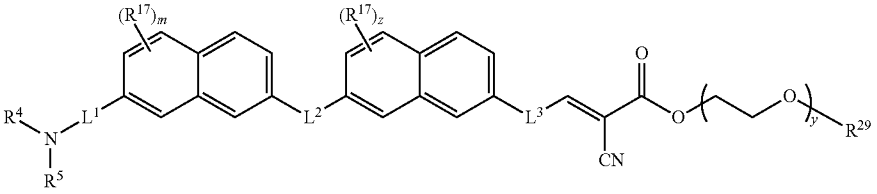

In Formula IIIb, m is an integer from 0 to 6, z is an integer from 0 to 6, and y is an integer from 1 to 10. $L^1$, $L^2$, $L^3$, $R^4$, $R^5$, $R^{17}$ and $R^{29}$ are as defined above. In some embodiments, m is 0. In some embodiments, z is 0. In some embodiments, m is 1. In some embodiments, z is 1.

In some embodiments, the compound has the structure:

(IVa)

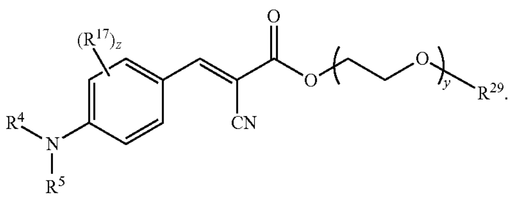

In Formula IVa, y is an integer from 1 to 10, and z is an integer from 0 to 4. $R^4$, $R^5$, $R^{17}$ and $R^{29}$ are as defined above. In some embodiments, $R^{29}$ is —OMe.

In some embodiments, the compound has the structure:

(IVb)

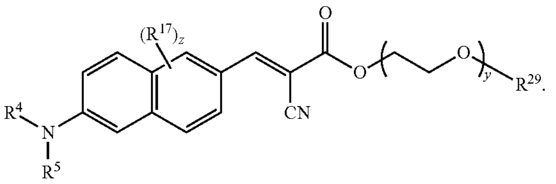

In Formula IVb, y is an integer from 1 to 10, and z is an integer from 0 to 6. $R^4$, $R^5$, $R^{17}$ and $R^{29}$ are as defined above. In some embodiments, $R^{29}$ is —OMe. In some embodiments, m is 0. In some embodiments, z is 0. In some embodiments, m is 1. In some embodiments, z is 1.

In some embodiments, the compound has the structure:

(IVc)

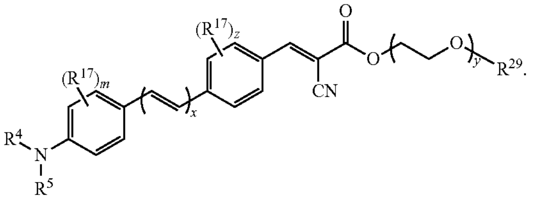

In Formula IVc, m is an integer from 0 to 4, x is an integer from 1 to 10, y is an integer from 1 to 10, and z is an integer from 0 to 4. In some embodiments, x is 1, and m and z are 0. $R^4$, $R^5$, $R^{17}$ and $R^{29}$ are as defined above. In some embodiments, $R^{29}$ is —OMe.

In some embodiments, each substituted group described above in the compounds of the Formulae provided herein is substituted with at least one substituent group. More specifically, in some embodiments, each substituted alkyl, substituted heteroalkyl, substituted cycloalkyl, substituted heterocycloalkyl, substituted aryl, substituted heteroaryl, substituted alkylene, substituted heteroalkylene, substituted or unsubstituted cycloalkylene, substituted or unsubstituted heterocycloalkylene, substituted or unsubstituted arylene, or substituted or unsubstituted heteroarylene described above in the compounds of the Formulae provided herein is substituted with at least one substituent group. In other embodiments, at least one or all of these groups are substituted with at least one size-limited substituent group. Alternatively, at least one or all of these groups are substituted with at least one lower substituent group.

In other embodiments of the compounds of the Formulae provided herein, each substituted or unsubstituted alkyl is a substituted or unsubstituted $C_1$-$C_{20}$ alkyl, each substituted or unsubstituted heteroalkyl is a substituted or unsubstituted 2 to 20 membered heteroalkyl, each substituted or unsubstituted cycloalkyl is a substituted or unsubstituted $C_4$-$C_8$ cycloalkyl, each substituted or unsubstituted heterocycloalkyl is a substituted or unsubstituted 4 to 8 membered heterocycloalkyl, each substituted or unsubstituted alkylene is a substituted or unsubstituted $C_1$-$C_{20}$ alkylene, each substituted or unsubstituted heteroalkylene is a substituted or unsubstituted 2 to 20 membered heteroalkylene, each substituted or unsubstituted cycloalkylene substituted or unsubstituted $C_4$-$C_8$ cycloalkylene, and each substituted or unsubstituted heterocycloalkylene is a substituted or unsubstituted 4 to 8 membered heterocycloalkylene.

Alternatively, each substituted or unsubstituted alkyl is a substituted or unsubstituted $C_1$-$C_8$ alkyl, each substituted or unsubstituted heteroalkyl is a substituted or unsubstituted 2 to 8 membered heteroalkyl, each substituted or unsubstituted cycloalkyl is a substituted or unsubstituted $C_5$-$C_7$ cycloalkyl, each substituted or unsubstituted heterocycloalkyl is a substituted or unsubstituted 5 to 7 membered heterocycloalkyl, each substituted or unsubstituted alkylene is a substituted or unsubstituted $C_1$-$C_8$ alkylene, each substituted or unsubstituted heteroalkylene is a substituted or unsubstituted 2 to 8 membered heteroalkylene, each substituted or unsubstituted cycloalkylene substituted or unsubstituted $C_5$-$C_6$ cycloalkylene, and each substituted or unsubstituted heterocycloalkylene is a substituted or unsubstituted 5 to 7 membered heterocycloalkylene.

In some embodiments, the compounds of the Formulae provided herein are one or more of the compounds set forth in Table 1 below:

TABLE 1

| Compounds. | |
|---|---|
| Cmpd | Structure |
| 8a | 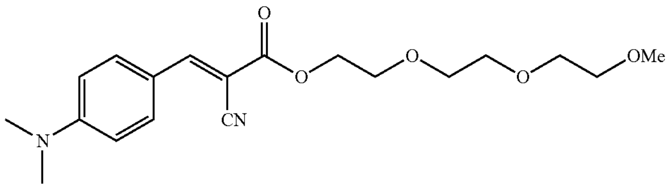 [SMILES: COCCOCCOCCOC(=O)/C(C#N)=C/c1ccc(N(C)C)cc1] |

TABLE 1-continued
| Compounds. | |
|---|---|
| Cmpd | Structure |
| 8b | 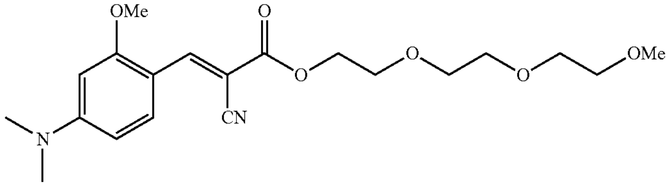 [SMILES: COCCOCCOCCOC(=O)/C(C#N)=C/c1ccc(N(C)C)cc1OC] |
| 8c | 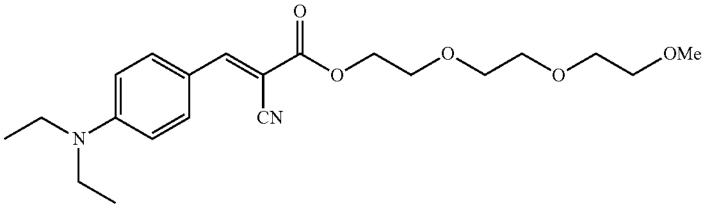 [SMILES: CCN(CC)c1ccc(/C=C(\C#N)C(=O)OCCOCCOCCOC)cc1] |
| 8d | 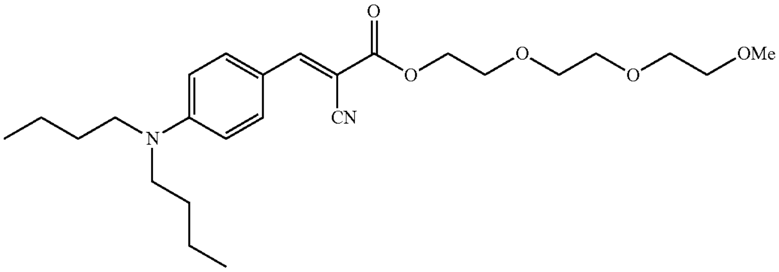 [SMILES: CCCCN(CCCC)c1ccc(/C=C(\C#N)C(=O)OCCOCCOCCOC)cc1] |
| 11 | 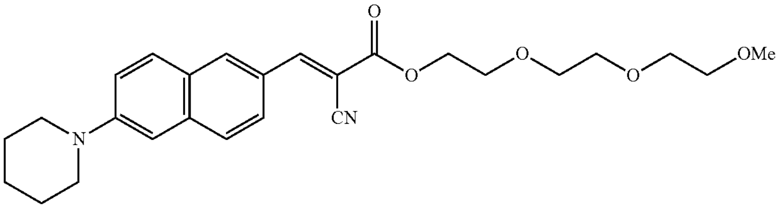 [SMILES: COCCOCCOCCOC(=O)/C(C#N)=C/c1ccc2cc(N3CCCCC3)ccc2c1] |
| 14 | 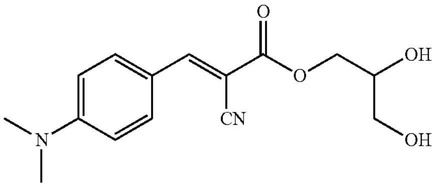 [SMILES: CN(C)c1ccc(/C=C(\C#N)C(=O)OCC(O)CO)cc1] |
| 19 | 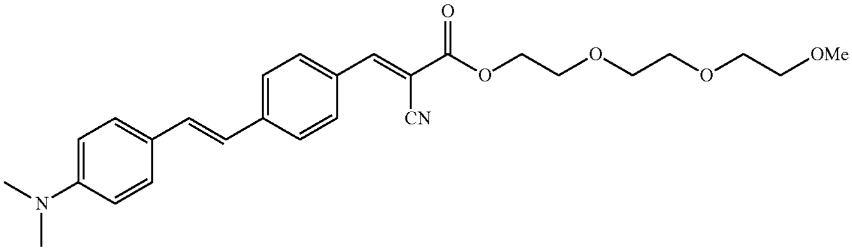 [SMILES: COCCOCCOCCOC(=O)/C(C#N)=C/c1ccc(/C=C/c2ccc(N(C)C)cc2)cc1] |

TABLE 1-continued

| Compounds. | |
|---|---|
| Cmpd | Structure |
| 29 | 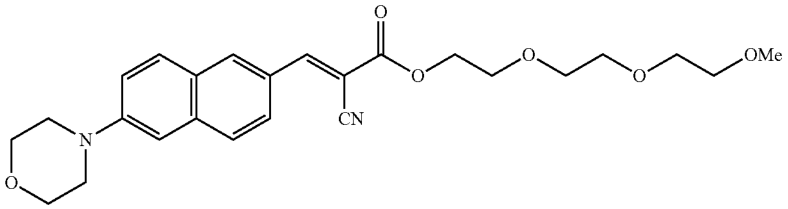 [SMILES: COCCOCCOCCOC(=O)/C(C#N)=C/c1ccc2cc(N3CCOCC3)ccc2c1] |
| 28 | 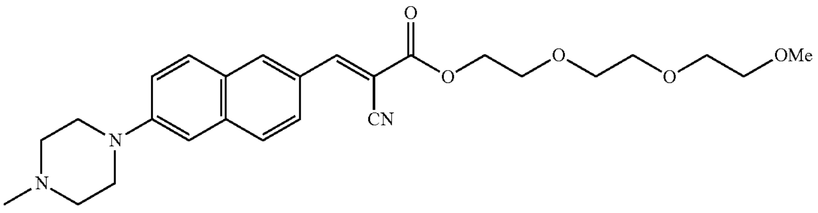 [SMILES: COCCOCCOCCOC(=O)/C(C#N)=C/c1ccc2cc(N3CCN(C)CC3)ccc2c1] |
| 30 | 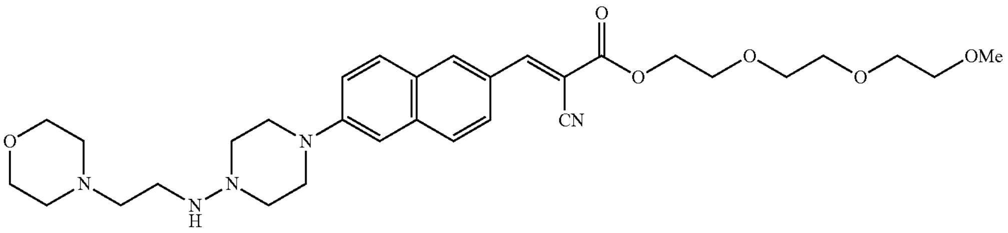 [SMILES: COCCOCCOCCOC(=O)/C(C#N)=C/c1ccc2cc(N3CCN(NCCN4CCOCC4)CC3)ccc2c1] |
| 31 | 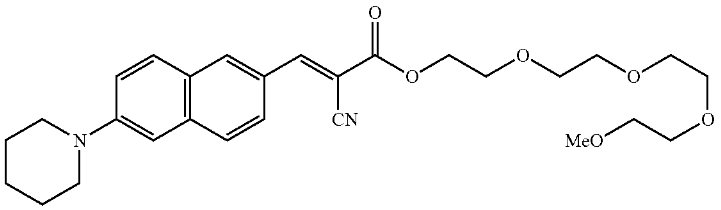 [SMILES: COCCOCCOCCOCCOC(=O)/C(C#N)=C/c1ccc2cc(N3CCCCC3)ccc2c1] |
| 33 | 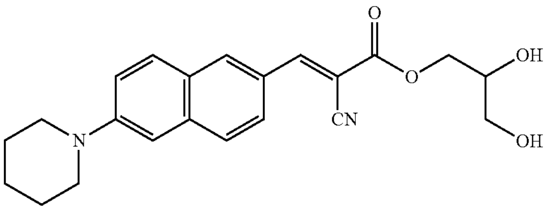 [SMILES: N#C/C(=C\c1ccc2cc(N3CCCCC3)ccc2c1)C(=O)OCC(O)CO] |

III. Pharmaceutical Compositions

In another aspect, pharmaceutical compositions disclosed herein (i.e., formulations) can include a compound described herein in combination with a pharmaceutically acceptable excipient (e.g., carrier). The pharmaceutical compositions include optical isomers, diastereomers, or pharmaceutically acceptable salts of the inhibitors disclosed herein. For example, in some embodiments, the pharmaceutical compositions include a compound disclosed herein and citrate as a pharmaceutically acceptable salt. The compound included in the pharmaceutical composition may be covalently attached to a carrier moiety, as described above. Alternatively, the compound included in the pharmaceutical composition is not covalently linked to a carrier moiety.

A "pharmaceutically acceptable carrier," as used herein refers to pharmaceutical excipients, for example, pharmaceutically, physiologically, acceptable organic or inorganic carrier substances suitable for enteral or parenteral application that do not deleteriously react with the active agent. Suitable pharmaceutically acceptable carriers include water, salt solutions (such as Ringer's solution), alcohols, oils, gelatins, and carbohydrates such as lactose, amylose or starch, fatty acid esters, hydroxymethycellulose, and polyvinyl pyrrolidine. Such preparations can be sterilized and, if desired, mixed with auxiliary agents such as lubricants, preservatives, stabilizers, wetting agents, emulsifiers, salts for influencing osmotic pressure, buffers, coloring, and/or aromatic substances and the like that do not deleteriously react with the compounds disclosed herein.

The compounds disclosed herein can be administered alone or can be coadministered to the subject. Coadministration is meant to include simultaneous or sequential administration of the compounds individually or in combination (more than one compound). The preparations can also be combined, when desired, with other active substances (e.g. to reduce metabolic degradation).

A. Formulations

The compounds can be prepared and administered in a wide variety of oral, parenteral, and topical dosage forms. Thus, the compounds disclosed herein can be administered by injection (e.g. intravenously, intramuscularly, intracutaneously, subcutaneously, intraduodenally, or intraperitoneally). Also, the compounds described herein can be administered by inhalation, for example, intranasally. Additionally, the compounds disclosed herein can be administered transdermally. It is also envisioned that multiple routes of administration (e.g., intramuscular, oral, transdermal) can be used to administer the compounds disclosed herein. Accordingly, pharmaceutical compositions can include a pharmaceutically acceptable carrier or excipient and one or more compounds disclosed herein.

For preparing pharmaceutical compositions from the compounds disclosed herein, pharmaceutically acceptable carriers can be either solid or liquid. Solid form preparations include powders, tablets, pills, capsules, cachets, suppositories, and dispersible granules. A solid carrier can be one or more substance that may also act as diluents, flavoring agents, binders, preservatives, tablet disintegrating agents, or an encapsulating material.

In powders, the carrier is a finely divided solid in a mixture with the finely divided active component. In tablets, the active component is mixed with the carrier having the necessary binding properties in suitable proportions and compacted in the shape and size desired.

The powders and tablets preferably contain from 5% to 70% of the active compound. Suitable carriers are magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. The term "preparation" is intended to include the formulation of the active compound with encapsulating material as a carrier providing a capsule in which the active component with or without other carriers, is surrounded by a carrier, which is thus in association with it. Similarly, cachets and lozenges are included. Tablets, powders, capsules, pills, cachets, and lozenges can be used as solid dosage forms suitable for oral administration.

For preparing suppositories, a low melting wax, such as a mixture of fatty acid glycerides or cocoa butter, is first melted and the active component is dispersed homogeneously therein, as by stirring. The molten homogeneous mixture is then poured into convenient sized molds, allowed to cool, and thereby to solidify.

Liquid form preparations include solutions, suspensions, and emulsions, for example, water or water/propylene glycol solutions. For parenteral injection, liquid preparations can be formulated in solution in aqueous polyethylene glycol solution.

When parenteral application is needed or desired, particularly suitable admixtures for the compounds disclosed herein are injectable, sterile solutions, preferably oily or aqueous solutions, as well as suspensions, emulsions, or implants, including suppositories. In particular, carriers for parenteral administration include aqueous solutions of dextrose, saline, pure water, ethanol, glycerol, propylene glycol, peanut oil, sesame oil, polyoxyethylene-block polymers, and the like. Ampoules are convenient unit dosages. The compounds disclosed herein can also be incorporated into liposomes or administered via transdermal pumps or patches. Pharmaceutical admixtures suitable for use herein include those described, for example, in Pharmaceutical Sciences (17th Ed., Mack Pub. Co., Easton, Pa.) and WO 96/05309, the teachings of both of which are hereby incorporated by reference.

Aqueous solutions suitable for oral use can be prepared by dissolving the active component in water and adding suitable colorants, flavors, stabilizers, and thickening agents as desired. Aqueous suspensions suitable for oral use can be made by dispersing the finely divided active component in water with viscous material, such as natural or synthetic gums, resins, methylcellulose, sodium carboxymethylcellulose, and other well-known suspending agents.

Also included are solid form preparations that are intended to be converted, shortly before use, to liquid form preparations for oral administration. Such liquid forms include solutions, suspensions, and emulsions. These preparations may contain, in addition to the active component, colorants, flavors, stabilizers, buffers, artificial and natural sweeteners, dispersants, thickeners, solubilizing agents, and the like.

The pharmaceutical preparation is preferably in unit dosage form. In such form the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

The quantity of active component in a unit dose preparation may be varied or adjusted from 0.1 mg to 10000 mg, more typically 1.0 mg to 1000 mg, most typically 10 mg to 500 mg, according to the particular application and the potency of the active component. The composition can, if desired, also contain other compatible therapeutic agents.

Some compounds may have limited solubility in water and therefore may require a surfactant or other appropriate co-solvent in the composition. Such co-solvents include: Polysorbate 20, 60, and 80; Pluronic F-68, F-84, and P-103; cyclodextrin; and polyoxyl 35 castor oil. Such co-solvents are typically employed at a level between about 0.01% and about 2% by weight.

Viscosity greater than that of simple aqueous solutions may be desirable to decrease variability in dispensing the formulations, to decrease physical separation of components of a suspension or emulsion of formulation, and/or otherwise to improve the formulation. Such viscosity building agents include, for example, polyvinyl alcohol, polyvinyl pyrrolidone, methyl cellulose, hydroxy propyl methylcellulose, hydroxyethyl cellulose, carboxymethyl cellulose, hydroxy propyl cellulose, chondroitin sulfate and salts thereof, hyaluronic acid and salts thereof, and combinations of the foregoing. Such agents are typically employed at a level between about 0.01% and about 2% by weight.

The compositions disclosed herein may additionally include components to provide sustained release and/or comfort. Such components include high molecular weight, anionic mucomimetic polymers, gelling polysaccharides, and finely-divided drug carrier substrates. These components are discussed in greater detail in U.S. Pat. Nos. 4,911,920; 5,403,841; 5,212,162; and 4,861,760. The entire contents of these patents are incorporated herein by reference in their entirety for all purposes.

B. Effective Dosages

Pharmaceutical compositions provided herein include compositions in which the active ingredient is contained in a therapeutically effective amount, i.e., in an amount effective to achieve its intended purpose. The actual amount effective for a particular application will depend, inter alia, on the condition being treated. For example, when administered in methods to treat cancer, such compositions will contain an amount of active ingredient effective to achieve the desired result (e.g. decreasing the number of cancer cells in a subject).

The dosage and frequency (single or multiple doses) of compound administered can vary depending upon a variety of factors, including route of administration; size, age, sex, health, body weight, body mass index, and diet of the recipient; nature and extent of symptoms of the disease being treated; presence of other diseases or other health-related problems; kind of concurrent treatment; and complications from any disease or treatment regimen. Other therapeutic regimens or agents can be used in conjunction with the methods and compounds disclosed herein.

For any compound described herein, the therapeutically effective amount can be initially determined from cell culture assays, as known in the art.

Therapeutically effective amounts for use in humans may be determined from animal models. For example, a dose for humans can be formulated to achieve a concentration that has been found to be effective in animals.

Dosages may be varied depending upon the requirements of the patient and the compound being employed. The dose administered to a patient should be sufficient to affect a beneficial therapeutic response in the patient over time. The size of the dose also will be determined by the existence, nature, and extent of any adverse side effects. Generally, treatment is initiated with smaller dosages, which are less than the optimum dose of the compound. Thereafter, the dosage is increased by small increments until the optimum effect under circumstances is reached. In one embodiment, the dosage range is 0.001% to 10% w/v. In another embodiment, the dosage range is 0.1% to 5% w/v.

Dosage amounts and intervals can be adjusted individually to provide levels of the administered compound effective for the particular clinical indication being treated. This will provide a therapeutic regimen that is commensurate with the severity of the individual's disease state.

Utilizing the teachings provided herein, an effective prophylactic or therapeutic treatment regimen can be planned that does not cause substantial toxicity and yet is entirely effective to treat the clinical symptoms demonstrated by the particular patient. This planning should involve the careful choice of active compound by considering factors such as compound potency, relative bioavailability, patient body weight, presence and severity of adverse side effects, preferred mode of administration, and the toxicity profile of the selected agent.

C. Toxicity

The ratio between toxicity and therapeutic effect for a particular compound is its therapeutic index and can be expressed as the ratio between $LD_{50}$ (the amount of compound lethal in 50% of the population) and $ED_{50}$ (the amount of compound effective in 50% of the population). Compounds that exhibit high therapeutic indices are preferred. Therapeutic index data obtained from cell culture assays and/or animal studies can be used in formulating a range of dosages for use in humans. The dosage of such compounds preferably lies within a range of plasma concentrations that include the $ED_{50}$ with little or no toxicity. The dosage may vary within this range depending upon the dosage form employed and the route of administration utilized. See, e.g. Fingl et al., In: The Pharmacological Basis of Therapeutics, Ch. 1, p. 1, 1975. The exact formulation, route of administration, and dosage can be chosen by the individual physician in view of the patient's condition and the particular method in which the compound is used.

IV. Methods of Use

In one aspect, there is provided methods of detecting an amyloid peptide and/or amyloid. The methods of detection can employ spectroscopic (i.e., UV-visible, fluorescence, and the like), radiographic, and other detection methods known in the art. In one embodiment, the methods includes contacting a compound as described herein with an amyloid, thereby forming a detectable amyloid complex, and detecting the detectable amyloid complex, as described herein and known in the art. An "amyloid complex" is referred to herein as a complex of a compound described herein and at least one amyloid peptide (e.g., an aggregate of amyloid peptides). The compounds described herein can form a complex with an amyloid by a variety of interactions, such as non-covalent interactions (e.g., hydrophobic interactions or hydrogen bonding).

Amyloids described herein can be composed of at least one amyloid peptide molecule. An amyloid peptide is referred to herein as a peptide or protein that can forms part of or is capable of forming an amyloid in association with other peptides or proteins. Amyloids described herein can be composed of any amyloid peptide or amyloid protein that is known to form amyloids. In some embodiments, amyloids include a plurality of amyloid peptides and/or amyloid peptide molecules. In some embodiments, an amyloid includes an amyloid peptide molecule aggregated with one or more amyloid peptide molecules.

In some embodiments, the amyloid peptides can include Aβ peptide, prion protein, α-synuclein, or superoxide dismutase. In some embodiments, the amyloid peptides can include a portion of or functional fragment thereof of Aβ peptide, prion protein, α-synuclein, or superoxide dismutase. In some embodiments, an amyloid peptide and/or amyloid can be solvated in solution and bound to one or more of the compounds described herein. In some embodiments, the amyloids include amyloid peptides that are arranged in β-sheets that can allow for binding of the compounds described herein. In certain embodiments, the compounds described herein exhibit increased fluorescence (as compared to free solution) when bound and interacting with amyloids via hydrophobic interactions.

In another aspect, the methods provided herein include methods of assaying the compounds herein to detect binding of the compounds to amyloids and/or amyloid peptides. Using techniques known in the art and the guidance provided herein, candidate compounds may be easily assayed for their ability to bind to amyloids. For example, amyloid binding agents having the structure of the Formulae provided herein or embodiments thereof may be assayed using in vitro assays. In some embodiments, in vitro assays can include measuring fluorescence of the compounds herein when they are bound to amyloids versus in free solution not bound to the amyloids. Generally, an increase in fluorescence indicates binding to an amyloid. Binding constants for the compounds herein can also be determined using techniques known in the art. For example, competitive binding studies can be used to determine the effectiveness of the compounds described herein for inhibiting, e.g., IgG-Aβ peptide interactions. Cellular assays may also be used to assess the binding properties of candidate amyloid binding agents having the structure of the Formulae provided herein or embodiments thereof. Cellular assays include cells from any appropriate source, including plant and animal cells (such as mammalian cells). The cellular assays may also be conducted in human cells. The selection of appropriate assay methods is well within the capabilities of those having ordinary skill in the art.

Once compounds are identified that are capable of binding amyloids in vitro and/or in a cell, the compounds may be further tested for their ability to selectively bind amyloid (e.g., in amyloid plaques) in animal models (e.g. whole animals, animal organs, or animal tissues). Thus, the compounds described herein may be further tested in cell models or animal models for their ability to cause detectable changes in phenotype related to a particular amyloid peptide and/or amyloid. In addition to cell cultures, animal models may be used to test the compounds described herein for their ability to treat, for example, diseases associated with amyloids in an animal model. In some embodiments, the compounds described herein can be used to image amyloids in animal tissue. In some embodiments, the animal tissue is human tissue.

In a further aspect, there is provided a method of treating a disease associated with amyloid peptides and/or amyloids in a subject in need of such treatment. In some embodiments, the disease can be characterized by an accumulation of amyloids (e.g., amyloid plaques) in a subject. The methods can include administering to the subject an effective amount (e.g. a therapeutically effective amount) of a compound having the structure of the Formulae provided herein (or an embodiment thereof as described above).

The term "subject" as used herein refers to a mammal to which a pharmaceutical composition or formulation is administered. Exemplary subjects include humans, as well as veterinary and laboratory animals such as horses, pigs, cattle, dogs, cats, rabbits, rats, mice, and aquatic mammals. In some embodiments, the subject is a human.

In some embodiments, the disease can include Alzheimer's disease, bovine spongiform encephalopathy (BSE), Parkinson's disease, Huntington's disease, Down's Syndrome, Dementia with Lewy Body, or Amyotrophic Lateral Sclerosis (ALS). In some embodiments, the amyloid peptide is Aβ peptide and the disease is Alzheimer's disease. In some embodiments, the methods of treating described herein include a method of treating Alzheimer's disease. In some embodiments, the methods of treating described herein include a method of treating Parkinson's disease.

Each patent, published patent application, and reference cited herein is hereby incorporated herein in its entirety and for all purposes.

V. Examples

Example 1

General Procedure for the Preparation of Compounds Described Herein and in Examples 1a-1m.

To a round bottom flask containing a solution of aldehyde (5.0 mmol) and 2-(2-(2-methoxyethoxy) ethoxy)ethyl 2-cyanoacetate (5.5 mmol) in 20 ml of THF was added 0.50 mmol of piperidine and the mixture was heated at 50° C. The reaction was monitored by TLC and was completed within 21 hours. The crude mixture was concentrated under reduced pressure and the product was purified via flash chromatography (10-30% ethyl acetate in hexane).

General Notes:

All the reagents were obtained (Aldrich, Acros) at highest commercial quality and used without further purification except where noted. Air- and moisture-sensitive liquids and solutions were transferred via syringe or stainless steel cannula. Organic solutions were concentrated by rotary evaporation below 45° C. at approximately 20 mmHg. All non-aqueous reactions were carried out under anhydrous conditions. Yields refer to chromatographically and spectroscopically (1H NMR, 13C NMR) homogeneous materials, unless otherwise stated. Reactions were monitored by thin-layer chromatography (TLC) carried out on 0.25 mm E Merck silica gel plates (60E-254) and visualized under UV light and/or developed by dipping in solutions of 10% ethanolic phosphomolybdic acid (PMA) or p-anisaldehyde and applying heat. E. Merck silica gel (60, particle size 0.040-0.063 mm) was used for flash chromatography. Preparative thin-layer chromatography separations were carried out on 0.25 or 0.50 mm E Merck silica gel plates (60E-254). NMR spectra were recorded on Varian Mercury 300 or 400 MHz instruments and calibrated using the residual undeuterated solvent as an internal reference. The following abbreviations were used to explain the multiplicities: s=singlet, d=doublet, t=triplet, q=quartet, m=multiplet, b=broad. High resolution mass spectra (HRMS) were recorded on a VG 7070 HS mass spectrometer under electron spray ionization (ESI) or electron impact (EI) conditions. Fluorescence spectroscopy data were recorded on a MD-5020 Photon Technology International Spectrophotometer at 25° C.

Important to the synthesis of compounds described herein was a Knoevenagel condensation of 1 equivalent of the appropriate aldehyde, e.g. 6, with 1.1 equivalents of the appropriate malonic acid derivative, e.g. 7. See Scheme 1. This reaction was catalyzed by piperidine (10%) and was completed within 21 hours in refluxing THF. See X. H. Chen, Z. J. Zhao, Y. Liu, P. Lu, Y. G. Wang, *Chemistry Letters* 2008, 37:570-571; M. A. Haidekker, T. P. Brady, D. Lichlyter, E. A. Theodorakis, *Journal of the American Chemical Society* 2006, 128:398-399. After a standard chromatographic purification on silica gel, the desired product 8 was isolated in excellent yields (Table 2). Reagents and conditions for Scheme 1: (a) 1.0 equiv 6, 1.1 equiv 7, 0.1 equiv piperidine, THF, 50° C., 21 h.

Scheme 1.

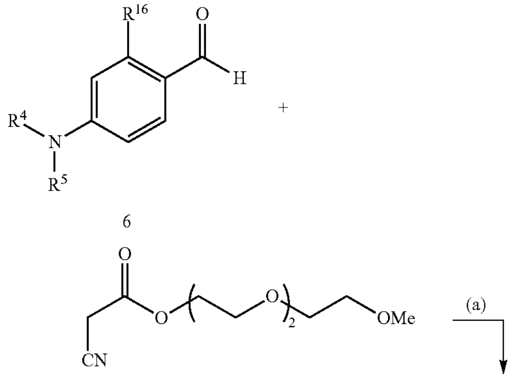

6

7

-continued

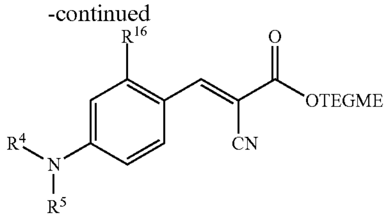

8

TEGME:

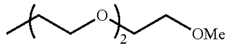

TABLE 2

| Structures and yields for Cmpds 8a-8d. | | | |
|---|---|---|---|
| Comp. No | $R^4$ | $R^5$ | Yield (%) |
| 8a | Me | H | 98 |
| 8b | Me | OMe | 98 |
| 8c | Et | H | 90 |
| 8d | nBu | H | 78 |

Naphthalene-based Cmpd 11 was synthesized by treatment of commercially available methoxy naphthaldehyde 9 with eight equivalents of lithiated piperidine and Knoevenagel condensation of the resulting aldehyde 10 with cyano ester 7 (Scheme 2, 29% combined yield). See H. M. Guo, F. Tanaka, *J. Org. Chem.* 2009, 74:2417-2424. Scheme 2 reagents and conditions: (a) 8.0 equiv piperidine in benzene/HMPA: 1/1, 0° C., 8.0 equiv nBuLi, 0° C., 15 min, then 1.0 equiv 9, 25° C., 12 h, 35%; (b) 1.0 equiv 10, 1.1 equiv 7, 0.1 equiv piperidine, THF, 50° C., 21 h, 82%. In some embodiments, $R^4$, $R^5$ and $R^{16}$ can correspond to the $R^4$, $R^5$ and $R^{16}$ described above.

Scheme 2.

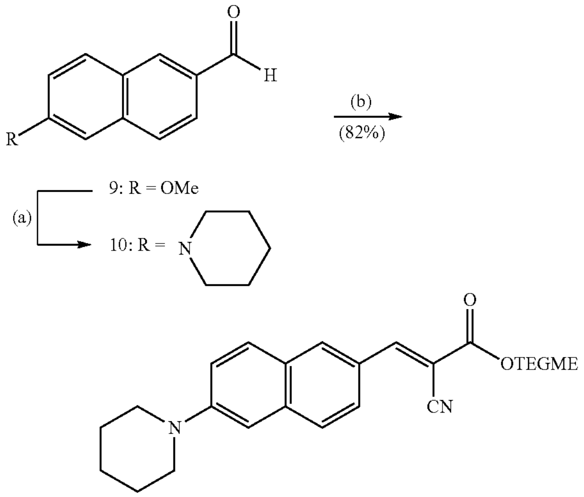

11

Cmpd 14 was prepared by condensation of aldehyde 6a with α-cyano ester 12, followed by an acid-catalyzed deprotection of the acetonide unit (Scheme 3, 68% combined yield). See M. A. Haidekker, T. P. Brady, S. H. Chalian, W. Akers, D. Lichlyter, E. A. Theodorakis, *Bioorg. Chem.* 2004, 32:274-289. Scheme 3 reagents and conditions: (a) 1.0 equiv 6a, 1.1 equiv 12, 0.1 equiv piperidine, THF, 50° C., 21 h, 91%; (b) 1.5 mmol 13, 0.10 g DOWEX-H+, 1:1 THF/MeOH, 25° C., 20 h, 75%.

Scheme 3.

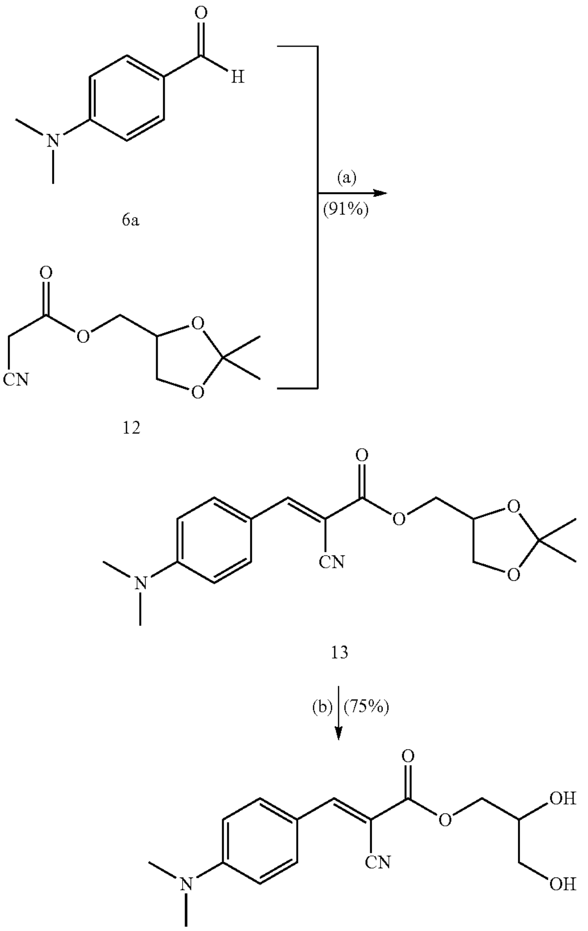

6a, 12, 13, 14

Stilbene-based Cmpd 19 was synthesized in four steps that included: (a) conversion of benzyl bromide 15 to phosphonate 16; (b) Horner-Emmons olefination of 16 with aldehyde 6a to form 17; (c) lithiation of bromide 17 and formylation to produce aldehyde 18; and (d) Knoevenagel condensation of the resulting aldehyde 18 with cyano ester 7 (Scheme 4, 42% combined yield). See H. Meier, E. Karpuk, H. C. Holst, *Eur. J. Org. Chem.* 2006, 2609-2617; L. Viau, O. Maury, H. Le Bozec, *Tetrahedron Lett.* 2004, 45:125-128. Scheme 4 reagents and conditions: (a) 1.0 equiv 15, 15 equiv triethyl phosphite, 90° C., 19 h, 98%; (b) 1.0 equiv 16, 1.0 equiv NaOMe, 1.0 equiv 6a, excess DMF, 25° C., 24 h, 74%; (c) 1.0 equiv 17, 1.0 equiv n-BuLi, 1.33 equiv DMF, THF, −78° C., 60%; (d) 1.0 equiv 18, 1.1 equiv 7, 0.1 equiv piperidine, THF, 50° C., 21 h, 97%. $R^1$ and $R^2$ in Scheme 4 are specific for Scheme 4 and are not intended to correspond to $R^1$ and $R^2$ described above.

Scheme 4.

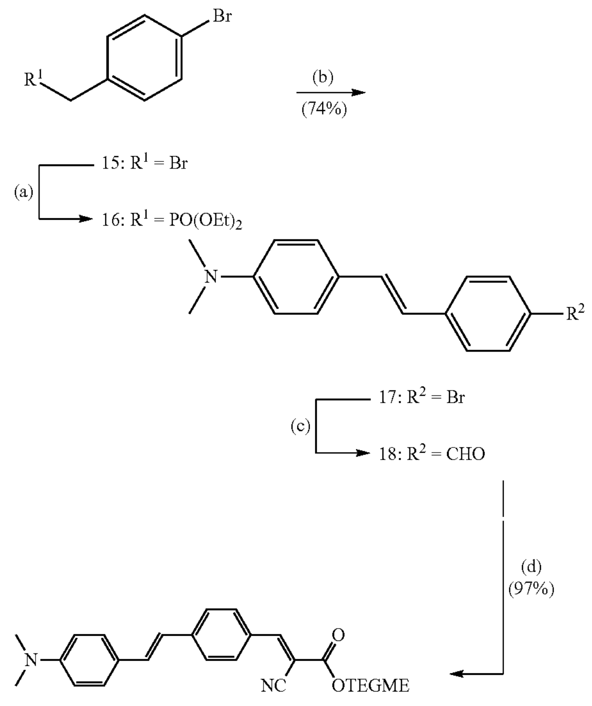

19

Example 1a (E)-2-(2-(2-methoxyethoxyl)ethoxy)ethyl 2-cyano-3-(4-(dimethylamino)phenyl)acrylate (8a)

98%; yellow solid; $^1$H NMR (400 MHz, $CDCl_3$) δ 8.07 (s, 1H), 7.93 (d, 2H, J=9.0 Hz), 6.69 (d, 2H, J=9.1 Hz), 4.41 (m, 2H), 3.81-3.79 (m, 2H), 3.73-3.65 (m, 6H), 3.56-3.54 (m, 2H), 3.37 (s, 3H), 3.10 (s, 6H); $^{13}$C NMR (100 MHz, $CDCl_3$) δ 164.2, 154.7, 153.6, 134.1, 119.3, 117.4, 111.4, 93.6, 71.9, 70.8, 70.6, 70.5, 68.9, 65.0, 59.0, 40.0; HRMS Calc for $C_{19}H_{26}N_2O_5(M)^+$ 362.1836 found 362.1841.

Example 1b (E)-2-(2-(2-methoxyethoxyl)ethoxy)ethyl 2-cyano-3-(4-(dimethylamino)-2-methoxyphenyl)acrylate (8b)

98% yield; yellow solid; $^1$H NMR (400 MHz, $CDCl_3$) δ 8.64 (s, 1H), 8.39 (d, 1H, J=9.2 Hz), 6.63 (dd, 1H, J=2.3 Hz, J=9.2 Hz), 6.01 (s, 1H), 4.40 (m, 2H), 3.87 (s, 3H), 3.81-3.78 (m, 2H), 3.73-3.65 (m, 6H), 3.56-3.53 (m, 2H), 3.36 (s, 3H), 3.10 (s, 6H); $^{13}$C NMR (400 MHz, $CDCl_3$) δ 165.0, 162.2, 155.9, 148.5, 131.3, 118.4, 109.7, 105.4, 93.0, 92.0, 72.2, 71.1, 70.9, 70.8, 69.2, 65.1, 59.3, 55.6, 40.4; HRMS Calc for $C_{20}H_{28}N_2O_6(M+Na)^+$ 415.1840 found 415.1836.

Example 1c (Z)-2-(2-(2-methoxyethoxyl)ethoxy)ethyl 2-cyano-3-(4-(diethylamino)phenyl)acrylate (8c)

90% yield; orange liquid; $^1$H NMR (400 MHz, $CDCl_3$) δ 8.05 (s, 1H), 7.92 (d, 2H, J=9.1 Hz), 6.67 (d, 2H, J=9.2 Hz), 4.42 (m, 2H), 3.82-3.79 (m, 2H), 3.73-3.72 (m, 2H), 3.69-3.65 (m, 4H), 3.57-3.54 (m, 2H), 3.45 (q, 4H, J=7.1 Hz), 3.37 (s, 3H), 1.23 (t, 6H, J=7.1 Hz); $^{13}$CNMR (100 MHz, $CDCl_3$) δ 164.7, 154.8, 151.9, 134.8, 119.0, 117.8, 111.4, 93.0, 72.2, 71.1, 70.9, 70.8, 69.2, 65.2, 59.3, 45.0, 12.8; HRMS Calc for $C_{21}H_3N_2O_5(M+Na)^+$ 413.2047 found 413.2053.

Example 1d (Z)-2-(2-(2-methoxyethoxyl)ethoxy)ethyl-2-cyano-3-(4-(dibutylamino)phenyl)acrylate (8d)

78% yield; yellow liquid; $^1$HNMR (400 MHz, $CDCl_3$) δ 8.00 (s, 1H), 7.87 (d, 2H, J=9.0 Hz), 6.60 (d, 2H, J=9.2 Hz), 4.38 (m, 2H), 3.78-3.76 (m, 2H), 3.71-3.69 (m, 2H), 3.66-3.62 (m, 4H), 3.53-3.51 (m, 2H), 3.34-3.30 (m, 7H), 1.57 (m, 4H), 1.34 (m, 4H), 0.94 (t, 6H, J=7.3 Hz); $^{13}$CNMR (100 MHz, $CDCl_3$) δ 164.7, 154.7, 152.2, 134.6, 118.9, 117.9, 111.5, 92.8, 72.1, 71.0, 70.8, 69.1, 65.2, 59.2, 51.1, 29.5, 20.4, 14.1; HRMS Calc for $C_{25}H_{38}N_2O_5(M+Na)^+$ 469.2673 found 469.2677.

Example 1e 6-(piperidin-1-yl)-2-naphthaldehyde (10)

To a 50 ml round bottom flask containing benzene (3 mL), HMPA (3 mL) and piperidine (1.65 ml, 16.7 mmol) n-BuLi (1.6 M in hexane, 10.4 mL, 16.7 mmol) was added via syringe, at 0° C. After stirring for 15 min, the reaction mixture was treated with a solution of 6-methoxy-2-naphthaldehyde (390 mg, 2.09 mmol) in benzene: HMPA 1:1 (2 ml). The reaction mixture was warmed to room temperature, left stirring for 12 hours and then it was poured into cold 5% aqueous NaCl (30 ml). The mixture was extracted with diethyl ether (3×20 mL), dried over $MgSO_4$ and concentrated. The product was purified via flash chromatography (20% EtOAc in hexanes) to give compound 9. 9: 35% yield, yellow solid; $^1$H NMR (300 MHz, $CDCl_3$) δ 10.02 (s, 1H), 8.14 (s, 1H), 7.88-7.73 (m, 2H), 7.67 (d, 1H, J=8.6 Hz), 7.32 (dd, 1H, J=2.5 Hz, J=9.1 Hz), 7.08 (d, 1H, J=2.4 Hz), 3.42-3.32 (m, 4H), 1.85-1.57 (m, 6H); $^{13}$C NMR (100 MHz, $CDCl_3$) δ 192.2, 152.2, 138.8, 134.7, 131.6, 130.7, 127.5, 126.5, 123.6, 119.7, 109.0, 49.8, 25.8, 24.6; HRMS calc for $C_{16}H_{17}NO$ $(M+H)^+$ 240.1383 found 240.1387.

Example 1f (E)-2-(2-(2-methoxyethoxyl)ethoxy)ethyl-2-cyano-3-(6-(piperidin-1-yl)naphthalen-2-yl)acrylate (11)

82% yield; red liquid; $^1$H NMR (400 MHz, $CDCl_3$) δ 8.30 (s, 1H), 8.22 (d, 1H, J=1.2 Hz), 8.10 (dd, 1H, J=1.8 Hz, J=8.8 Hz), 7.76 (d, 1H, J=9.2 Hz), 7.65 (d, 1H, J=8.8 Hz), 7.29 (dd, 1H, J=2.4 Hz, J=9.2 Hz), 7.05 (d, 1H, J=2.2 Hz), 4.47 (m, 2H), 3.85-3.82 (m, 2H), 3.74-3.66 (m, 6H), 3.57-3.54 (m, 2H), 3.42-3.38 (m, 4H), 3.37 (s, 3H), 1.74-1.67 (m, 6H); $^{13}$C NMR (100 MHz, $CDCl_3$) δ 163.4, 155.5, 151.9, 137.8, 134.7, 130.6, 127.3, 126.4, 126.0, 125.7, 119.3, 116.4, 108.4, 98.7, 71.9, 70.8, 70.6, 70.5, 68.8, 65.4, 59.0, 49.4, 25.5, 24.3; HRMS Calc for $C_{26}H_{32}N_2O_5(M+H)^+$ 453.2384 found 453.2390.

Example 1g (2,2-dimethyl-1,3-dioxolan-4-yl)methyl 2-cyanoacetate (12)

To a solution of 2-cyanoacetic acid (1.02 g, 12 mmol), the acetal (2,2-dimethyl-1,3-dioxolan-4-yl)methanol (1.32 g, 10 mmol) in 5 ml of DCM and DMAP (61 mg, 0.50 mmol) was added dropwise at 0° C. Finally, EDC 1.86 g (12 mmol) was added and the reaction mixture was stirred at 0° C. for 6 hours. The reaction was diluted with 15 mL of DCM and the formed DCU was filtered off. The filtrate was dried over anhydrous $MgSO_4$ and the solvents were removed under reduced pressure. The residue was purified by flash chromatography (Hex: EtOAc; 10:1) to give compound 12. 12: 71% yield; colorless liquid; $^1$H NMR (400 MHz, $CDCl_3$) δ 4.34-4.32 (m, 1H), 4.28-4.17 (m, 2H), 4.07 (dd, 1H, J=6.5 Hz, J=8.5 Hz), 3.75 (dd, 1H, J=5.8 Hz, J=8.5 Hz), 3.51 (s, 2H), 1.41 (s, 3H), 1.34 (s, 3H); HRMS Calc for $C_9H_{13}NO_4$ $(M+H)^+$ 200.0923 found 200.0931.

Example 1h (E)-(2,2-dimethyl-1,3-dioxolan-4-yl)methyl 2-cyano-3-(4-(dimethylamino)phenyl)acrylate (13)

To a round bottom flask containing a solution of aldehyde 6a (0.75 g, 5.0 mmol) and compound 12 (1.2 g, 5.5 mmol) in 20 ml of THF was added 0.50 mmol of piperidine and the mixture was heated at 50° C. The crude mixture was concentrated under reduced pressure and the product was purified via flash chromatography (10-30% ethyl acetate in hexane) to give compound 13. 13: 91% yield; yellow solid; $^1$HNMR (400 MHz, $CDCl_3$) δ 8.08 (s, 1H), 7.94 (d, 2H, J=9.0 Hz), 6.69 (d, 2H, J=9.2 Hz), 4.42-4.29 (m, 3H), 4.13 (dd, 1H, J=6.2 Hz, J=8.6 Hz), 3.89 (dd, 1H, J=5.9 Hz, J=8.5 Hz), 3.11 (s, 6H), 1.46 (s, 3H), 1.38 (s, 3H); $^{13}$CNMR (400 MHz, $CDCl_3$) δ 164.3, 155.3, 153.9, 134.5, 119.5, 117.5, 111.7, 110.1, 93.3, 73.7, 66.7, 65.6, 40.3, 26.9, 25.7; HRMS Calc for $C_{18}H_{22}N_2O_4(M+H)^+$ 331.1658 found 331.1691.

Example 1i (E)-2,3-dihydroxypropyl 2-cyano-3-(4-(dimethyl-amino)phenyl) acrylate (14)

Compound 13 (0.5 g, 1.5 mmol) was dissolved in a mixture of THF/MeOH (1:1) and DOWEX-$H^+$ resin (0.10 g) was added and the heterogeneous mixture was stirred for 20 hours. The DOWEX-$H^+$ resin was removed by filtration and triethylamine (50 mg, 0.5 mmol) was added and the solvent was removed under reduced pressure. The residue was purified by flash chromatography (100% ether) to give compound 14. 14: 75% yield; bright yellow solid; $^1$H NMR (400 MHz, $CDCl_3$) δ 8.08 (s, 1H), 7.94 (d, 2H, J=9.1 Hz), 6.69 (d, 2H, J=9.2 Hz), 4.42-4.32 (m, 2H), 4.05 (m, 1H), 3.80-3.70 (m, 2H), 3.12 (s, 6H); $^{13}$C NMR (100 MHz, $CDCl_3$) δ 199.0, 164.8, 155.5, 154.0, 134.6, 119.4, 117.9, 111.8, 111.7, 92.8, 70.3, 70.2, 66.9, 66.8, 63.6, 63.5, 40.3, 40.2; HRMS Calc for $C_{15}H_{18}N_2O_4$ $(M+H)^+$ 291.1345 Found 291.1361.

Example 1j

Diethyl 4-bromobenzylphosphonate (16)

1-bromo-4-(bromomethyl) benzene (5.0 g, 20 mmol) and triethyl phosphite (51 mL, 300 mmol) were mixed in a round bottom flask and refluxed at 90° C. for 19 hours. Excess triethyl phosphite was removed under reduced pressure and the product purified by flash chromatography (1:1 Hexane/EtOAc) to give compound 16. 16: 98% yield; colorless liquid; $^1$H NMR (400 MHz, $CDCl_3$) δ 7.30 (d, 2H, J=7.5 Hz), 7.05 (d, 2H, J=7.6 Hz), 3.99-3.88 (m, 4H), 2.99 (s, 1H), 2.94 (s, 1H), 1.12 (t, 6H, J=6.9 Hz); $^{13}$C NMR (100 MHz, $CDCl_3$) δ 131.7, 131.6, 131.5, 121.0, 62.3, 34.0, 32.0, 16.5; HRMS Calc for $C_{11}H_{16}BrO_3P$ $(M+H)^+$ 307.0097 found 307.0093.

Example 1k (E)-4-(4-bromostyryl)-N,N-dimethylaniline (17)

DMF (anhydrous) (10.5 mL) was added to sodium methoxide (176 mg, 3.26 mmol) and the color was changed to pink. To the above solution diethyl 4-bromobenzylphosphonate (1.0 g, 3.26 mmol) in DMF (6.5 ml) was added dropwise over 2 minutes, followed by 4 (dimethylamino) benzaldehyde (486 mg, 3.26 mmol). The reaction mixture was stirred at room temperature for 24 hours. Deionized water (17 mL) was added. The product was filtered out through vacuum filtration and recrystallized with DCM/hexane to give compound 17. 17: 74%. Yield; tan solid; $^1$H NMR (400 MHz, $CDCl_3$) δ 7.47-7.32 (m, 6H), 7.04 (d, 1H, J=12.5 Hz), 6.83 (d, 1H, J=16.3 Hz), 6.71 (d, 2H, J=8.9 Hz), 2.99 (s, 6H); $^{13}$C NMR (100 MHz, $CDCl_3$) δ 150.5, 137.4, 136.1, 132.1, 131.8, 129.7, 128.3, 128.2, 127.9, 127.7, 125.5, 123.2, 120.3, 112.6, 40.7; HRMS Calc for $C_{16}H_{16}BrN$ 302.0541 found 302.0539.

Example 1l 4-(4-(dimethylamino)styryl)benzaldehyde (18)

To a round bottom flask compound 17 (300 mg, 1 mmol) was transferred followed by THF (5 mL). The heterogeneous solution was cooled at −78° C. and n-BuLi (1.6M in hexane, 1 mmol) was added dropwise over 5 min, followed by DMF (1.5 mL). The reaction mixture was stirred at −78° C. for 3 hours then it was quenched by water (1 mL) and the mixture was extracted with ether (2×25 mL). The combined organic extracts were washed with brine, dried over $MgSO_4$ and concentrated under reduced pressure to give compound 18. 18: 60% yield; yellow powder; $^1$H NMR (400 MHz, $CDCl_3$) δ 9.96 (s, 1H), 7.83 (d, 2H, J=8.2 Hz), 7.60 (d, 2H, J=8.2 Hz), 7.44 (d, 2H, J=8.8 Hz), 7.22 (d, 1H, J=16.2 Hz), 6.94 (d, 1H, J=16.2 Hz), 6.72 (d, 2H, J=8.8 Hz), 3.01 (s, 6H); $^{13}$C NMR (100 MHz, $CDCl_3$) δ 191.8, 150.8, 144.7, 134.7, 134.6, 132.7, 130.4, 128.4, 126.4, 124.9, 122.8, 112.4, 40.5; HRMS calc for $C_{17}H_{17}NO$ 252.1384 found 252.1383.

Example 1m (E)-2-(2-(2-methoxyethoxyl)ethoxy)ethyl-cyano-3-(4-(4(dimethylamino)styryl)phenyl)acrylate (19)

97% yield; red solid; $^1$H NMR (400 MHz, $CDCl_3$) δ 8.20 (s, 1H), 7.98 (d, 2H, J=8.4 Hz), 7.57 (d, 2H, J=8.4 Hz), 7.45 (d, 2H, J=8.7 Hz), 7.20 (d, 1H, J=16.2 Hz), 6.92 (d, 1H, J=16.2 Hz), 6.72 (d, 2H, J=8.7 Hz), 4.47 (m, 2H), 3.84-3.82 (m, 2H), 3.74-3.72 (m, 2H), 3.70-3.66 (m, 4H), 3.57-3.55 (m, 2H), 3.37 (s, 3H), 3.02 (s, 6H); $^{13}$C NMR (100 MHz, $CDCl_3$) δ 154.9, 133.0, 132.2, 128.6, 128.5, 126.7, 122.7, 112.4, 72.2, 71.1, 70.8, 69.0, 65.8, 59.3, 40.6, 40.5, 29.9, 28.2; HRMS calc for $C_{27}H_{32}N_2O_5(M+Na)^+$ 487.2203 found 487.2201.

Example 2

Compound Synthesis of Compounds 27-33

Results of analysis of compounds described herein are provided in Examples 2a-2o following.

General Notes.

All reagents were purchased at highest commercial quality and used without further purification except where noted. Air- and moisture-sensitive liquids and solutions were transferred via syringe or stainless steel cannula. Organic solutions were concentrated by rotary evaporation below 45° C. at approximately 20 mmHg. All non-aqueous reactions were carried out under anhydrous conditions. Yields refer to chromatographically and spectroscopically ($^1$H NMR, $^{13}$C NMR) homogeneous materials, unless otherwise stated. Reactions were monitored by thin-layer chromatography (TLC) carried out on 0.25 mm Dynamic Adsorbents, Inc. silica gel plates (60F-254) and visualized under UV light and/or developed by dipping in solutions of 10% ethanolic phosphomolybdic acid (PMA) and applying heat. Dynamic Adsorbents, Inc. silica gel (60, particle size 0.040-0.063 mm) was used for flash chromatography. NMR spectra were recorded on the Varian Mercury 400, 300 and/or Unity 500 MHz instruments and calibrated using the residual non-deuterated solvent as an internal reference. The following abbreviations were used to explain the multiplicities: s=singlet, d=doublet, t=triplet, q=quartet, m=multiplet, b=broad. High resolution mass spectra (HRMS) were recorded on a VG 7070 HS mass spectrometer under electron spray ionization (ESI) or electron impact (EI) conditions.

A general strategy for the synthesis of compounds described herein including compounds 27-33 is depicted in scheme 5. Commercially available methyl 6-bromo naphthalene-2-carboxylate (20) was converted to the corresponded naphthaldehyde 21 in two steps: a) reduction of the ester to the primary alcohol by using DIBALH and b) oxidation of the alcohol to the aldehyde after treatment with PCC. Granzhan, A.; Teulade-Fichou, M.-P., *Tetrahedron* 2009, 65, (7), 1349-1360. The transformation of the bromide to the appropriate amine demanded the use of novel chemistry to improve the yield and apply the method in bigger scale. Treatment of bromide 21 in the presence of palladium using Buchwald and Hartwig conditions resulted aldehydes 22-25 in excellent yield for most cases. Guram, A. S.; Rennels, R. A.; Buchwald, S. L., *Angew. Chem. Int. Ed. Engl.* 1995, 34, (12), 1348-1350; Wolfe, J. P.; Buchwald, S. L., *J. Org. Chem.* 2000, 65, (4), 1144-1157; Hartwig, J. F., *Accounts Chem. Res.* 2008, 41, (11), 1534-1544. Knovenagel condensation of aldehydes 22-25 and the appropriate cyanoester 26 concluded the synthesis of the final probes 27-32. Sutharsan, J.; Lichlyter, D.; Wright, N. E.; Dakanali, M.; Haidekker, M. A.; Theodorakis, E. A., *Tetrahedron* 2010, 66, (14), 2582-2588. Deprotection of the acetal in probe 32 by using acidic resin, yielded the final dye 33. Table 3 summarizes the R, X combinations of the final products and the condensation yields.

Scheme 5. General strategy for the synthesis of probes 27-33

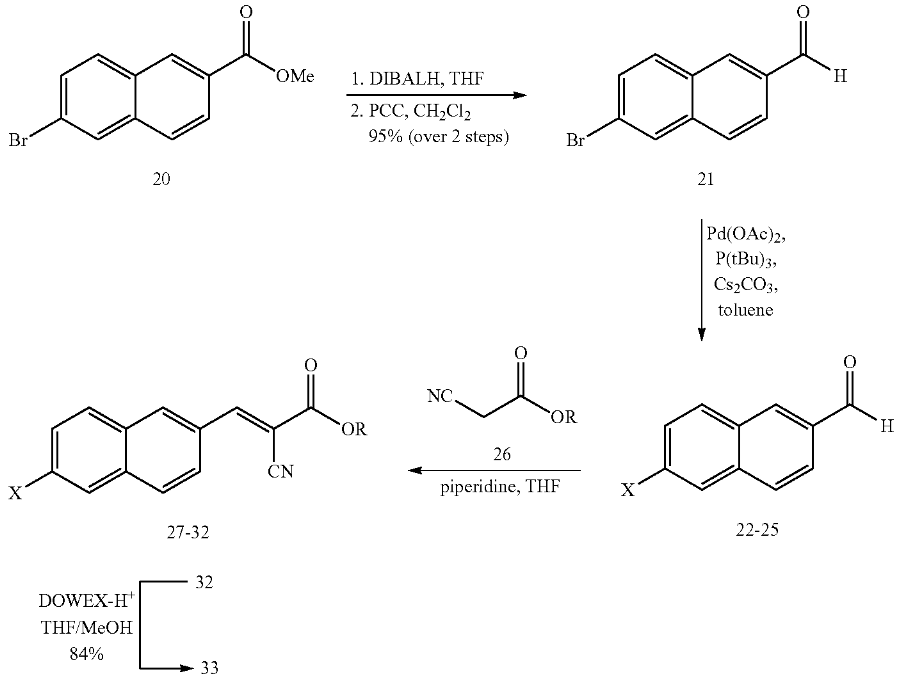

22: X = piperidine (70%)
23: X = morpholine (79%)
24: X = methylpiperazine (77%)
25: X = 2-morpholino-ethanamine (33%)

TABLE 3

| Structures and yields for the Aβ binding probes | | | |
|---|---|---|---|
| Compound | X | R | Yield |
| 27 | 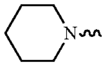 | 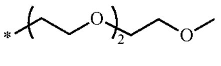 | 90% |
| 28 | 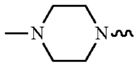 | 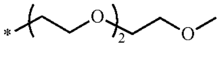 | 85% |
| 29 | 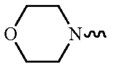 | 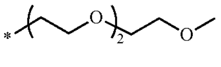 | 83% |
| 30 | 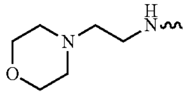 | 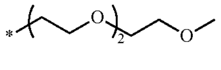 | 87% |
| 31 | 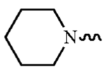 | 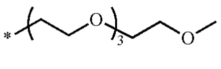 | 89% |
| 32 | 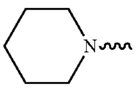 | 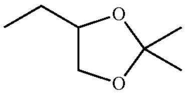 | 83% |
| 33 | 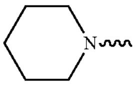 | 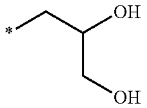 [SMILES: *CC(O)CO] | 84% |

Example 2a 6-bromo-2-naphtaldehyde (21)

To a solution of DIBAL-H (1.0 M in heptane, 34 mL, 34 mmol) at 0° C. under argon, a solution of 20 (3.0 gr, 11 mmol) in anhydrous THF was added dropwise. The reaction mixture was allowed to warm up to room temperature and left stirring overnight. Upon completion, MeOH was added, followed by a saturated sodium potassium tartrate solution and ethylacetate. After the two phases were separated, the organic phase was washed with saturated solution of ammonium chloride and brine, dried over $MgSO_4$ and concentrated under reduced pressure to yield 6-bromo-2-(hydroxymethyl)naphthalene. $^1$H NMR (400 MHz, $CDCl_3$): δ 7.99 (bs, 1H), 7.77 (bs, 1H), 7.74 (d, 1H, J=8.5 Hz), 7.69 (d, 1H, J=8.7 Hz), 7.55 (dd, 1H, J=1.7 Hz, J=8.7 Hz), 7.49 (dd, 1H, J=1.7 Hz, J=8.5 Hz), 4.84 (bs, 2H); $^{13}$C NMR (100 MHz, $CDCl_3$) δ 138.8, 133.9, 131.7, 129.7, 129.5, 129.5, 127.4, 126.1, 125.2, 119.8, 65.2.

To a suspension of pyridinium chlorochromate (2.4 gr, 11 mmol) in anhydrous $CH_2Cl_2$ (60 mL) was added a solution of the above alcohol in anh. $CH_2Cl_2$ and the reaction was heated under reflux for 5 hours. Upon completion, it was cooled to room temperature and poured into diethyl ether. The solution was then filtered through a pad of silica and concentrated under reduced pressure to yield 21 (2.4 gr, 95%). 20: white solid; $^1$H NMR (400 MHz, $CDCl_3$) δ 10.15 (s, 1H), 8.31 (bs, 1H), 8.08 (bs, 1H), 7.98 (dd, 1H, J=1.5 Hz, J=8.5 Hz), 7.86 (m, 2H), 7.67 (dd, 1H, J=1.5 Hz, J=8.5 Hz); $^{13}$C NMR (100 MHz, $CDCl_3$) δ 191.8, 137.3, 134.3, 134.1, 131.0, 131.0, 130.6, 130.2, 128.2, 124.0, 123.

General Procedure for the Synthesis of 6-amino-substituted Naphtaldehydes (Cmpds 22-25)

In dry and degassed toluene (0.8 mL), were added $Pd(OAc)_2$ (0.022 mmol) and $P(tBu)_3$ (0.078 mmol) After stirring for 20 min, 8 (0.207 mmol), the appropriate amine (0.249 mmol) and $Cs_2CO_3$ (0.280 mmol) were added and the reaction left stirring for three days under reflux. After three days, the reaction was cooled at room temperature, diluted with $CH_2Cl_2$, filtered, concentrated under reduced pressure and purified via silica gel flash chromatography (hexanes/EtOAc 0-10%).

Example 2b 6-(piperidin-1-yl)naphthalene-2-carbaldehyde (22)

70% yield, yellow solid; $^1$H NMR (400 MHz, $CDCl_3$) δ 10.03 (s, 1H), 8.15 (s, 1H), 7.83 (m, 2H), 7.68 (d, 1H, J=8.6 Hz) 7.32 (dd, 1H, J=2.4 Hz, J=9.1 Hz), 7.08 (d, 1H, J=2.4 Hz), 3.38 (m, 4H), 1.78-1.63 (m, 6H); $^{13}$C NMR (100 MHz, $CDCl_3$) δ 191.9, 151.9, 138.5, 134.4, 131.3, 130.4, 127.2, 126.3, 123.4, 119.5, 108.8, 49.6, 25.5, 24.3; HRMS Calc for $C_{16}H_{18}NO$ $(M+H)^+$ 240.1383 found 240.1381.

Example 2c 6-morpholinonaphthalene-2-carbaldehyde (23)

79% yield, yellow solid; $^1$H NMR (400 MHz, $CDCl_3$) δ 10.06 (s, 1H), 8.20 (s, 1H), 7.88 (m, 2H), 7.73 (d, 1H, J=8.4 Hz), 7.32 (m, 1H), 7.11 (d, 1H, J=1.2 Hz), 3.92 (m, 4H), 3.36 (m, 4H); $^{13}$C NMR (100 MHz, $CDCl_3$) δ 191.9, 151.3, 138.1, 134.2, 131.8, 130.6, 127.5, 127.0, 123.6, 118.7, 109.0, 66.7, 48.5; HRMS Calc for $C_{15}H_{15}NO_2Na$ $(M+Na)^+$ 264.0995 found 264.0996.

Example 2d 6-(4-methylpiperazin-1-yl)naphthalene-2-carbaldehyde (24)

77% yield, yellow solid; $^1$H NMR (300 MHz, $CDCl_3$) δ 10.00 (s, 1H), 8.13 (s, 1H), 7.80 (m, 2H), 7.66 (d, 1H, J=8.6 Hz), 7.28 (dd, 1H, J=2.1 Hz, J=9.2 Hz), 7.06 (d, 1H, J=2.1 Hz), 3.36 (m, 4H), 2.57 (m, 4H), 2.33 (s, 3H); $^{13}$C NMR (100 MHz, $CDCl_3$) δ 191.5, 151.0, 138.0, 134.0, 131.3, 130.2, 127.1, 126.4, 123.1, 118.7, 108.7, 54.5, 47.8, 45.7; HRMS Calc for $C_{16}H_{19}N_2O$ $(M+H)^+$ 255.1492 found 255.1491.

Example 2e 6-(2-morpholinoethylamino)naphthalene-2-carbaldehyde (25)

33% yield, yellow solid; $^1$H NMR (400 MHz, $CDCl_3$) δ 10.01 (s, 1H), 8.14 (s, 1H), 7.83 (dd, 1H, J=1.6 Hz, J=8.6 Hz), 7.76 (d, 1H, J=8.9 Hz), 7.64 (d, 1H, J=8.6 Hz), 6.98 (dd, 1H, J=2.3 Hz, J=8.9 Hz), 6.79 (d, 1H, J=2.3 Hz), 4.88 (bs, 1H), 3.75 (m, 4H), 3.31 (dd, 2H, J=5.1 Hz, J=11.1 Hz), 2.72 (m, 2H), 2.51 (bs, 4H); $^{13}$C NMR (100 MHz, $CDCl_3$) δ 191.9, 148.8, 139.1, 134.6, 130.8, 130.7, 126.6, 126.0, 123.8, 118.7, 103.8, 66.9, 56.7, 53.3, 39.3; HRMS Calc for $C_{17}H_{21}N_2O_2$ $(M+H)^+$ 285.1598 found 285.1600.

General Procedure for the Synthesis of 2-cyanoacetates (26)

To a solution of 2-cyanoacetic acid (2.72 mmol), the appropriate alcohol (2.27 mmol) in $CH_2Cl_2$ (2.5 mL) and DMAP (0.013 mmol) was added dropwise at 0° C. Finally, DCC (2.72 mmol) was added and the reaction mixture was stirred at 0° C. for 6 hours. The reaction was diluted with $CH_2Cl_2$ and the formed DCU was filtered off. The filtrate was dried over $MgSO_4$ and concentrated under reduced pressure. The residue was purified by silica gel flash chromatography to yield 2-cyanoacetate 7.

Example 2f 2-(2-(2-methoxyethoxyl)ethoxy)ethyl-2-cyanoacetate (26a)

86% yield; colorless liquid; $^1H$ NMR (400 MHz, $CDCl_3$) δ 4.29 (m, 2H), 3.67, (m, 2H), 3.59 (m, 6H), 3.50 (m, 2H), 3.49 (s, 2H), 3.32 (s, 3H); $^{13}C$ NMR (100 MHz, $CDCl_3$) δ 163.0, 113.0, 71.7, 70.4, 70.3, 68.3, 65.5, 58.8, 24.5; HRMS: calcd. for $C_{10}H_{17}NO_5$: $(M+H^+)$ 232.1185. found 232.1199.

Example 2g 2-(2-(2-(2-methoxyethoxyl)ethoxy)ethoxy)ethyl-2-cyanoacetate (26b)

68% yield; colorless liquid; $^1H$ NMR (400 MHz, $CDCl_3$) δ 4.21 (bs, 2H), 3.61 (bs, 2H), 3.51 (m, 12H), 3.43 (m, 2H), 3.24 (bs, 3H) $^{13}C$ NMR (100 MHz, $CDCl_3$) δ 163.0, 113.0, 71.4, 70.2, 70.1, 70.1, 70.0, 68.1, 65.3, 58.5, 24.2;

Example 2h (2,2-dimethyl-1,3-dioxolan-4-yl)methyl 2-cyanoacetate (26c)

71% yield; colorless liquid; $^1H$ NMR (400 MHz, $CDCl_3$) δ 4.35 (m, 1H), 4.29-4.19 (m, 2H), 4.09 (m, 1H), 3.76 (dd, 1H, J=5.8 Hz, J=8.6 Hz), 3.52 (s, 2H), 1.43 (s, 3H), 1.36 (s, 3H); $^{13}C$ NMR (100 MHz, $CDCl_3$) δ 162.8, 112.7, 110.1, 73.0, 66.8, 65.9, 26.6, 25.2, 24.6; HRMS Calc for $C_9H_{13}NO_4$ $(M+H)^+$ 200.0923 found 200.0931.

General Procedure for the Synthesis of Fluorescent Probes 27-33

To a round bottom flask containing a solution of aldehyde (0.21 mmol) and the appropriate 2-cyanoacetate (0.23 mmol) in THF (0.8 mL), piperidine (0.02 mmol) was added and the mixture left stirring at 50° C. The reaction was monitored by TLC and was completed within 21 hours. The crude mixture was concentrated under reduced pressure and the product was purified via flash column chromatography (10-30% EtOAc in hexanes).

Example 2i (E)-2-(2-(2-methoxyethoxyl)ethoxy)ethyl 2-cyano-3-(2-(piperidin-1-yl)napthalen-6-yl)acrylate (27)

90% yield; red liquid; $^1H$ NMR (400 MHz, $CDCl_3$) δ 8.31 (s, 1H), 8.22 (bs, 1H), 8.10 (d, 1H, J=8.8 Hz), 7.76 (d, 1H, J=9.2 Hz), 7.65 (d, 1H, J=8.8 Hz), 7.30 (dd, 1H, J=2.1 Hz, J=9.2 Hz), 7.05 (d, 1H, J=2.1 Hz), 4.47 (m, 2H), 3.83 (m, 2H), 3.74-3.66 (m, 6H), 3.56 (m, 2H), 3.42-3.38 (m, 4H), 3.37 (s, 3H), 1.74 (m, 6H); $^{13}C$ NMR (100 MHz, $CDCl_3$) δ 163.3, 155.4, 151.9, 137.7, 134.7, 130.6, 127.2, 126.4, 125.9, 125.6, 119.2, 116.4, 108.3, 71.8, 70.7, 70.5, 70.5, 68.7, 65.3, 58.9, 49.3, 25.4, 24.3; HRMS Calc for $C_{26}H_{32}N_2O_5Na$ $(M+Na)^+$ 475.2203 found 475.2197.

Example 2j (E)-2-(2-(2-methoxyethoxyl)ethoxy)ethyl 2-cyano-3-(2-(4-methylpiperazin-1-yl)napthalen-6-yl) acrylate (28)

85% yield; red liquid; $^1H$ NMR (400 MHz, $CDCl_3$) δ 8.31 (s, 1H), 8.23 (s, 1H), 8.10 (d, 1H, J=8.6 Hz), 7.78 (d, 1H, J=9.1 Hz), 7.67 (d, 1H, J=8.6 Hz), 7.29 (d, 1H, J=9.1 Hz), 7.06 (s, 1H), 4.46 (m, 2H), 3.83 (m, 2H), 3.73 (m, 2H), 3.67 (m, 4H), 3.55 (m, 2H) 3.42 (bs, 4H), 3.36 (s, 3H), 2.61 (bs, 4H), 2.37 (s, 3H); $^{13}C$ NMR (100 MHz, $CDCl_3$) δ 163.2, 155.4, 151.4, 137.5, 134.5, 130.6, 127.4, 126.9, 126.1, 126.1, 119.0, 116.2, 108.7, 99.3, 71.9, 70.8, 70.6, 70.5, 68.8, 65.4, 59.0, 54.8, 48.0, 46.1; HRMS Calc for $C_{26}H_{34}N_3O_5$ $(M+H)^+$ 468.2493 found 468.2494.

Example 2k (E)-2-(2-(2-methoxyethoxyl)ethoxy)ethyl 2-cyano-3-(2-morpholinonapthalen-6-yl)acrylate (29)

83% yield; red liquid; $^1H$ NMR (300 MHz, $CDCl_3$) δ 8.31 (s, 1H), 8.24 (s, 1H), 8.11 (dd, 1H, J=1.9 Hz, J=8.8 Hz), 7.80 (d, 1H, J=9.1 Hz), 7.69 (d, 1H, J=8.8 Hz), 7.28 (m, 1H), 7.06 (d, 1H, J=1.9 Hz), 4.47 (m, 2H), 3.90 (m, 4H), 3.83 (m, 2H), 3.70 (m, 6H), 3.55 (m, 2H), 3.35 (m, 7H); $^{13}C$ NMR (100 MHz, $CDCl_3$) δ 163.0, 155.2, 151.3, 137.2, 134.4, 130.6, 127.4, 127.0, 126.1, 126.0, 118.5, 116.1, 108.5, 99.4, 71.8, 70.7, 70.5, 70.4, 68.6, 66.5, 65.3, 58.9, 48.2; HRMS Calc for $C_{25}H_{30}N_2O_6Na$ $(M+Na)^+$ 477.1996 found 477.1995.

Example 2l (E)-2-(2-(2-methoxyethoxyl)ethoxy)ethyl 3-(2-(2-morpholinoethylamino) naphthalen-6-yl)-2-cyano acrylate (30)

87% yield; red liquid; $^1H$ NMR (500 MHz, $CDCl_3$) δ 8.28 (s, 1H), 8.19 (d, 1H, J=1.6 Hz), 8.08 (dd, 1H, J=1.9 Hz, J=8.8 Hz), 7.69 (d, 1H, J=8.9 Hz), 7.60 (d, 1H, J=8.8 Hz), 6.95 (dd, 1H, J=2.3 Hz, J=8.8 Hz), 6.74 (d, 1H, J=2.2 Hz), 4.96 (bs, 1H), 4.46 (m, 2H), 3.83 (m, 2H), 3.76-3.72 (m, 6H), 3.69-3.65 (m, 4H), 3.57-3.54 (m, 2H), 3.36 (s, 3H), 3.31 (s, 2H), 2.70 (m, 2H), 2.51 (s, 4H); $^{13}C$ NMR (100 MHz, $CDCl_3$) δ 163.4, 155.5, 149.0, 138.3, 135.0, 130.9, 126.6, 126.3, 126.2, 124.9, 118.9, 116.5, 103.6, 98.2, 71.9, 70.8, 70.6, 70.5, 68.8, 66.9, 65.3, 59.0, 56.6, 53.2, 39.2; HRMS Calc for $C_{27}H_{36}N_3O_6$ $(M+H)^+$ 498.2599 found 498.2596.

Example 2lm (E)-2-(2-(2-(2-methoxyethoxyl)ethoxy)ethoxy)ethyl 2-cyano-3-(2-(piperidin-1-yl)napthalen-6-yl) acrylate (31)

89% yield; red liquid; $^1H$ NMR (400 MHz, $CDCl_3$) δ 8.20 (s, 1H), 8.10 (s, 1H), 8.01 (d, 1H, J=8.5 Hz), 7.66 (d, 1H, J=9.0 Hz), 7.55 (d, 1H, J=9.0 Hz), 7.20 (d, 1H, J=8.5 Hz), 6.95 (s, 1H), 4.39 (bs, 2H), 3.75 (bs, 2H), 3.65-3.54 (m, 10H), 3.45 (m, 2H), 3.31 (bs, 4H), 3.28 (s, 3H), 1.65-1.54 (m, 6H); $^{13}C$ NMR (100 MHz, $CDCl_3$) δ 163.2, 155.3, 151.8, 137.6, 134.6, 130.5, 127.1, 126.3, 125.8, 125.5, 119.1, 116.3, 108.2, 98.4, 71.7, 70.6, 70.4, 70.3, 68.6, 65.3, 58.8, 49.2, 25.3, 24.2; HRMS Calc for $C_{28}H_{36}N_2O_6Na$ $(M+Na)^+$ 519.2466 found 519.2468.

Example 2n

(E)-(2,2-dimethyl-1,3-dioxolan-4-yl)methyl 2-cyano-3-(2-(piperidin-1-yl)naphthalene-6-yl) acrylate (32)

83% yield; red liquid; $^1H$ NMR (400 MHz, $CDCl_3$) δ 8.29 (s, 1H), 8.19 (s, 1H), 8.09 (dd, 1H, J=1.9 Hz, J=8.8 Hz), 7.74 (d, 1H, J=9.3 Hz), 7.63 (d, 1H, J=8.8 Hz), 7.28 (dd, 1H, J=2.8 Hz, J=9.3 Hz), 7.03 (d, 1H, J=1.9 Hz), 4.43 (m, 1H), 4.36 (m, 2H), 4.14 (dd, 1H, J=6.0 Hz, J=8.5 Hz), 3.90 (dd, 1H, J=6.0 Hz, J=8.5 Hz), 3.40 (m, 4H), 1.73-1.66 (m, 6H), 1.48 (s, 3H), 1.39 (s, 3H); $^{13}C$ NMR (100 MHz, $CDCl_3$) δ 162.9, 155.4, 151.5, 137.6, 134.6, 130.5, 127.0, 126.2, 125.6, 125.3, 119.0, 116.1, 109.6, 108.2, 98.0, 73.1, 65.9, 65.6, 57.1, 49.1, 45.5, 29.4, 26.4, 25.2, 24.0; MS $(M+H)^+$ 421.24.

Example 2o

(E)-2,3-dihydroxypropyl 2-cyano-3-(2-(piperidin-1-yl)naphthalene-6-yl)acrylate (33)

Compound 31 (50 mgr, 0.12 mmol) was dissolved in a mixture of THF/MeOH (1:1) and DOWEX-$H^+$ resin (15 mgr) was added and the heterogeneous mixture was stirred for 20 hours. The resin was removed by filtration and triethylamine was added and the solvent was removed under reduced pressure. The residue was purified by flash chromatography to give compound 32. 32: 38 mgr, 84% yield; red liquid; $^1H$ NMR (400 MHz, $CDCl_3$) δ 8.30 (s, 1H), 8.19 (s, 1H), 8.08 (d, 1H, J=8.8 Hz), 7.74 (d, 1H, J=9.1 Hz), 7.63 (d, 1H, J=9.1 Hz), 7.29 (m, 1H), 7.03 (s, 1H), 4.46-4.36 (m, 2H), 4.09 (m, 1H), 3.81 (dd, 1H, J=5.5 Hz, J=11.3 Hz), 3.73 (dd, 1H, J=5.5 Hz, J=11.3 Hz), 3.41 (m, 4H), 1.74-1.67 (m, 6H); $^{13}C$ NMR (100 MHz, $CDCl_3$) δ 163.6, 156.0, 152.0, 137.9, 135.0, 130.7, 127.3, 126.3, 125.9, 125.5, 119.2, 116.6, 108.3, 97.8, 69.9, 67.0, 63.2, 49.3, 25.5, 24.3; HRMS Calc for $C_{22}H_{25}N_2O_4$ $(M+H)^+$ 381.1809 found 381.1802.

Example 3

Detection and Binding Studies

Studies for Compounds 8a-8d, 11, 14 and 18.

An initial study to determine whether a compound can associate with aggregated Aβ is to compare its fluorescence spectra before and after mixing with the Aβ aggregates. See E. E. Nesterov, J. Skoch, B. T. Hyman, W. E. Klunk, B. J. Bacskai, T. M. Swager, *Angew. Chem. Int. Edit.* 2005, 44:5452-5456; Z. P. Zhuang, M. P. Kung, H. F. Kung, *J. Med. Chem.* 2006, 49:2841-2844; Q. A. Li, J. S. Lee, C. Ha, C. B. Park, G. Yang, W. B. Gan, Y. T. Chang, *Angew. Chem. Int. Edit.* 2004, 43:6331-6335; H. F. Kung, C. W. Lee, Z. P. Zhuang, M. P. Kung, C. Hou, K. Plossl, *J. Am. Chem. Soc.* 2001, 123:12740-12741. Typically, a fluorescent amyloid-binding agent displays a significant fluorescence intensity increase after binding to Aβ aggregates as compared to its native fluorescence in solution. See H. LeVine III, *Protein Sci.* 1993, 2:404-410. Along these lines we measured the fluorescent properties of each compound at 4 μM concentration before and after mixing with preaggregated Aβ(1-42) peptides (5 μM, aggregated in PBS buffer for 3 days at 25° C.).

In all cases, a 1.3-9.4 fold fluorescence intensity increase was observed in the presence of aggregated Aβ, indicating that these compounds bind to the peptide (Table 2). In most cases a modest blue-shift (6-20 nm) was observed upon binding. Only in the case of the naphthalene-based Cmpd 11 was a significant red shift of 76 nm observed upon binding to preaggregated Aβ (FIGS. 1*c*, 1*d*). Interestingly, this binding was accompanied with a 9.3 fold intensity increase. A similar intensity increase has been observed with FDDNP and may be explained by the ability of the naphthalene motif to create excimers upon binding to its target. See E. D. Agdeppa, V. Kepe, J. Liu, S. Flores-Torres, N. Satyamurthy, A. Petric, G. M. Cole, G. W. Small, S. C. Huang, J. R. Barrio, *J. Neurosci.* 2001, 21:1-5; S. Abad, I. Vaya, M. C. Jimenez, U. Pischel, M. A. Miranda, *ChemPhysChem* 2006, 7:2175-2183; C. Spies, R. Gehrke J. *Phys. Chem. A* 2002, 106:5348-5352.

Cmpds 8a and 8b exhibited similar fluorescence characteristics suggesting that addition of a methoxy group on the phenyl group does not alter the binding properties of the compound as a probe. On the other hand, it is worth noting that increasing the size of the alkyl groups of the nitrogen leads to a significant increase in the fluorescence intensity after binding (Table 4, 8a, 8c, 8d). This is likely a result of the decreased rotational freedom of the molecules upon binding to the aggregated forms of Aβ peptide. See W. Schuddeboom, S. A. Jonker, J. M. Warman, U. Leinhos, W. Kuehnle, K. A. Zachariasse, *J. Phys. Chem.* 1992, 96:10809-10819; Y. V. Il'chev, W. Kuehnle, K. A. Zachariasse, *J. Phys. Chem.* 1998, 102:5670-5680. Interestingly, no increase of fluorescence intensity was observed upon mixing of these compounds with monomeric Aβ peptide. This supports the notion that these compounds bind selectively to aggregated forms of Aβ. The fluorescence profile of 8d (excitation and emission) is shown in FIG. 1A and FIG. 1B.

TABLE 4

Fluorescence profile, Kd, $IC_{50}$ and related values for the interaction of the synthesized compounds with aggregated Aβ(1-42) peptides

| Comp No | Excitation max before binding (nm) | Excitation max after binding (nm) | Emission max before binding (nm) | Emission max after binding (nm) | Fold increase | $K_d$ (μM) | $R^2$ | Maximum % inhibition (ELISA) | $IC_{50}$ (μM) (ELISA) | LogP |
|---|---|---|---|---|---|---|---|---|---|---|
| 8a | 439 | 435 | 476 | 470 | 1.8 | 2.6 | 0.93 | 81 | 129.0 | 1.74 |
| 8b | 442 | 444 | 478 | 469 | 1.3 | 5.3 | 0.99 | 92 | 1.2 | 1.54 |
| 8c | 445 | 442 | 478 | 470 | 4.2 | 4.8 | 0.96 | 98 | 11.4 | 2.49 |

TABLE 4-continued

Fluorescence profile, Kd, $IC_{50}$ and related values for the interaction of the synthesized compounds with aggregated Aβ(1-42) peptides

| Comp No | Excitation max before binding (nm) | Excitation max after binding (nm) | Emission max before binding (nm) | Emission max after binding (nm) | Fold increase | $K_d$ (μM) | $R^2$ | Maximum % inhibition (ELISA) | $IC_{50}$ (μM) (ELISA) | LogP |
|---|---|---|---|---|---|---|---|---|---|---|
| 8d | 432 | 440 | 466 | 468 | 9.4 | 4.4 | 0.95 | 91 | 90.6 | 4.62 |
| 11 | 445 | 440 | 462 | 538 | 9.3 | 2.5 | 0.98 | 58 | 74.3 | 3.81 |
| 14 | 437 | 434 | 476 | 467 | 2.2 | 3.3 | 0.99 | 79 | 82.1 | 1.07 |
| 19 | 312 | 319 | 658 | 638 | 2.3 | 1.4 | 0.98 | 40 | 33.6 | 4.30 |

Aggregated Aβ peptide was prepared by dissolving Aβ(1-42) in PBS pH 7.4 to a final concentration of 100 μM. This solution was magnetically stirred at 1200 rpm for 3 days at room temperature. The 100 μM Aβ(1-42) stock solution in PBS was aliquoted and frozen at 80° C. for up to 4 weeks without noticeable change in its property. 150 μL of pre-aggregated Aβ(1-42) was added to 2.85 mL of compound to attain a final concentration of 5 μM Aβ(1-42) and 4 μM of compound. The solution was transferred to 3 mL cuvette and the fluorescence measured at 25° C. As shown in FIG. 4, association of compounds described herein with aggregated Aβ provides changes in both excitation and emission spectra. The fluorescence excitation spectra of Cmpds 8a, 8b, 8c, 14 and 19 are depicted in FIG. 4, respectively.

We also measured the apparent binding constants (Kd) of the compounds (in concentrations of 10, 5, 2.5 and 1.25 μM) to 5.0 μM pre-aggregated Aβ(1-42) peptide. The Kd can be measured from the double reciprocal of the fluorescent maximum and the concentration of the compound. See H. LeVine III, *Protein Sci.* 1993, 2:404-410. All Kd values were measured between 1.4 and 5.3 μM (Table 4). It is remarkable that, despite the structural differences, these compounds display similar Kd values suggesting that they bind in a similar fashion to aggregated Aβ. Moreover, these values are similar to the reported Kd values for ThT (2 μM). [22,] See LeVine, Id.; Lockhart, L. Ye, D. B. Judd, A. T. Merritt, P. N. Lowe, J. L. Morgenstern, G. Z. Hong, A. D. Gee, J. Brown, *J. Biol. Chem.* 2005, 280:7677-7684; M. Biancalana, K. Makabe, A. Koide, S. Koide, *J. Mol. Biol.* 2008, 383:205-213; M. Biancalana, K. Makabe, A. Koide, S. Koide, *J. Mol. Biol.* 2009, 385:1052-1063. The double reciprocal plot of fluorescence intensity versus concentration of Cmpds 8d and 11 are shown in FIG. 2. The Kd corresponds to the −1/(x-intercept) of the linear regression.

The association of the synthesized compounds with aggregated Aβ peptides was tested using a semi-quantitative ELISA based assay developed by Yang and co-workers. See P. Inbar, J. Yang, Bioorg. *Med. Chem. Lett.* 2006, 16:1076-1079; P. Inbar, C. Q. Li, S. A. Takayama, M. R. Bautista, J. Yang, *ChemBioChem* 2006, 7:1563-1566; P. Inbar, M. R. Bautista, S. A. Takayama, J. Yang, *Anal. Chem.* 2008, 80:3502-3506. The assay is based on screening for molecules that inhibit the interaction of the aggregated Aβ peptide with a monoclonal anti-Aβ IgG raised against residues 1-17 of Aβ. Table 4 provides the concentrations of the compounds corresponding to 50% inhibition ($IC_{50}$) of the IgG-Aβ interactions as well as the maximal percentage of the IgG's inhibited from binding to the fibrils. All compounds exhibited $IC_{50}$ values at μM levels, the lowest value being measured for 8b (IC50=1.17 μM). The maximum inhibition, a measure of the extent of surface coating of the aggregated peptide by the compounds, was determined to be between 40-98% (Table 4). See P. Inbar, J. Yang, Bioorg. *Med. Chem. Lett.* 2006, 16:1076-1079; P. Inbar, C. Q. Li, S. A. Takayama, M. R. Bautista, J. Yang, *ChemBioChem* 2006, 7:1563-1566; P. Inbar, M. R. Bautista, S. A. Takayama, J. Yang, *Anal. Chem.* 2008, 80:3502-3506. Comparison of these data indicates that the surface coating increases by decreasing the size of the compound or the extent of the IC system. Specifically, while the maximum inhibition is between 81-98% for the phenyl compounds, it decreases to 58% for the longer naphthalene compound 11 and to 40% for the more conjugated stilbene 19. Representative graphs for Cmpds 8d and 11 are shown in FIG. 3. Representative graphs for Cmpds 8a, 8b, 8c and 14 are shown in FIGS. 7A-D, respectively.

The log P values for all the compounds were calculated to be between 1.07 and 4.62 (Table 2) indicating that most of these compounds meet the solubility criteria and should be able to cross the blood brain barrier. See P. Inbar, J. Yang, Bioorg. Med. *Chem. Lett.* 2006, 16:1076-1079; P. Inbar, C. Q. Li, S. A. Takayama, M. R. Bautista, J. Yang, *ChemBioChem* 2006, 7:1563-1566; P. Inbar, M. R. Bautista, S. A. Takayama, J. Yang, *Anal. Chem.* 2008, 80:3502-3506; C. A. Lipinski, F. Lombardo, B. W. Dominy, P. J. Feeney, *Adv. Drug Deliver. Rev.* 1997, 23:3-25. Log P values were calculated using the Molinspiration Chem-informatics software.

Studies for Compounds 27-31 and 33.

Aggregated Aβ peptide was prepared by dissolving Aβ(1-42) in PBS pH 7.4 to a final concentration of 100 μM. This solution was magnetically stirred at 1200 rpm for 3 days at room temperature. The 100 μM Aβ(1-42) stock solution in PBS was aliquoted and frozen at −10° C. for up to 4 weeks without noticeable change in its property. 15 μL of the pre-aggregated Aβ(1-42) was added to 285 μL of the probe (5% DMSO in nano-pure water) to attain a final concentration of 5 μM Aβ(1-42) and 4 μM of the probe. The solution was transferred to a 300 mL cuvette and the fluorescent measured. FIGS. 9A-F show fluorescence excitation spectra of Cmpds 27-31 and 33, respectively.

TABLE 5

Fluorescence profile, $K_d$ and logP values of the synthesized probes with aggregated Aβ(1-42) peptides

| Cmp. # | Exc. max (nm) before | Exc. max (nm) after | Em. max (nm) before | Em. max (nm) after | Fold increase | $K_d$ | SD | $R^2$ | logP |
|---|---|---|---|---|---|---|---|---|---|
| 27 | 415 | 410 | 590 | 545 | 7.7 | 1.4 | 0.2 | 0.99 | 3.81 |
| 28 | 400 | 385 | 580 | 530 | 4.9 | 4.6 | 1.3 | 0.98 | 2.79 |

TABLE 5-continued

Fluorescence profile, $K_d$ and logP values of the synthesized probes with aggregated Aβ(1-42) peptides

| Cmp. # | Exc. max (nm) before | Exc. max (nm) after | Em. max (nm) before | Em. max (nm) after | Fold increase | $K_d$ | SD | $R^2$ | logP |
|---|---|---|---|---|---|---|---|---|---|
| 29 | 400 | 380 | 530 | 525 | 5.1 | 13.8 | 2.9 | 0.99 | 2.74 |
| 30 | 430 | 430 | 570 | 540 | 2.9 | 6.7 | 2.1 | 0.98 | 2.53 |
| 31 | 420 | 410 | 590 | 546 | 8.3 | 1.6 | 0.3 | 0.93 | 3.60 |
| 33 | 410 | 410 | 540 | 535 | 7.2 | 1.6 | 0.9 | 0.93 | 3.14 |

Figure 9A:
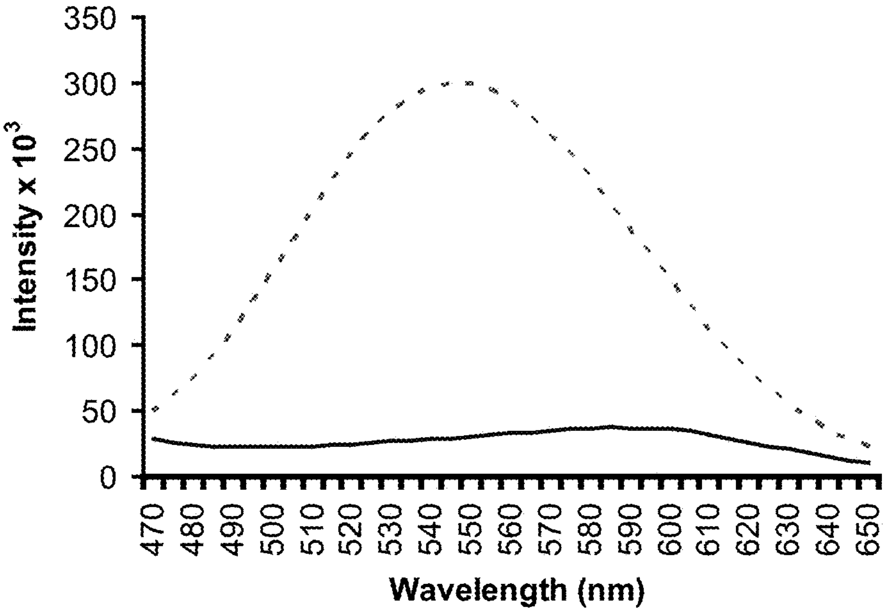
FIGS. 9A-F depict fluorescence excitation and emission spectra of Cmpds 27-31 and 33, respectively, in solution (solid lines) and in the presence of Aβ peptide (dashed lines).
Figure 9B:
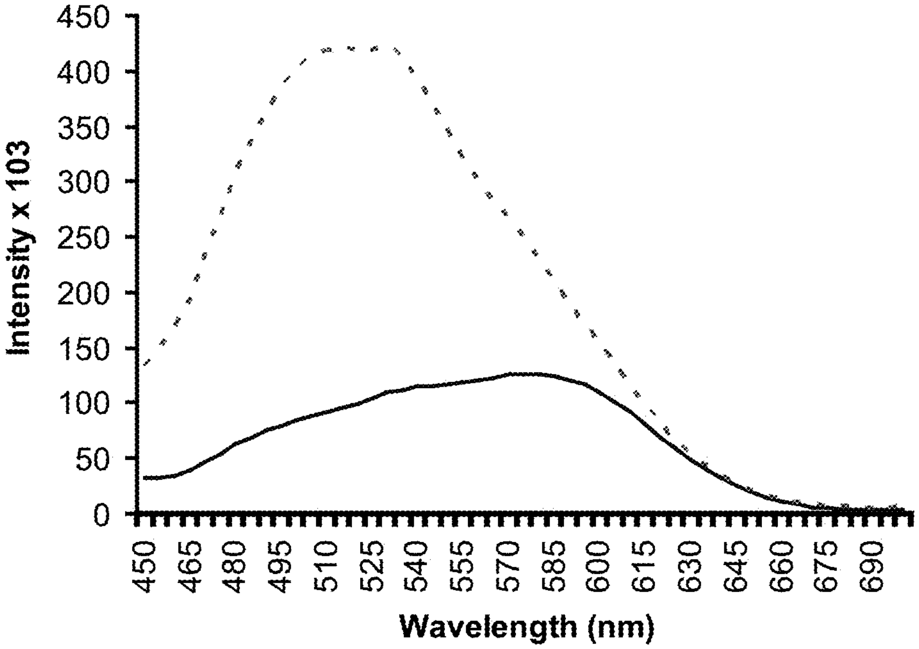
Figure 9C:
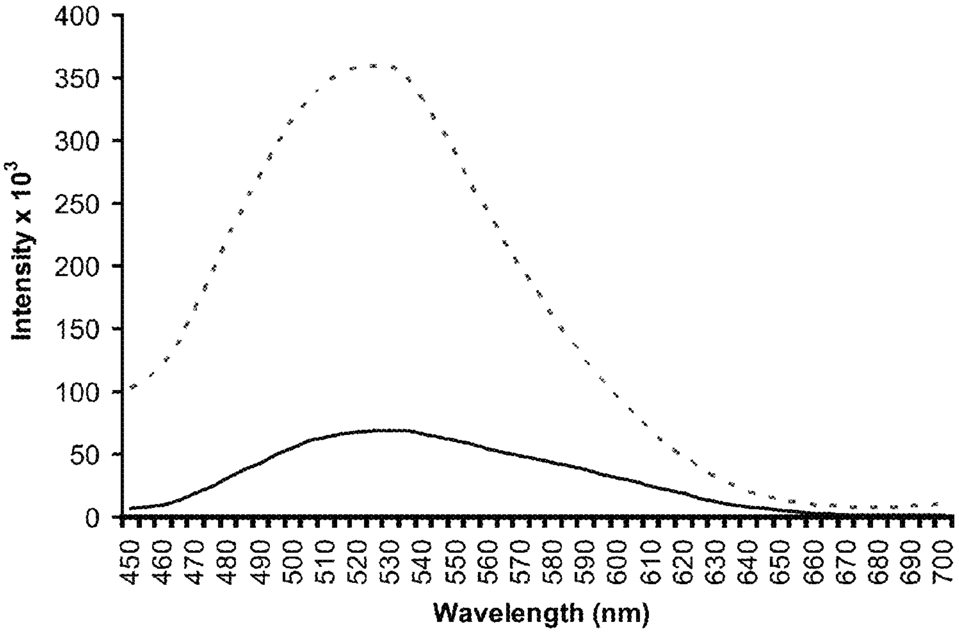
Figure 9D:
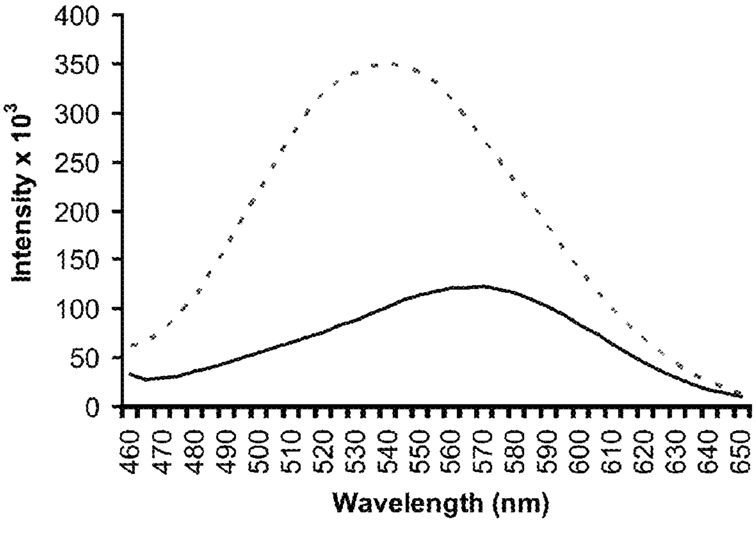
Figure 9E:
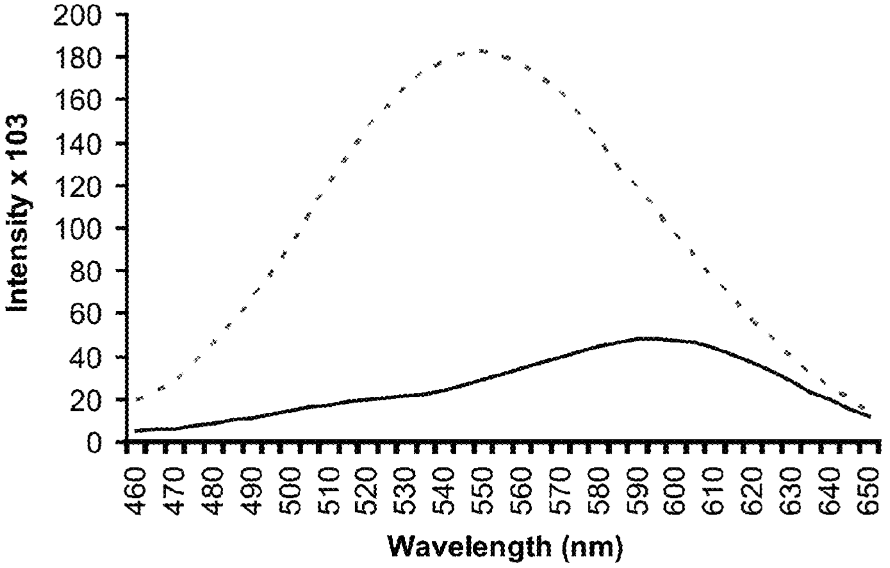
Figure 9F:
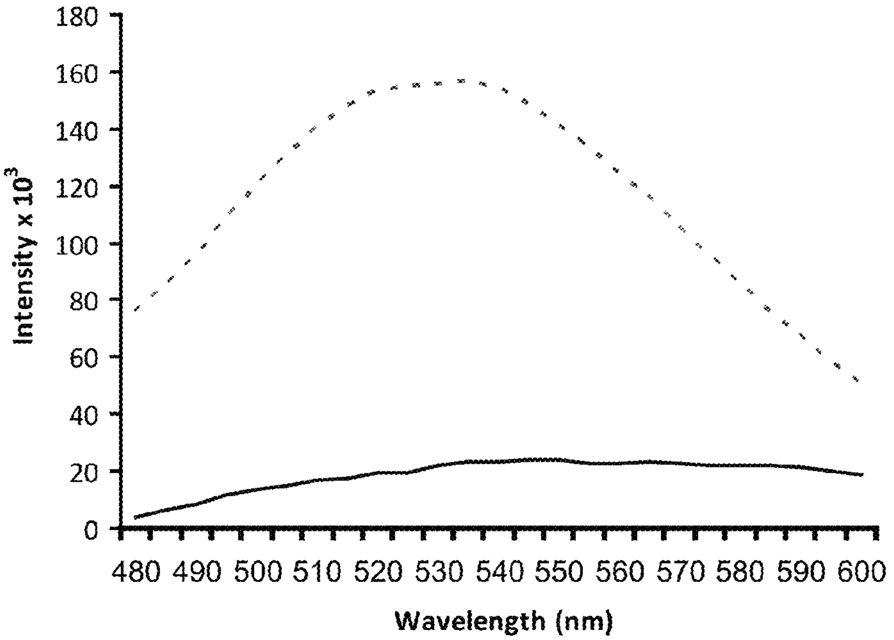
Figure 10A:
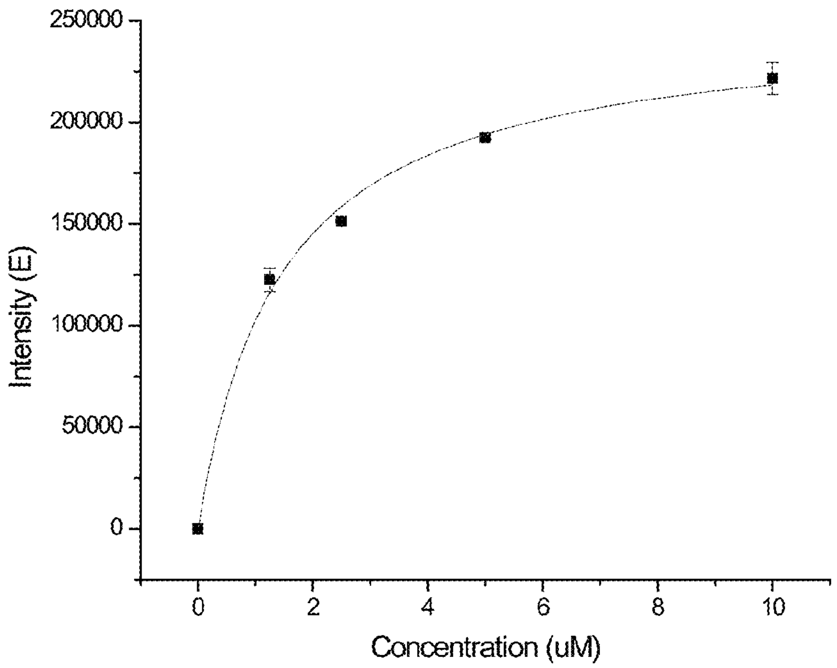
FIGS. 10A-F show fluorescence intensity versus concentration of aggregated Ab peptides for Cmpds 27-31 and 33, respectively.
Figure 10B:
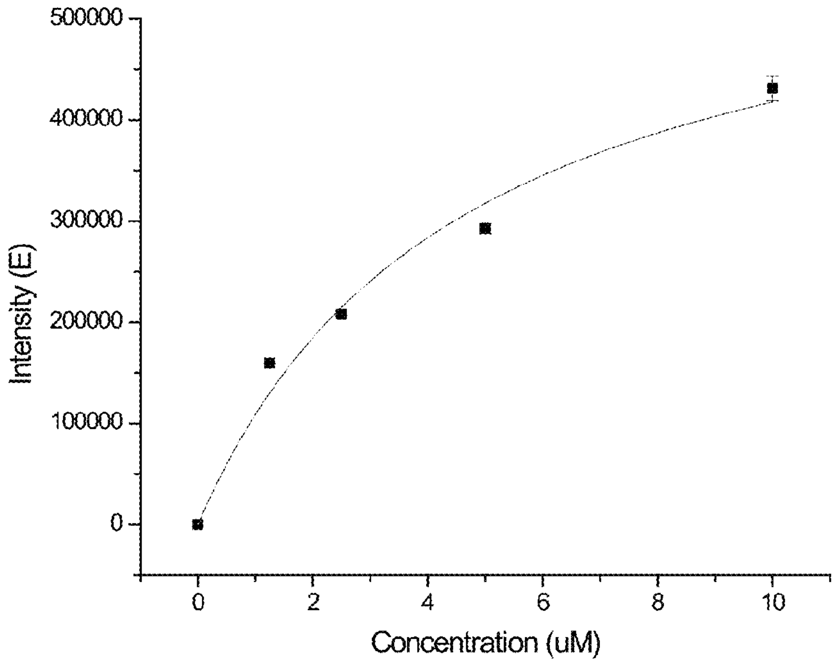
Figure 10C:
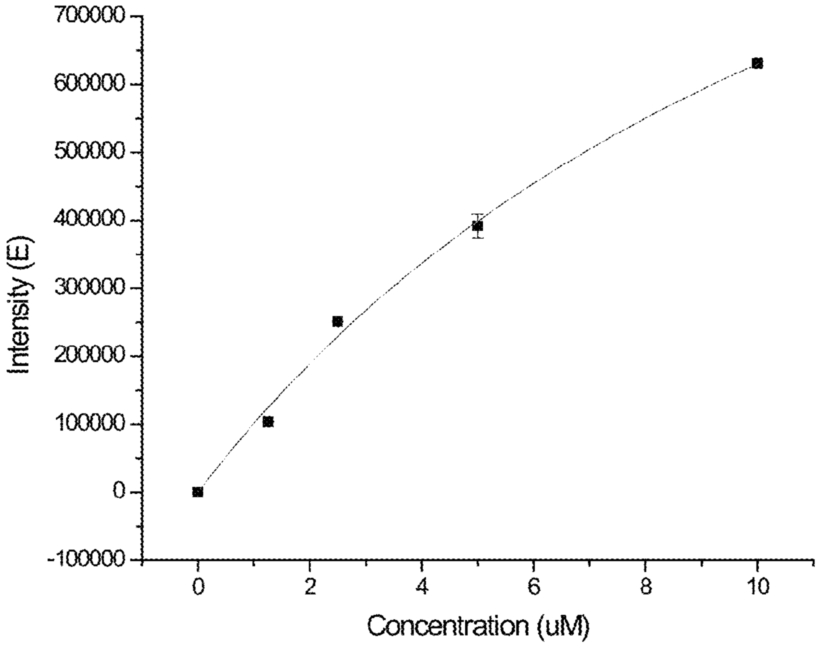
Figure 10D:
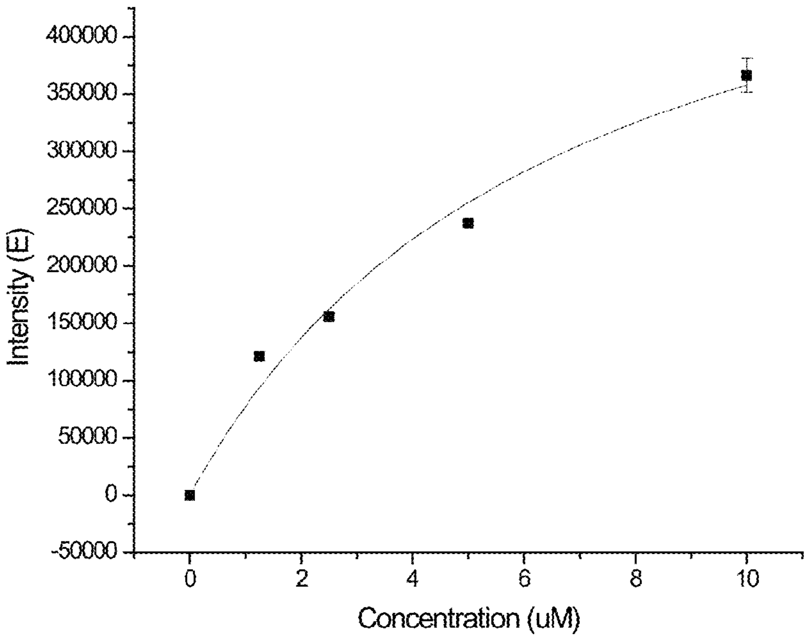
Figure 10E:
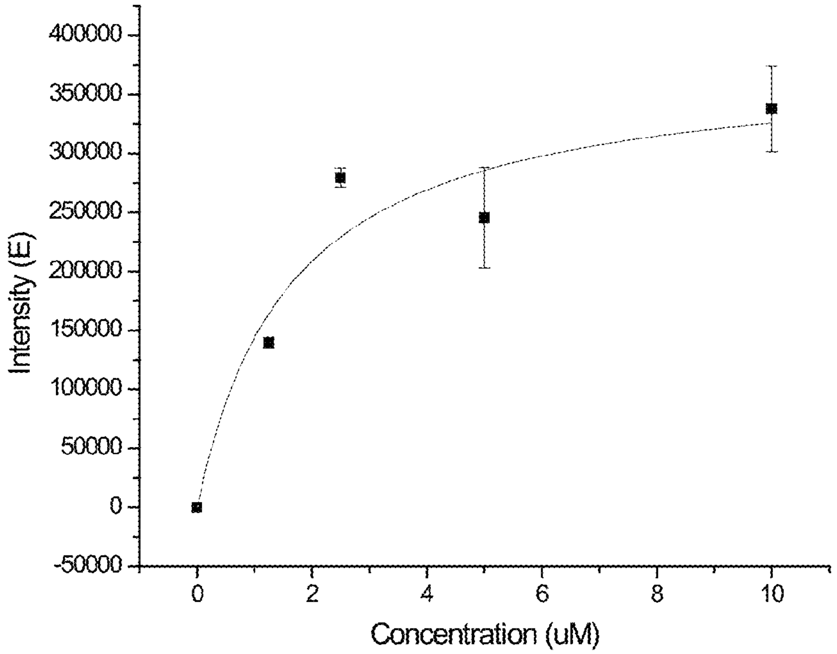
Figure 10F:
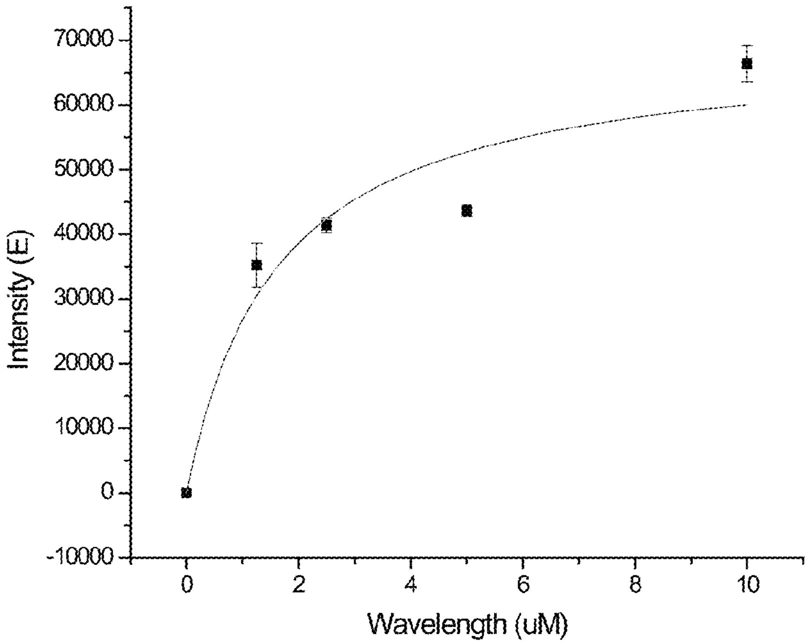
Figure 11A:
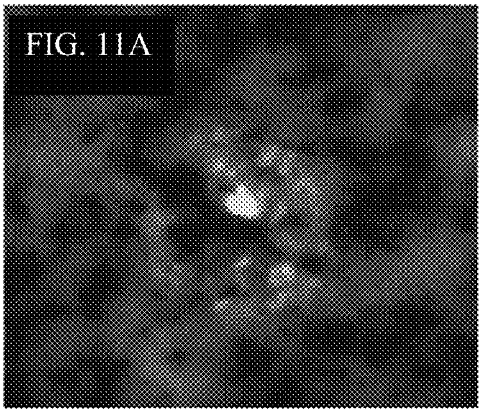
FIGS. 11A-F shows images of plaques that were stained with FIG. 11 A) compound 27, FIG. 11 B) compound 28, FIG. 11 C) compound 29, FIG. 11 D) compound 30, FIG. 11 E) compound 31, or FIG. 11 F) compound 33, as described herein.
Figure 11B:
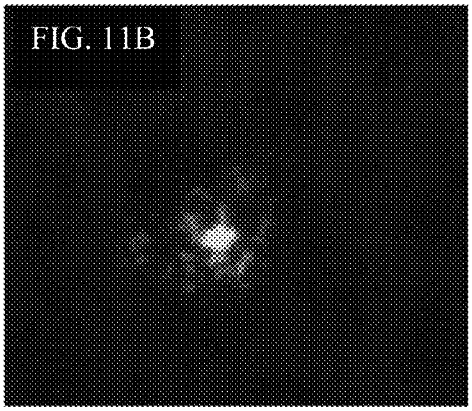
Figure 11C:
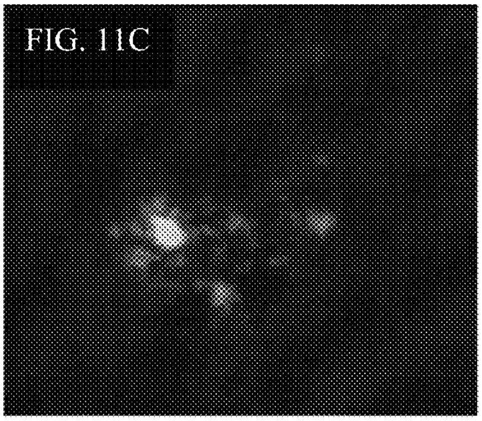
Figure 11D:
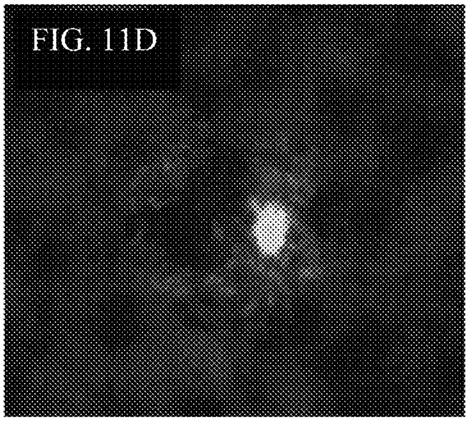
Figure 11E:
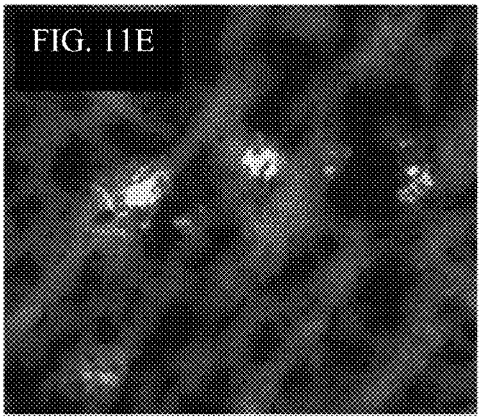
Figure 11F:
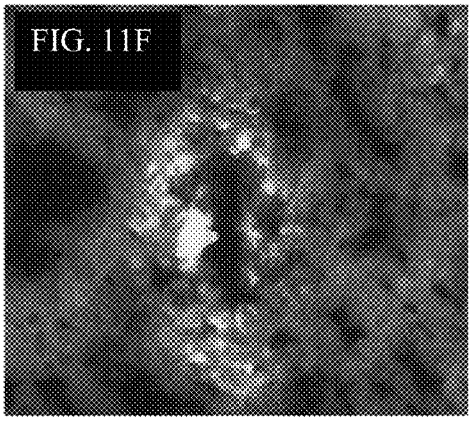

In principle, an amyloid-binding probe displays significant increase of the fluorescent emission upon binding with the aggregates as compared to that in solution. LeVine III, H., *Protein Sci.* 1993, 2, (3), 404-410. Along these lines, we compared the fluorescent properties of 27-31 or 33 in aqueous solution with or without the presence of aggregated Aβ42 peptides. Specifically, we measured the fluorescent properties of each dye at 4 μM concentration in nano pure water, before and after mixing with aggregated Aβ42 peptide (final concentration peptide=5 μM). As it is shown in table 5, in all cases we observed a significant increase (3 to 9-fold) in the intensity of the emission spectra of the probes upon association with the aggregated amyloid peptides. This intensity increase was also accompanied with a blue shift in the emission spectra of around 5-50 nm. After binding, all compounds had excitation maxima between 380-430 nm and their emission maxima were between 525-545 nm, suggesting that small changes in the donor or acceptor part of the molecule do not alter significantly their fluorescent maxima. However, compounds 27, 31 and 33, that possess piperidine as the electron donor, showed higher increase in fluorescence intensity after binding (7.7-, 8.3- and 7.2-fold, respectively) compared to probes containing piperazine, morpholine, or morpholino-ethanamine as electron donors. FIG. 9C provides a representative example of the fluorescent properties of compound 29. The figure shows fluorescent emission of compound 29 before (solid line) and after (dotted line) mixing with Aβ aggregates.

We also measured the apparent binding constants ($K_d$) of the probes to aggregated Aβ42 peptides. The fluorescent intensity of each probe was measured in concentrations of 1.25, 2.5, 5.0 and 10 μM in nano-pure water, mixed with 5 μM of the pre-aggregated Aβ42 peptides. Zhao, X.; Yang, J., *ACS Chem. Neurosc.* 1, (10), 655-660. In all cases the $K_d$ values were at the μM level with compounds 27, 31 and 33 exhibiting the highest affinity to aggregated Aβ peptides. The data from these binding studies suggests that small chemical modifications within the water-solublizing region of the ANCA motif do not significantly affect the binding of the probes to Aβ aggregates (compounds 27, 31 and 33). On the other hand, a decrease of the $K_d$ value was observed upon chemically altering the electron donor of the ANCA scaffold. As shown in table 5, compounds having piperidine as the electron donor are found to have lower $K_d$ values (1.4-1.6 μM) compared to those possessing piperazine, morpholine, or morpholino-ethanamine as electron donor (compounds 28, 29 and 30 respectively). FIGS. 10A-F show plots of the fluorescence intensity (at λ=525 nm) of compounds 27-31 and 32, respectively, as a function of the concentration in the presence of aggregated Aβ42 peptides (5 μM) in solution. As an example, fitting this data for compound 29 revealed a $K_d$ of 13.8 μM for association of compound 29 to aggregated Aβ42 peptides.

Finally, the lipophilicity (log P) of the synthesized probes was calculated. All compounds were found to have log P values between 2.53 and 3.81, suggesting that most of them fulfill the solubility criteria and can potentially cross the blood brain barrier. Lipinski, C. A.; Lombardo, F.; Dominy, B. W.; Feeney, P. J., *Adv. Drug Delivery Rev.* 1997, 23, (1-3), 3-25.

Example 6

Determination of Binding Constants for Compounds Described Herein

Pre-aggregated Aβ(1-42) (5 μM final concentration) was mixed with various concentrations of compounds described herein (10, 5, 2.5, 1.25 μM) in PBS buffer (pH 7.4) and their fluorescence was measured. The negative inverse of the x-intercept of the linear regression, that was drawn between the double reciprocal of the fluorescence intensity maximum and concentration of the compound, represents the compound binding constant ($K_d$) to Aβ(1-42).

Example 7

Determination of $K_d$ from Fluorescence Method

In order to quantify the dissociation constants ($K_d$'s) for the binding of fluorescent compounds with aggregated β-amyloid peptides, we used the method described by LeVine (see H. LeVine III, *Protein Sci.* 1993, 2, 404-410). This method is similar to the method described by Benesi-Hildebran (see C. Yang, L. Liu, T. W. Mu, Q. X. Guo, *Anal. Sci.* 2000, 16, 537-539). Here, the fluorescence of the compound was measured with and without the addition of the aggregated peptides in solution. The relative fluorescence enhancement of the compound upon binding to aggregated β-amyloid peptides was determined by taking the difference between F (fluorescence after the addition of aggregated peptides) and F (fluorescence before the addition of aggregated peptides).

In order to estimate the binding constant ($K_d$) for the compound-Aβ complexes from the fluorescence studies, we made the following assumptions:

1. All compounds are completely in solution and free of any significant competing binding process such as self-aggregation.
2. The concentration of unbound compounds can be approximated as close to the total concentration of the compounds.
3. The binding sites in the aggregated Aβ peptides are not completely occupied at the concentration of Aβ-binding compounds used for the fluorescence studies (i.e., the experiments are carried out under non-saturated binding conditions).

According to the Beer-Lambert law (see J. W. Robinson, "Atomic spectroscopy", 1996), one can obtain two expressions that relate the concentration of bound compound ([HG]), free compound ([G]), and free amyloid peptides ([H]) with either 1) the measured fluorescence of the compound in solution before the addition of the aggregated peptides ($F_O$), or 2) the measured fluorescence of the compound in the presence of the amyloid peptides (F):

$$F_O=\epsilon_G l[G_O] \quad (1)$$

$$F=\epsilon_{HG} l[HG]+\epsilon_H l[H]+\epsilon_G l[G] \quad (2)$$

where $[G_O]$=total concentration of compound $\epsilon_G$=absorption coefficient of G

[G]=unbound compound concentration $\epsilon_{HG}$=absorption coefficient of HG

[HG]=compound-Aβ complex concentration $\epsilon_H$=absorption coefficient of H $[H_O]$=total concentration of aggregated peptide l=path length

[H]=unbound aggregated peptide concentration.

Substituting $[G_O]$=[G]+[HG] into equation 1, and making the approximation that $\epsilon_{HG}$l[HG]+$\epsilon_G$l[G]>>$\epsilon_H$l[H], one can arrive at a simplified expression for the relative fluorescence of bound compound (ΔF):

$$\Delta F=F-F_O=\epsilon_{HG} l[HG]+\epsilon_G l[G]-\epsilon_G l[G]-\epsilon_G l[HG] \quad (3)$$

or $$\Delta F=\Delta\epsilon l[HG] \quad (4)$$

where $\Delta\epsilon=\epsilon_{HG}-\epsilon_G$.

In order to obtain a relationship between the change in measured fluorescence of the compound (ΔF) with the binding constant of the compound to aggregated β-amyloid peptides ($K_d$'s), we used the standard equation for a binding isotherm to obtain a relationship between [HG] and $K_d$:

$$[HG]=\frac{[H_O][G]}{K_d+[G]} \quad (5)$$

Combining equation 4 and 5, we obtained a relationship between ΔF and $K_d$:

$$\Delta F=\frac{[H_O][G]}{K_d+[G]}\Delta\mathcal{E}l \quad (6)$$

In order to estimate the $K_d$ of the compound bound to aggregated Aβ peptides from the measured change in fluorescence, we take the reciprocal of the equation 6 to give:

$$\frac{1}{\Delta F}=\frac{K_d}{\Delta\mathcal{E}l[H_O]}\frac{1}{[G]}+\frac{1}{\Delta\mathcal{E}l[H_O]} \quad (7)$$

Figure 6:
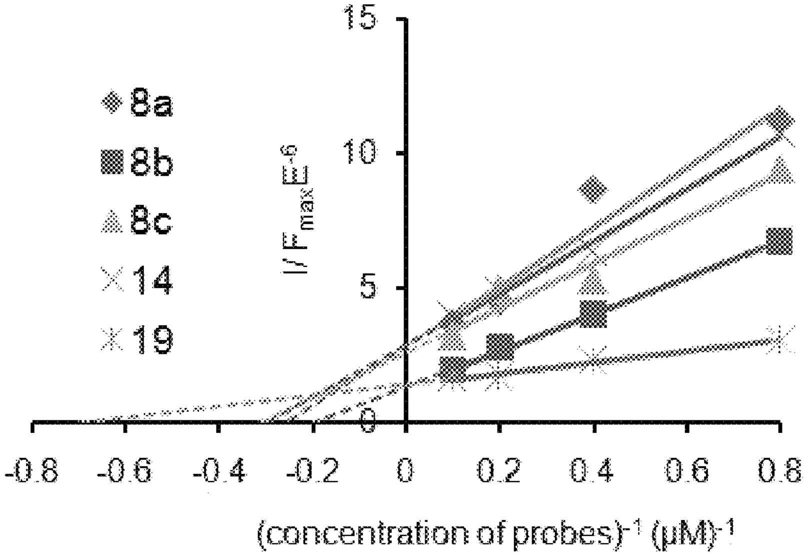
FIG. 6 depicts a double reciprocal plot of fluorescence maxima and concentration of Cmpds 8a, 8b, 8c, 14 and 19, as described herein. Legend: Cmpd 8a (diamond); Cmpd 8b (box); Cmpd 8c (triangle); Cmpd 14 (cross); Cmpd 19 (barred cross).
Figure 7A:
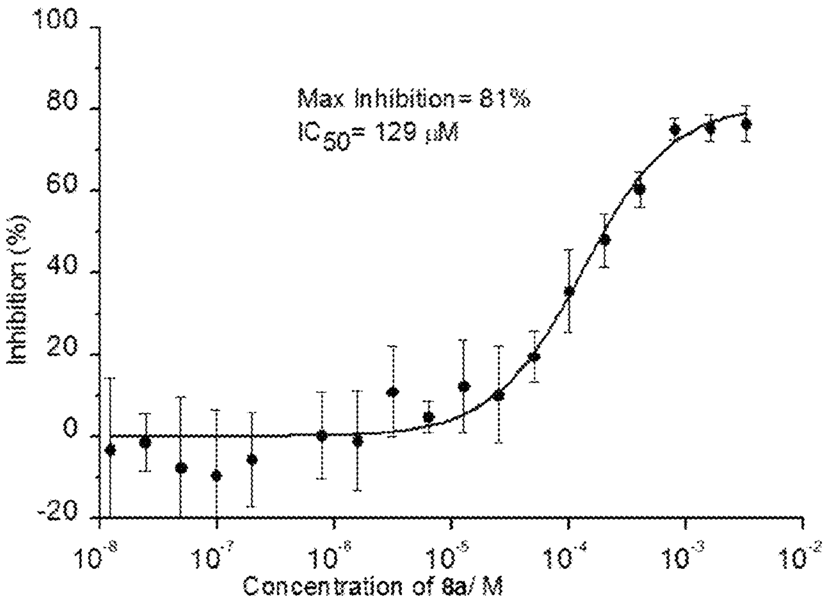
FIGS. 7A-D depict inhibition maxima and $1E_{50}$ values for compounds described herein.
Figure 7B:
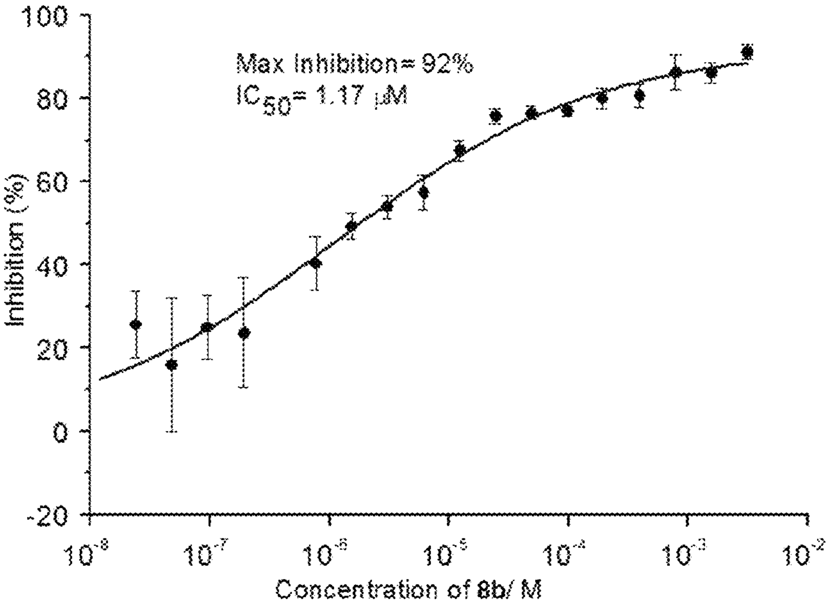
Figure 7C:
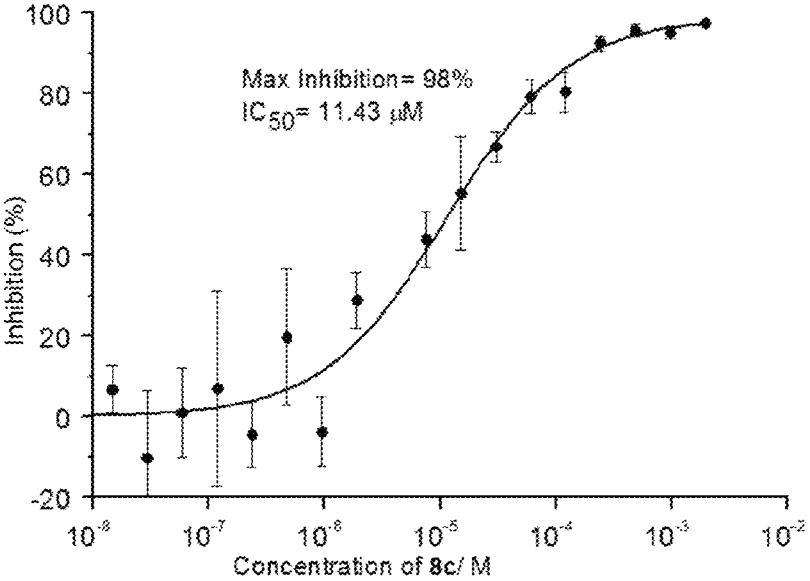
Figure 7D:
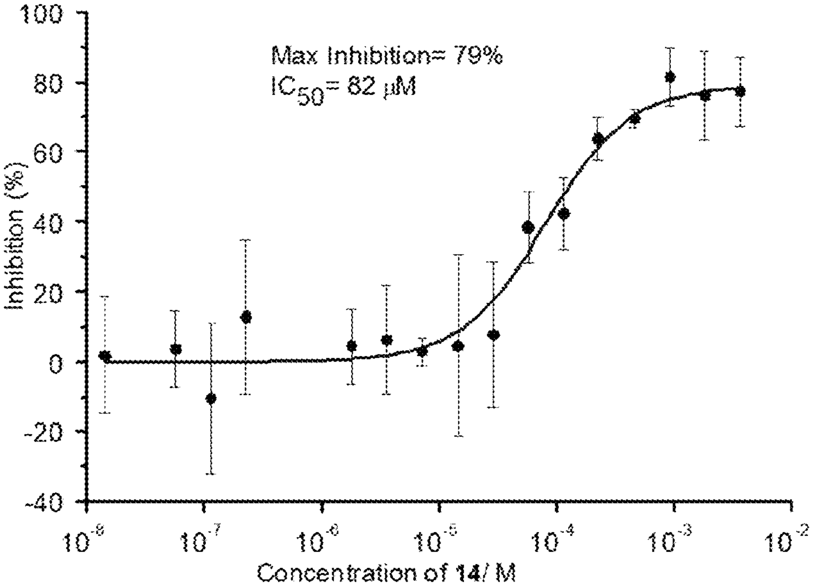

Equation 7 suggests that a double reciprocal plot of ΔF and [G] should yield a straight line with x-intercept equal to $-1/K_d$. FIG. 2 and FIG. 6 provide double reciprocal plots of the measured fluorescence versus total concentration of compound $[G_O]$. Assuming that [G] can be approximated as close to $[G_O]$ (assumption 2), we can obtain estimates for the $K_d$'s of the compound-Aβ complexes from the x-intercept of the linear fits of the data for each compound. The estimated $K_d$'s for some compounds described herein are given in Table 3.

Example 8

ELISA Assay

Aggregated Aβ peptides were generated from synthetic Aβ(1-42) peptides by dissolving 30 μg of peptide in 90 μL of nanopure water (pH 5-6) and incubating at 37° C. for ≥72 h without agitation. Each well of a 96-well plate (well volume 0.4 mL; clear, flat bottom polypropylene) was coated for 3 h at 25° C. with 50 μL of 1.3 μM solution of Aβ peptides in phosphate-buffered saline (PBS, 10 mM $NaH_2PO_4/Na_2HPO_4$, 138 mM NaCl, 2.7 mM KCl, pH 7.4). After removal of the excess sample, 50 μL solutions of compounds in PBS buffer (various concentrations were obtained by diluting a stock solution with PBS buffer) were incubated in the wells for 12 h. Compounds that did not dissolve in PBS buffer were dissolved in DMSO and diluted in PBS buffer to give a final solution of 5% DMSO in PBS buffer. The excess solutions were then removed and all wells were blocked for 30 min by adding 300 μL of a 1% (w/v) solution of bovine serum albumin in PBS buffer (BSA/PBS). On occasion, an additional blocking step was performed prior to incubation with solutions of small molecules. The blocking solution was discarded and the wells were washed once with 300 μL of PBS buffer. Wells were incubated for 1 h with 50 μL of a 1.1 nM solution (in 1% BSA/PBS, dilution 1:6000) of anti-Aβ IgG (clone 6E10, monoclonal, mouse), followed by removal of the solution. The wells were washed twice with 300 μL of PBS buffer and incubated for 60 min with 50 μL of the secondary IgG (anti-mouse IgG H+L, polyclonal, rabbit) conjugated with alkaline phosphatase (6.8 nM in 1% BSA/PBS, dilution 1:1000). The solution was discarded, and the wells were washed twice with 300 μL PBS buffer. Bound secondary IgGs were detected by the addition of 50 μL of a p-nitrophenyl phosphate solution (2.7 mM, in 100 mM diethanol amine/0.5 mM magnesium chloride, pH 9.8). Absorbance intensities were determined at 405 nm using a UV-vis spectroscopic plate reader (Sprectramax 190, Molecular Devices, Sunnyvale, Calif.). Each run was performed five times and averaged. Error bars represent standard deviations. Graphs were plotted and fitted with the sigmoid curve fitting.

Example 9

Fluorescence Studies with Monomeric Aβ

Aβ (Biopeptide, Inc.) was initially solubilized in hexafluoroisopropanol at 1 mM concentration, vortexed, sonicated and vortexed. The vial was covered in foil and was incubated for 21 hours at 25° C. on a shaker, with 3 times of vortexing throughout the incubation period. The solution was sonicated and vortexed again then diluted with cold nanopure water (2:1 $H_2O$:HFIP), fractionated in desired amounts into small glass vials, and immediately frozen in a $CO_2$/acetone bath. Each fraction was covered with parafilm that was punctured to allow solvent vapors to escape. The fractions were lyophilized for 2 days to obtain monomeric Aβ (91% monomer by 12% Tris-bis PAGE gel analysis). 1.8 μL (8.42 μM) of this monomeric Aβ(1-42) was added to 3 μL of 4 μM concentration of small molecules that was prepared by dissolving in PBS buffer pH 7.4 to attain a final concentration of 5 μM of Aβ(1-42) and 4 μM of the compound. The solution was transferred to 3 mL cuvettes and the fluorescence was measured at 25° C.

Example 10

Evaluation of Rigid Rotors for Cytotoxic Activity Against SHSY-5Y Human Neuroblastoma Cells (MTT Assay)

Figure 8:
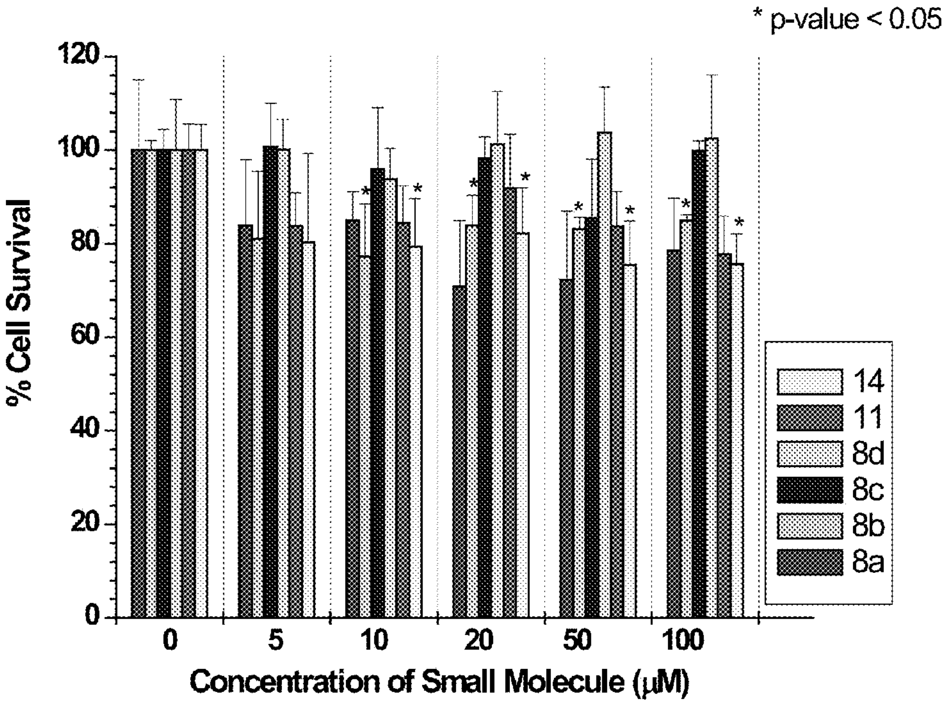
FIG. 8 depicts the results of cytoxicity studies as described herein. Legend: for each concentration of compound employed in the cytoxicity assay, the % cell survival is plotted as a histogram in the order (left to right): Cmpd 8a, 8b, 8c, 8d, 11 and 14, respectively.

SHSY-5Y human neuroblastoma cells, MTT (3-(4,5-dimethylthiazol-2-yl)-2,5-diphenyltetrazolium bromide) cell proliferation kit, Eagle's Minimum Essential Medium (EMEM), Ham's F12 nutrient mixture, and Fetal Bovine Serum (FBS) were all purchased from ATCC (Manassas, Va.). Briefly, SH-SY5Y cells (in 1:1 EMEM:Ham's F-12 with 10% FBS) were seeded on 96-well plates at a density of $5\times10^4$ cells/well. Plates were incubated overnight (in a humidified atmosphere of 95% air, 5% $CO_2$, at 37° C.) to promote attachment of cells to the wells. Cells were then treated with various concentrations of compound 8a, 8b, 8c, 8d, 11, or 14 and incubated for 24 hours (humidified atmosphere of 95% air, 5% $CO_2$, at 37° C.). MTT reagent (20 μL) was added to the medium and incubated for additional 4 hours. After incubation, 100 μL of detergent reagent was added and the plates were covered with aluminum foil and left at room temperature overnight. The amount of solubilized MTT formazan was measured by spectrophotometric absorbance at 570 nm (Spectramax 190, Molecular Devices, Sunnyvale, Calif.). MTT assay was not performed on compound 19 due to its poor solubility in aqueous media. All data are presented as the mean±S.D, N=3 for each concentration. The Student's t-test was employed for all analyses. A p-value of <0.05 was considered statistically significant compared to control cells. As shown in FIG. 8, all compounds showed little or no cytotoxicity against human neuroblastoma cells at concentrations up to 100 μM. These properties represent significant advantages for further in vivo evaluation.

Example 11

Imaging Human Tissue with Amyloid Binding Compounds

FIGS. 11A-F depict fluorescence images of amyloid plaques in human tissue from AD cases. After the frozen tissue was sectioned and mounted to a glass slide, the tissue was exposed to a solution containing a fluorescent probe for 30 min. The sample was washed with water to eliminate non-specific staining of the tissue, and imaged using an inverted epi-fluorescence microscope. The images reveal the location of plaques that were stained with A) compound 27, B) compound 28, C) compound 29, D) compound 30, E) compound 31, or F) compound 33.

What is claimed is:

1. A method of detecting an amyloid peptide, the method comprising:

(i) contacting an amyloid peptide with a compound having the structure of formula (I), or a pharmaceutical acceptable salt thereof, thereby forming a detectable amyloid complex; and (ii) detecting said detectable amyloid complex;

wherein formula (I) has the structure:

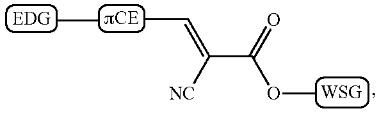

wherein

EDG is an electron donor group;

πCE is a pi-conjugation element; and

WSG is a water soluble group;

wherein said EDG is $R^1$-substituted or unsubstituted alkyl, $R^1$-substituted or unsubstituted cycloalkyl, $R^1$-substituted or unsubstituted heteroalkyl, $R^1$-substituted or unsubstituted heterocycloalkyl, $R^1$-substituted or unsubstituted aryl, $R^1$-substituted or unsubstituted heteroaryl, $—OR^2NR^4C(O)R^3$, $—NR^4R^5$, $—SR^6$, or $—PR^7R^8$, wherein $R^1$ is halogen, $—OR^9$, $—NR^{10}R^{11}$, unsubstituted alkyl, unsubstituted heteroalkyl, unsubstituted cycloalkyl, unsubstituted heterocycloalkyl, unsubstituted aryl, or unsubstituted heteroaryl;

$R^2$, $R^3$, $R^4$, $R^5$, $R^6$, $R^7$ and $R^8$ are independently hydrogen, $R^{12}$-substituted or unsubstituted alkyl, $R^{12}$-substituted or unsubstituted heteroalkyl, $R^{12}$-substituted or unsubstituted cycloalkyl, $R^{12}$-substituted or unsubstituted heterocycloalkyl, $R^{12}$-substituted or unsubstituted aryl or $R^{12}$-substituted or unsubstituted heteroaryl, wherein $R^4$ and $R^5$ are optionally joined together to form an $R^{12}$-substituted or unsubstituted heterocycloalkyl, or $R^{12}$-substituted or unsubstituted heteroaryl;

$R^9$, $R^{10}$ and are independently hydrogen, $R^{12}$-substituted or unsubstituted alkyl, $R^{12}$-substituted or unsubstituted heteroalkyl, $R^{12}$-substituted or unsubstituted cycloalkyl, $R^{12}$-substituted or unsubstituted heterocycloalkyl, $R^{12}$-substituted or unsubstituted aryl, or $R^{12}$-substituted or unsubstituted heteroaryl, wherein $R^{10}$ and are optionally joined together to form an $R^{12}$-substituted or unsubstituted heterocycloalkyl, or $R^{12}$-substituted or unsubstituted heteroaryl;

$R^{12}$ is halogen, $—OR^{13}$, $—NR^{14}R^{15}$, $R^{16}$-substituted or unsubstituted alkyl, $R^{16}$-substituted or unsubstituted heteroalkyl, $R^{16}$-substituted or unsubstituted cycloalkyl, $R^{16}$-substituted or unsubstituted heterocycloalkyl, $R^{16}$-substituted or unsubstituted aryl, or $R^{16}$-substituted or unsubstituted heteroaryl;

$R^{13}$, $R^{14}$ and $R^{15}$ are independently hydrogen or unsubstituted alkyl; and $R^{16}$ is unsubstituted alkyl, unsubstituted heteroalkyl, unsubstituted cycloalkyl, unsubstituted heterocycloalkyl, unsubstituted aryl, or unsubstituted heteroaryl;

wherein said pi-conjugation element has the formula:

$$-L^1-(A^1)_q-L^2-(A^2)_r-L^3- \text{ or } -L^1-(A^1)_q-L^4-A^3-L^2-(A^2)_r-L^3-,$$

wherein q and r are independently 0 or 1, wherein at least one of q or r is 1;

$A^1$, $A^2$ and $A^3$ are independently $R^{17}$-substituted or unsubstituted arylene or $R^{17}$-substituted or unsubstituted heteroarylene;

$L^1$, $L^2$, $L^3$ and $L^4$ are independently a bond or a linking group having the formula:

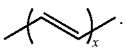

wherein x is an integer from 1 to 50;

$R^{17}$ is halogen, $—OR^{18}—NR^{19}R^{20}$, $R^{21}$-substituted or unsubstituted alkyl, $R^{21}$-substituted or unsubstituted heteroalkyl, $R^{21}$-substituted or unsubstituted cycloalkyl, $R^{21}$-substituted or unsubstituted heterocycloalkyl, $R^{21}$-substituted or unsubstituted aryl, or $R^{21}$-substituted or unsubstituted heteroaryl;

$R^{18}$, $R^{19}$ and $R^{20}$ are independently hydrogen, $R^{21}$-substituted or unsubstituted alkyl, $R^{21}$-substituted or unsubstituted heteroalkyl, $R^{21}$-substituted or unsubstituted cycloalkyl, $R^{21}$-substituted or unsubstituted heterocycloalkyl, $R^{21}$-substituted or unsubstituted aryl, or $R^{21}$-substituted or unsubstituted heteroaryl;

$R^{21}$ is halogen, —$OR^{22}$, —$NR^{23}R^{24}$, unsubstituted alkyl, unsubstituted heteroalkyl, unsubstituted cycloalkyl, unsubstituted heterocycloalkyl, unsubstituted aryl, or unsubstituted heteroaryl;

$R^{22}$, $R^{23}$ and $R^{24}$ are independently hydrogen or unsubstituted alkyl; and wherein said water soluble group is $R^{25}$-substituted or unsubstituted alkyl, $R^{25}$-substituted or unsubstituted heteroalkyl, $R^{25}$-substituted or unsubstituted cycloalkyl, $R^{25}$-substituted or unsubstituted heterocycloalkyl, $R^{25}$-substituted or unsubstituted aryl, $R^{25}$-substituted or unsubstituted heteroaryl;

wherein $R^{25}$ is halogen, —$OR^{26}$, —$NR^{27}R^{28}$, $R^{29}$-substituted or unsubstituted alkyl, $R^{29}$-substituted or unsubstituted heteroalkyl, $R^{29}$-substituted or unsubstituted cycloalkyl, $R^{29}$-substituted or unsubstituted heterocycloalkyl, $R^{29}$-substituted or unsubstituted aryl, or $R^{29}$-substituted or unsubstituted heteroaryl;

$R^{26}$, $R^{27}$ and $R^{28}$ are independently hydrogen, $R^{29}$-substituted or unsubstituted alkyl, $R^{29}$-substituted or unsubstituted heteroalkyl, $R^{29}$-substituted or unsubstituted cycloalkyl, $R^{29}$-substituted or unsubstituted heterocycloalkyl, $R^{29}$-substituted or unsubstituted aryl, or $R^{29}$-substituted or unsubstituted heteroaryl, wherein $R^{27}$ and $R^{28}$ are optionally joined together to form an $R^{29}$-substituted or unsubstituted heterocycloalkyl, or $R^{29}$-substituted or unsubstituted heteroaryl;

$R^{29}$ is halogen, —$OR^{30}$, —$NR^{31}R^{32}$, unsubstituted alkyl, unsubstituted heteroalkyl, unsubstituted cycloalkyl, unsubstituted heterocycloalkyl, unsubstituted aryl, or unsubstituted heteroaryl; and $R^{30}$, $R^{31}$ and $R^{32}$ are independently hydrogen or unsubstituted alkyl.

2. The method of claim 1, wherein at least one of $A^1$ or $A^2$ is $R^{17}$-substituted or unsubstituted

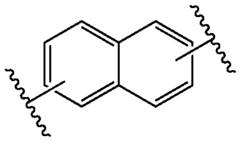 or 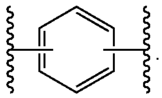.

3. The method of claim 1, wherein x is an integer from 1 to 10.

4. The method of claim 1, wherein said water soluble group is an ethylene glycol moiety having the formula:

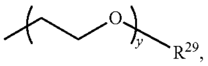

wherein y is an integer from 1 to 50.

5. The method of claim 4, wherein $R^{29}$ is unsubstituted alkyl.

6. The method of claim 1, wherein said compound has the structure:

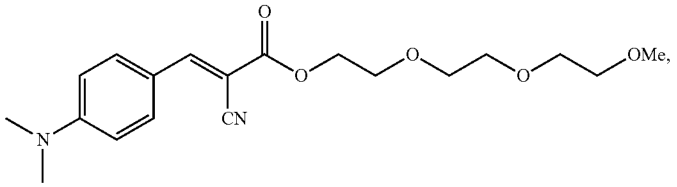

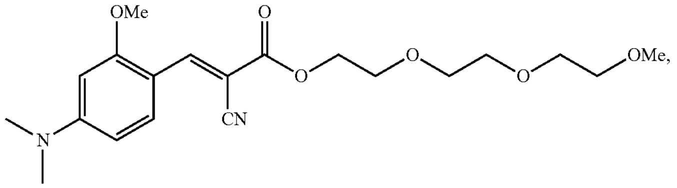

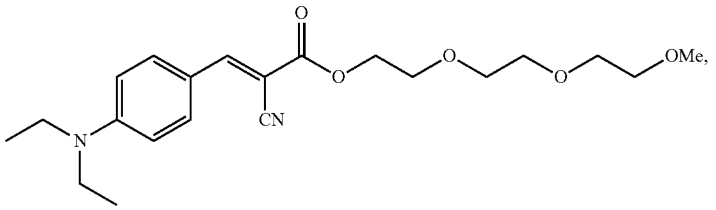

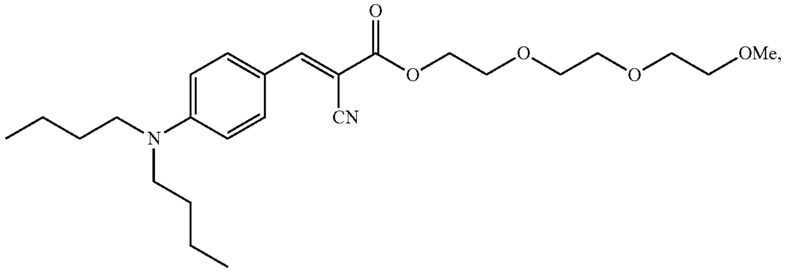

-continued
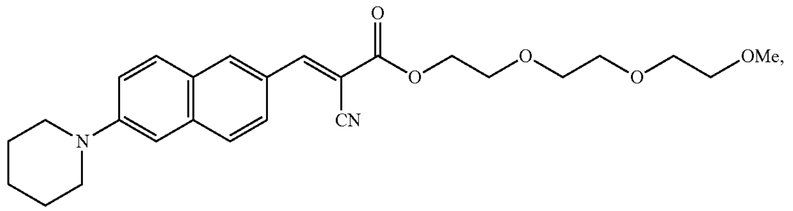
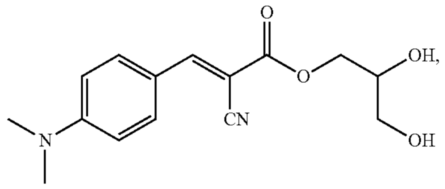
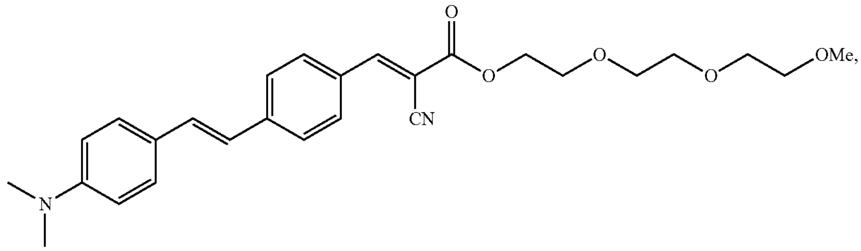
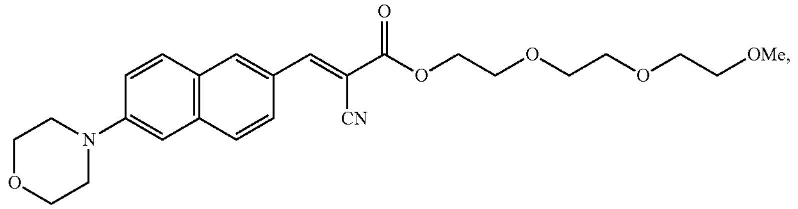
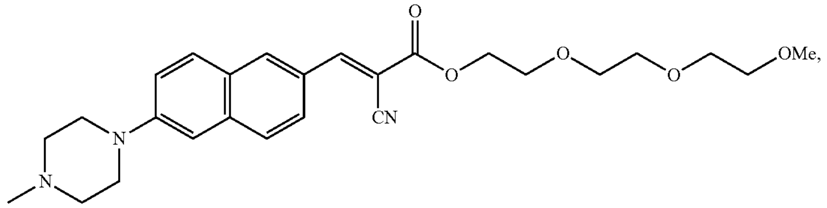
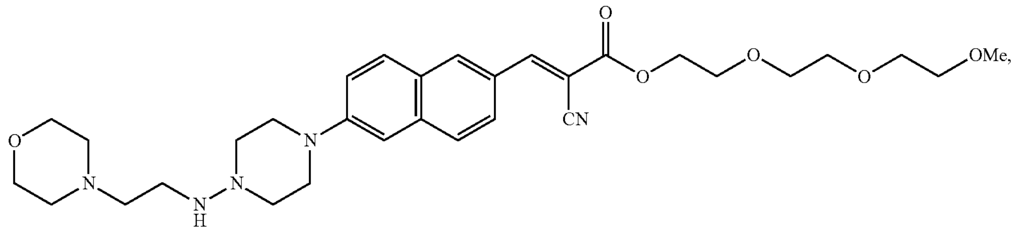

-continued

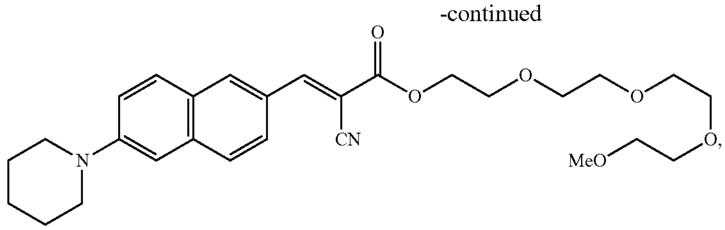

or

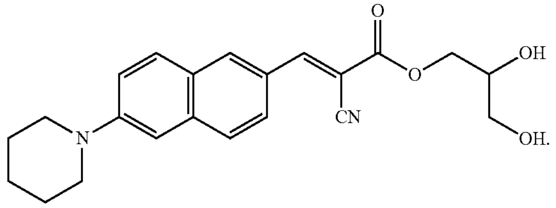

7. A method of detecting an amyloid peptide, the method comprising:

(i) contacting an amyloid peptide with a compound having the structure of formula (IVa) or formula (IVb), or a pharmaceutical acceptable salt thereof, thereby forming a detectable amyloid complex; and (ii) detecting said detectable amyloid complex;

wherein formula (IVa) has the structure:

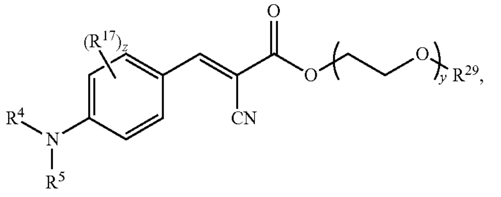

and formula (IVb) has the structure:

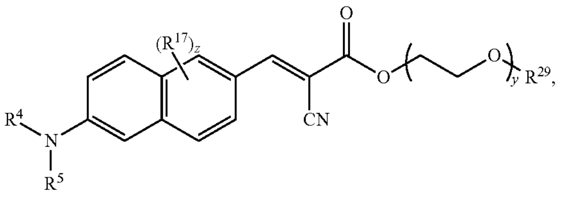

wherein $R^4$ and $R^5$ are independently hydrogen, $R^{12}$-substituted or unsubstituted alkyl, $R^{12}$-substituted or unsubstituted heteroalkyl, $R^{12}$-substituted or unsubstituted cycloalkyl, $R^{12}$-substituted or unsubstituted heterocycloalkyl, $R^{12}$-substituted or unsubstituted aryl or $R^{12}$-substituted or unsubstituted heteroaryl, wherein $R^4$ and $R^5$ are optionally joined together to form an $R^{12}$-substituted or unsubstituted heterocycloalkyl, or $R^{12}$-substituted or unsubstituted heteroaryl;

$R^{12}$ is halogen, —$OR^{13}$, —$NR^{14}R^{15}$, $R^{16}$-substituted or unsubstituted alkyl, $R^{16}$-substituted or unsubstituted heteroalkyl, $R^{16}$-substituted or unsubstituted cycloalkyl, $R^{16}$-substituted or unsubstituted heterocycloalkyl, $R^{16}$-substituted or unsubstituted aryl, or $R^{16}$-substituted or unsubstituted heteroaryl;

$R^{13}$, $R^{14}$ and $R^{15}$ are independently hydrogen or unsubstituted alkyl;

$R^{16}$ is unsubstituted alkyl, unsubstituted heteroalkyl, unsubstituted cycloalkyl, unsubstituted heterocycloalkyl, unsubstituted aryl, or unsubstituted heteroaryl;

$R^{17}$ is halogen, —$OR^{18}$, —$NR^{19}R^{20}$, $R^{21}$-substituted or unsubstituted alkyl, $R^{21}$-substituted or unsubstituted heteroalkyl, $R^{21}$-substituted or unsubstituted cycloalkyl, $R^{21}$-substituted or unsubstituted heterocycloalkyl, $R^{21}$-substituted or unsubstituted aryl, or $R^{21}$-substituted or unsubstituted heteroaryl;

$R^{18}$, $R^{19}$ and $R^{20}$ are independently hydrogen, $R^{21}$-substituted or unsubstituted alkyl, $R^{21}$-substituted or unsubstituted heteroalkyl, $R^{21}$-substituted or unsubstituted cycloalkyl, $R^{21}$-substituted or unsubstituted heterocycloalkyl, $R^{21}$-substituted or unsubstituted aryl, or $R^{21}$-substituted or unsubstituted heteroaryl;

$R^{21}$ is halogen, —$OR^{22}$, —$NR^{23}R^{24}$, unsubstituted alkyl, unsubstituted heteroalkyl, unsubstituted cycloalkyl, unsubstituted heterocycloalkyl, unsubstituted aryl, or unsubstituted heteroaryl;

$R^{22}$, $R^{23}$ and $R^{24}$ are independently hydrogen or unsubstituted alkyl;

$R^{29}$ is halogen, —$OR^{30}$, —$NR^{31}R^{32}$, unsubstituted alkyl, unsubstituted heteroalkyl, unsubstituted cycloalkyl, unsubstituted heterocycloalkyl, unsubstituted aryl, or unsubstituted heteroaryl;

$R^{30}$, $R^{31}$ and $R^{32}$ are independently hydrogen or unsubstituted alkyl;

y is an integer from 1 to 10; and z is an integer from 0 to 4 when the amyloid peptide is contacted with a compound having the structure of formula IVa, and is an integer from 0 to 6 when the amyloid peptide is contacted with a compound having the structure of formula IVb.

8. The method of claim 7, wherein said compound has the structure:

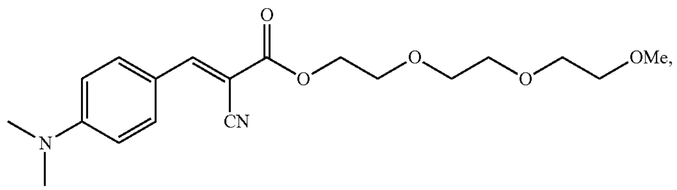
,
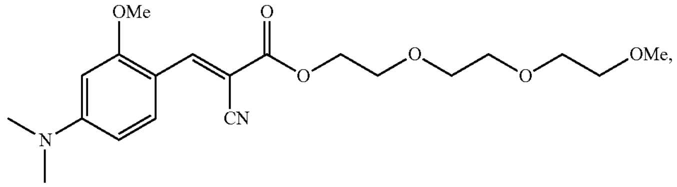
,
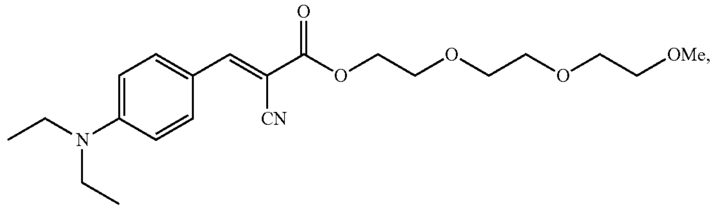
,
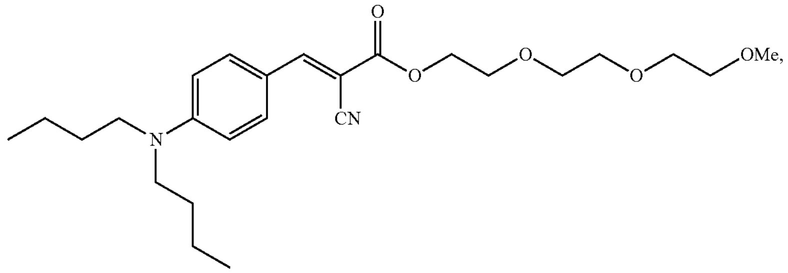
,
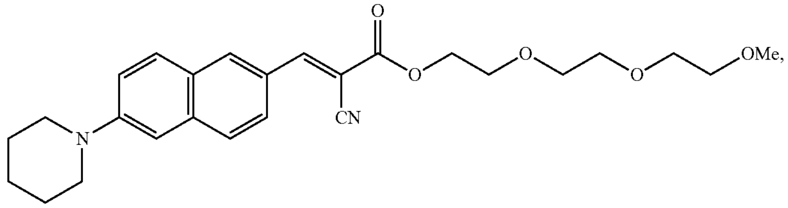 [SMILES: COCCOCCOCCOC(=O)/C(C#N)=C/c1ccc2cc(N3CCCCC3)ccc2c1]
,
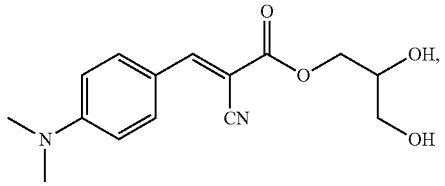
,
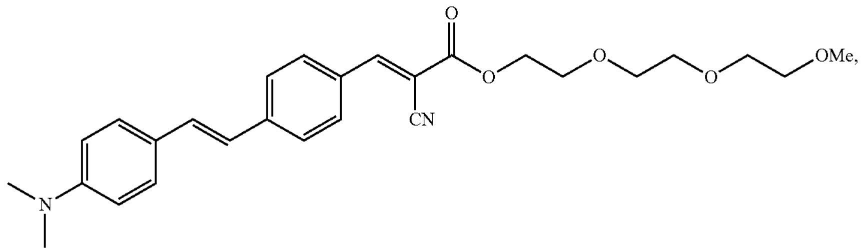
, -continued

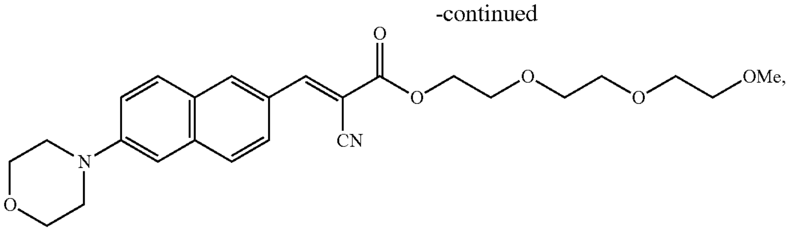

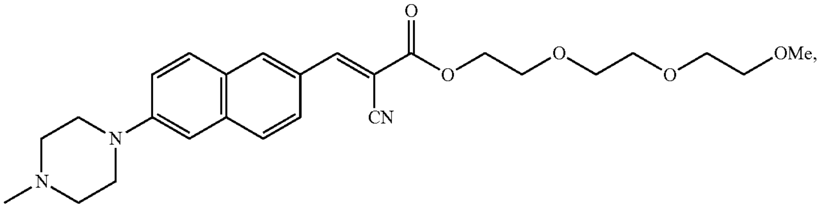

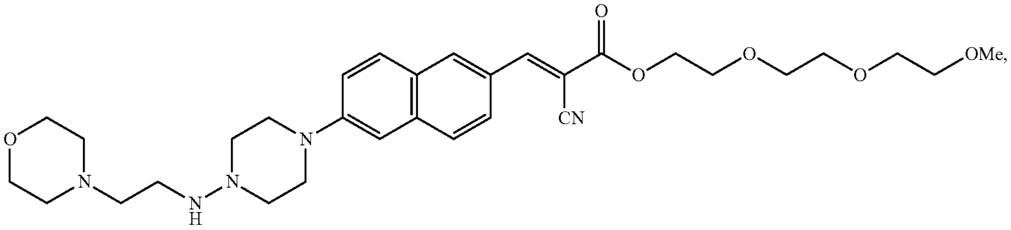

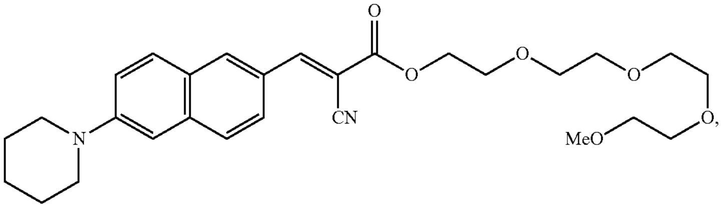

or

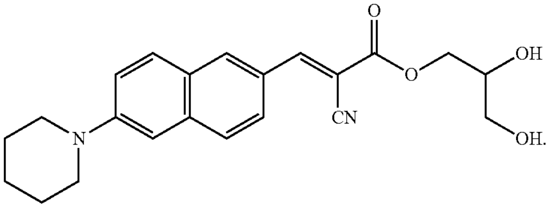

9. The method of claim 7, wherein $R^4$ and $R^5$ are optionally joined together to form an $R^{12}$-substituted or unsubstituted heterocycloalkyl.

10. The method of claim 7, wherein said $R^{12}$-substituted or unsubstituted heterocycloalkyl is a substituted or unsubstituted piperidinyl.

11. The method of claim 7, wherein y is 2 and z is 0.

12. The method of claim 1, wherein said amyloid peptide is Aβ peptide, prion, protein, α-synuclein, or superoxide dismutase.

13. The method of claim 12, wherein said amyloid peptide forms part of an amyloid.

14. The method of claim 1, wherein said compound has the structure:

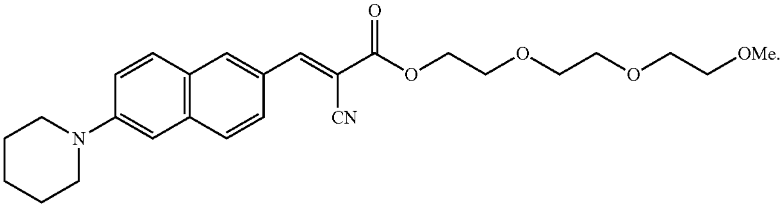 [SMILES: COCCOCCOCCOC(=O)/C(C#N)=C/c1ccc2cc(N3CCCCC3)ccc2c1]

15. The method of claim 7, wherein said compound has the structure:
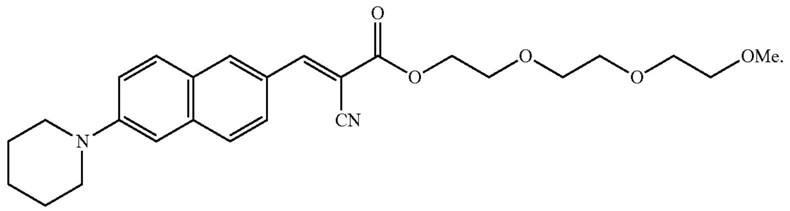
* * * * *

UNITED STATES PATENT AND TRADEMARK OFFICE

CERTIFICATE OF CORRECTION

PATENT NO. : 9,551,722 B2
APPLICATION NO. : 14/572465
DATED : January 24, 2017
INVENTOR(S) : Jerry Yang and Emmanuel A. Theodorakis It is certified that error appears in the above-identified patent and that said Letters Patent is hereby corrected as shown below:

In the Specification

At Column 1, Line 15, please insert --and Grant No. AG005131, both-- between "1E21RR025358" and "awarded".

At Column 1, Line 15, please insert --the-- between "by" and "National".

In the Claims

Claim 1, Column 52, Line 4, please replace "$–OR^2NR^4C(O)R^3$" with -- $–OR^2$, $–NR^4C(O)R^3$--.

Claim 1, Column 52, Line 21, please insert --$R^{11}$-- between "and" and "are".

Claim 1, Column 52, Line 27, please insert --$R^{11}$-- between "and" and "are".

Claim 1, Column 52, Line 62, please insert --,-- between "$–OR^{18}$" and "$–NR^{19}R^{20}$".

Signed and Sealed this
Eighth Day of May, 2018

Andrei Iancu
*Director of the United States Patent and Trademark Office*